US011821047B2

(12) United States Patent
Tudman et al.

(10) Patent No.: US 11,821,047 B2
(45) Date of Patent: Nov. 21, 2023

(54) HIGH PRESSURE ZONE FORMATION FOR PRETREATMENT

(71) Applicant: Apalta Patents OÜ, Möisa tn (EE)

(72) Inventors: Scott Tudman, Honeoye Falls, NY (US); Sharon Samjitsingh, Rochester, NY (US)

(73) Assignee: Apalta Patent OÜ, Möisa (EE)

( * ) Notice: Subject to any disclaimer, the term of this patent is extended or adjusted under 35 U.S.C. 154(b) by 64 days.

(21) Appl. No.: 15/932,340

(22) Filed: Feb. 16, 2018

(65) Prior Publication Data

US 2019/0040478 A1    Feb. 7, 2019

Related U.S. Application Data

(60) Provisional application No. 62/460,037, filed on Feb. 16, 2017.

(51) Int. Cl.
| | | |
|---|---|---|
| C13K 1/02 | (2006.01) | |
| C12P 19/02 | (2006.01) | |
| C12M 1/00 | (2006.01) | |
| C12M 1/33 | (2006.01) | |
| C12P 7/54 | (2006.01) | |
| C12P 19/14 | (2006.01) | |
| C13K 13/00 | (2006.01) | |

(52) U.S. Cl.
CPC ............. *C13K 1/02* (2013.01); *C12M 45/02* (2013.01); *C12M 45/03* (2013.01); *C12M 45/20* (2013.01); *C12P 7/54* (2013.01); *C12P 19/02* (2013.01); *C12P 19/14* (2013.01); *C13K 13/002* (2013.01); *C12P 2201/00* (2013.01)

(58) Field of Classification Search
None
See application file for complete search history.

(56) References Cited

U.S. PATENT DOCUMENTS

| | | | |
|---|---|---|---|
| 1,447,461 A | 3/1923 | Brewster et al. | |
| 1,867,750 A | 7/1932 | Naugle | |
| 2,362,357 A | 11/1944 | Cummins | |
| 2,388,222 A | 10/1945 | Behrman | |
| 2,594,544 A | 4/1952 | Elving et al. | |
| 2,763,580 A | 9/1956 | Zabor | |
| 3,563,799 A | 2/1971 | James et al. | |
| 3,577,358 A | 5/1971 | Thomas et al. | |
| 3,730,770 A | 5/1973 | Zievers et al. | |
| 3,819,292 A | 6/1974 | Wentworth | |
| 4,048,341 A | 9/1977 | Lagerstrom et al. | |
| 4,052,988 A | 10/1977 | Doddi et al. | |
| 4,070,232 A | 1/1978 | Funk | |
| 4,136,207 A * | 1/1979 | Bender ............... | A23K 10/32 162/18 |
| 4,136,968 A | 1/1979 | Todd | |
| 4,182,780 A | 1/1980 | Lagerstrom et al. | |
| 4,186,658 A | 2/1980 | Brown | |
| 4,201,596 A | 5/1980 | Burroughs et al. | |
| 4,214,947 A | 7/1980 | Berger | |
| 4,237,226 A | 12/1980 | Grethlein | |
| 4,242,226 A | 12/1980 | Siren et al. | |
| 4,288,551 A | 9/1981 | Gudnason et al. | |
| 4,326,032 A | 4/1982 | Grove | |
| 4,350,766 A | 9/1982 | Mehlberg | |
| 4,395,488 A | 7/1983 | Rowe | |
| 4,414,330 A | 11/1983 | Zucker et al. | |
| 4,427,584 A | 1/1984 | Legrand et al. | |
| 4,447,534 A | 5/1984 | Moebus et al. | |
| 4,452,973 A | 6/1984 | Casey et al. | |
| 4,478,644 A | 10/1984 | Berger et al. | |
| 4,478,854 A | 10/1984 | Adler-Nissen et al. | |
| 4,502,890 A | 3/1985 | Urbanic | |
| 4,520,105 A | 5/1985 | Sinner et al. | |
| 4,600,590 A | 7/1986 | Dale | |
| 4,612,286 A | 9/1986 | Sherman et al. | |
| 4,615,742 A | 10/1986 | Wright | |
| 4,632,795 A | 12/1986 | Huber et al. | |
| 4,643,191 A | 2/1987 | Bezwada et al. | |
| 4,644,060 A | 2/1987 | Chou | |
| 4,650,689 A | 3/1987 | Hedrick | |

(Continued)

FOREIGN PATENT DOCUMENTS

| | | |
|---|---|---|
| CA | 1267407 B | 4/1990 |
| CN | 101696261 A | 4/2010 |

(Continued)

OTHER PUBLICATIONS

Fang (Continuous steam explosion of wheat straw by high pressure mechanical refining system to produce sugars for bioconversion, BioResources 6(4), 4468-4480, 2011 (Year: 2011).*

Agbor, et al. Biomass pretreatment: fundamentals toward application. Biotechnol Adv. Nov. 2011-Dec. 29(6):675-85. doi: 10.1016/j.biotechadv.2011.05.005. Epub May 23, 2011.

Alcohol and Tobacco Tax and Trade Bureau, treasury. 27 C.F.R. §19.134 Bonded warehouse not on premises qualified for production of spirits, p. 381, Apr. 1, 1997 revision.

Aldrich. 2003-2004. Particle size conversion Table, 2 Pages or p. T848 of the Aldrich 2003-2004 Catalog/ Handbook of Fine Chemicals.

Arshanitsa, et al., Two Approaches for Introduction of Wheat Straw Lignin into Rigid Polyurethane Foams. AIP Conf. Proc. 1593, 388-391 (2014); doi: 10.1063/1.4873806.

(Continued)

*Primary Examiner* — Robert J Yamasaki
(74) *Attorney, Agent, or Firm* — Wilson Sonsini Goodrich & Rosati

(57) ABSTRACT

Disclosed herein are methods, systems, and compositions for the uniform pretreatment of biomass within seconds with low inhibitor formation. The pretreatment process is used to convert biomass to a fuel, sugars, or other useful chemicals by subjecting the feedstock to a rapid retention time under pressure and temperature and/or chemical reactant. The system includes at least one high pressure, steam impermiable plug and a continuously-operating valve discharge apparatus to discharge pretreated feedstock while maintaining uniform pressure on the pretreatment system.

19 Claims, 14 Drawing Sheets

(56) References Cited

U.S. PATENT DOCUMENTS

| | | |
|---|---|---|
| 4,707,278 A | 11/1987 | Breyer et al. |
| 4,716,203 A | 12/1987 | Casey et al. |
| 4,728,367 A | 3/1988 | Huber et al. |
| 4,806,475 A | 2/1989 | Gould |
| 4,862,168 A | 8/1989 | Beard et al. |
| 4,935,183 A | 6/1990 | Wenger et al. |
| 4,942,035 A | 7/1990 | Churchill et al. |
| 5,019,094 A | 5/1991 | Bezwada et al. |
| 5,037,663 A | 8/1991 | Dale |
| 5,080,665 A | 1/1992 | Jarrett et al. |
| 5,114,488 A | 5/1992 | Huber et al. |
| 5,144,008 A | 9/1992 | Ikeda et al. |
| 5,171,592 A | 12/1992 | Holtzapple et al. |
| 5,177,008 A | 1/1993 | Kampen |
| 5,177,009 A | 1/1993 | Kampen |
| 5,232,649 A | 8/1993 | Andersen et al. |
| 5,277,879 A | 1/1994 | Elvin et al. |
| 5,338,366 A | 8/1994 | Grace et al. |
| 5,340,403 A | 8/1994 | Fields et al. |
| 5,378,491 A | 1/1995 | Stanley et al. |
| 5,384,333 A | 1/1995 | Davis et al. |
| 5,449,513 A | 9/1995 | Yokoyama et al. |
| 5,454,911 A | 10/1995 | Rafferty |
| 5,473,061 A | 12/1995 | Bredereck et al. |
| 5,476,909 A | 12/1995 | Kim et al. |
| 5,510,103 A | 4/1996 | Yokoyama et al. |
| 5,543,158 A | 8/1996 | Gref et al. |
| 5,548,035 A | 8/1996 | Kim et al. |
| 5,612,052 A | 3/1997 | Shalaby et al. |
| 5,683,723 A | 11/1997 | Spenlehauer et al. |
| 5,693,296 A | 12/1997 | Holtzapple et al. |
| 5,702,717 A | 12/1997 | Cha et al. |
| 5,726,046 A | 3/1998 | Farone et al. |
| 5,846,787 A | 12/1998 | Ladisch et al. |
| 5,865,898 A | 2/1999 | Holtzapple et al. |
| 5,916,780 A | 6/1999 | Foody et al. |
| 5,939,544 A | 8/1999 | Karstens et al. |
| 5,969,189 A | 10/1999 | Holtzapple et al. |
| 5,986,133 A | 11/1999 | Holtzapple et al. |
| 6,025,452 A | 2/2000 | Kurple |
| 6,043,392 A | 3/2000 | Holtzapple et al. |
| 6,106,888 A | 8/2000 | Dale et al. |
| 6,176,176 B1 | 1/2001 | Dale et al. |
| 6,220,296 B1 | 4/2001 | Ragsdale et al. |
| 6,228,213 B1 | 5/2001 | Hanna et al. |
| 6,247,839 B1 | 6/2001 | Kochanowicz et al. |
| 6,258,175 B1 | 7/2001 | Lightner |
| 6,262,313 B1 | 7/2001 | Holtzapple et al. |
| 6,279,843 B1 | 8/2001 | Coldren et al. |
| 6,316,053 B1 | 11/2001 | Ragsdale et al. |
| 6,332,542 B2 | 12/2001 | Bilodeau et al. |
| 6,355,456 B1 | 3/2002 | Hallberg et al. |
| 6,365,732 B1 | 4/2002 | Van |
| 6,409,841 B1 | 6/2002 | Lombard |
| 6,416,621 B1 | 7/2002 | Karstens |
| 6,475,552 B1 | 11/2002 | Shah et al. |
| 6,478,965 B1 | 11/2002 | Holtzapple et al. |
| 6,509,180 B1 | 1/2003 | Verser et al. |
| 6,541,531 B2 | 4/2003 | Ragsdale |
| 6,599,519 B1 | 7/2003 | Seo et al. |
| 6,616,941 B1 | 9/2003 | Seo et al. |
| 6,872,316 B2 | 3/2005 | Heikkila et al. |
| 6,916,788 B2 | 7/2005 | Seo et al. |
| 6,990,459 B2 | 1/2006 | Schneider |
| 7,109,005 B2 | 9/2006 | Eroma et al. |
| 7,198,925 B2 | 4/2007 | Foody |
| 7,217,770 B2 | 5/2007 | Seo et al. |
| 7,218,975 B2 | 5/2007 | Stevens et al. |
| 7,311,901 B2 | 12/2007 | Seo et al. |
| 7,503,981 B2 | 3/2009 | Wyman et al. |
| 7,521,076 B1 | 4/2009 | Wenger et al. |
| 7,550,157 B2 | 6/2009 | Seo et al. |
| 7,666,637 B2 | 2/2010 | Nguyen |
| 7,807,419 B2 | 10/2010 | Hennessey et al. |
| 7,819,976 B2 | 10/2010 | Friend et al. |
| 7,909,895 B2 | 3/2011 | Dickinson et al. |
| 7,910,338 B2 | 3/2011 | Hennessey et al. |
| 7,930,085 B2 | 4/2011 | Anderson et al. |
| 7,932,063 B2 | 4/2011 | Dunson et al. |
| 7,932,065 B2 | 4/2011 | Medoff |
| 7,935,840 B2 | 5/2011 | Leveson et al. |
| 7,988,884 B2 | 8/2011 | Gatto et al. |
| 8,003,352 B2 | 8/2011 | Foody et al. |
| 8,024,074 B2 | 9/2011 | Stelford et al. |
| 8,053,566 B2 | 11/2011 | Belanger et al. |
| 8,086,354 B2 | 12/2011 | Bondar et al. |
| 8,103,385 B2 | 1/2012 | Macharia et al. |
| 8,110,383 B2 | 2/2012 | Joensson et al. |
| 8,123,864 B2 | 2/2012 | Christensen et al. |
| 8,168,840 B2 | 5/2012 | Brady et al. |
| 8,318,453 B2 | 11/2012 | Medoff |
| 8,323,923 B1 | 12/2012 | Horton |
| 8,328,947 B2 | 12/2012 | Anand et al. |
| 8,394,277 B2 | 3/2013 | Bonanni et al. |
| 8,404,051 B2 | 3/2013 | Iyer et al. |
| 8,426,161 B1 | 4/2013 | Horton |
| 8,445,236 B2 | 5/2013 | Hennessey et al. |
| 8,529,765 B2 | 9/2013 | Horton |
| 8,561,533 B2 | 10/2013 | Burke |
| 8,563,277 B1 | 10/2013 | Parekh et al. |
| 8,691,050 B2 | 4/2014 | Christensen |
| 8,722,924 B1 | 5/2014 | Overheul et al. |
| 8,747,561 B2 | 6/2014 | Tao |
| 8,765,430 B2 | 7/2014 | Parekh et al. |
| 8,835,141 B2 | 9/2014 | Zhu et al. |
| 8,858,065 B1 | 10/2014 | Vandalsem et al. |
| 8,926,794 B2 | 1/2015 | Han et al. |
| 8,926,932 B2 | 1/2015 | Pfeifer et al. |
| 8,967,849 B2 | 3/2015 | Vandalsem et al. |
| 9,004,742 B2 | 4/2015 | Burke et al. |
| 9,056,294 B2 | 6/2015 | Fink et al. |
| 9,115,214 B2 | 8/2015 | Nguyen et al. |
| 9,150,936 B2 | 10/2015 | Dottori et al. |
| 9,410,216 B2 | 8/2016 | Eyal et al. |
| 9,476,106 B2 | 10/2016 | Eyal et al. |
| 9,481,760 B2 | 11/2016 | Mukerjee et al. |
| 9,492,945 B2 | 11/2016 | Niven et al. |
| 9,499,635 B2 | 11/2016 | Arunas et al. |
| 9,499,637 B2 | 11/2016 | Retsina et al. |
| 9,724,213 B2 | 8/2017 | Zhang et al. |
| 9,809,867 B2 | 11/2017 | Parekh et al. |
| 9,931,603 B2 | 4/2018 | Wenger |
| 9,944,559 B2 | 4/2018 | Scharlemann et al. |
| 10,036,049 B2 | 7/2018 | Shaghasi et al. |
| 10,053,745 B2 | 8/2018 | Kilambi et al. |
| 10,344,757 B1 | 7/2019 | Stark et al. |
| 10,844,413 B2 | 11/2020 | Lumpkin |
| 2002/0003058 A1 | 1/2002 | Hori et al. |
| 2002/0038058 A1 | 3/2002 | Holtzapple et al. |
| 2002/0153317 A1 | 10/2002 | Heikkila et al. |
| 2002/0164730 A1 | 11/2002 | Ballesteros et al. |
| 2002/0164731 A1 | 11/2002 | Eroma et al. |
| 2002/0192774 A1 | 12/2002 | Ahring et al. |
| 2002/0197686 A1 | 12/2002 | Lightner |
| 2003/0109011 A1 | 6/2003 | Hood et al. |
| 2003/0143659 A1 | 7/2003 | Bijl et al. |
| 2003/0199049 A1 | 10/2003 | Nguyen et al. |
| 2003/0221361 A1 | 12/2003 | Russell et al. |
| 2003/0224088 A1 | 12/2003 | Burdick |
| 2004/0152881 A1 | 8/2004 | Holtzapple et al. |
| 2004/0168960 A1 | 9/2004 | Holtzapple et al. |
| 2004/0168966 A1 | 9/2004 | Marheine |
| 2004/0171136 A1 | 9/2004 | Holtzapple et al. |
| 2004/0244925 A1 | 12/2004 | Tarasenko |
| 2005/0054064 A1 | 3/2005 | Talluri et al. |
| 2005/0136520 A1 | 6/2005 | Kinley et al. |
| 2005/0203291 A1 | 9/2005 | Svenson et al. |
| 2005/0244934 A1 | 11/2005 | Foody et al. |
| 2005/0271770 A1 | 12/2005 | Hughes |
| 2005/0272134 A1 | 12/2005 | Hughes |
| 2006/0003064 A1 | 1/2006 | James |
| 2006/0020126 A1 | 1/2006 | Kopesky et al. |
| 2006/0024801 A1 | 2/2006 | Holtzapple et al. |
| 2006/0032113 A1 | 2/2006 | Whitney |

(56) References Cited

U.S. PATENT DOCUMENTS

| | | |
|---|---|---|
| 2006/0069244 A1 | 3/2006 | Holtzapple et al. |
| 2006/0090749 A1 | 5/2006 | Rein et al. |
| 2006/0113406 A1 | 6/2006 | Ganser |
| 2006/0188980 A1 | 8/2006 | Holtzapple et al. |
| 2006/0211101 A1 | 9/2006 | Chotani et al. |
| 2006/0251764 A1 | 11/2006 | Abbas et al. |
| 2006/0280663 A1 | 12/2006 | Osato et al. |
| 2006/0281157 A1 | 12/2006 | Chotani et al. |
| 2007/0016095 A1 | 1/2007 | Low et al. |
| 2007/0037259 A1 | 2/2007 | Hennessey et al. |
| 2007/0118916 A1 | 5/2007 | Puzio et al. |
| 2007/0148750 A1 | 6/2007 | Hoshino et al. |
| 2007/0148751 A1 | 6/2007 | Griffin et al. |
| 2007/0164143 A1 | 7/2007 | Sabourin et al. |
| 2007/0190626 A1 | 8/2007 | Wilkening et al. |
| 2007/0237022 A1 | 10/2007 | Wiltz et al. |
| 2007/0275447 A1 | 11/2007 | Lewis et al. |
| 2008/0014617 A1 | 1/2008 | Cerea |
| 2008/0057555 A1 | 3/2008 | Nguyen |
| 2008/0121359 A1 | 5/2008 | Holtzapple et al. |
| 2008/0145903 A1 | 6/2008 | Holmes et al. |
| 2008/0176301 A1 | 7/2008 | Granda et al. |
| 2008/0227162 A1 | 9/2008 | Varanasi et al. |
| 2008/0280338 A1 | 11/2008 | Hall et al. |
| 2008/0286193 A1 | 11/2008 | Bento et al. |
| 2009/0004698 A1 | 1/2009 | Vande et al. |
| 2009/0023187 A1 | 1/2009 | Foody et al. |
| 2009/0042259 A1 | 2/2009 | Dale et al. |
| 2009/0043686 A1 | 2/2009 | Matsumoto |
| 2009/0053800 A1 | 2/2009 | Friend et al. |
| 2009/0064566 A1 | 3/2009 | Brummerstedt et al. |
| 2009/0084801 A1 | 4/2009 | Coe |
| 2009/0098617 A1 | 4/2009 | Burke et al. |
| 2009/0117635 A1 | 5/2009 | Bradley et al. |
| 2009/0118477 A1 | 5/2009 | Hallberg et al. |
| 2009/0126276 A1 | 5/2009 | Johnson et al. |
| 2009/0181434 A1 | 7/2009 | Aikens et al. |
| 2009/0221814 A1 | 9/2009 | Pschorn et al. |
| 2009/0298149 A1 | 12/2009 | Wang et al. |
| 2010/0008998 A1 | 1/2010 | Kang et al. |
| 2010/0021980 A1 | 1/2010 | McDonald et al. |
| 2010/0041119 A1 | 2/2010 | Christensen et al. |
| 2010/0043246 A1 | 2/2010 | Smith et al. |
| 2010/0055741 A1 | 3/2010 | Galvez, III et al. |
| 2010/0056774 A1 | 3/2010 | Anand et al. |
| 2010/0081798 A1 | 4/2010 | Balensiefer et al. |
| 2010/0082139 A1 | 4/2010 | Macharia et al. |
| 2010/0082140 A1 | 4/2010 | Macharia et al. |
| 2010/0082166 A1 | 4/2010 | Macharia et al. |
| 2010/0103769 A1 | 4/2010 | Bachman et al. |
| 2010/0143974 A1 | 6/2010 | Chung et al. |
| 2010/0144001 A1 | 6/2010 | Horton |
| 2010/0216201 A1 | 8/2010 | Soong et al. |
| 2010/0221805 A1 | 9/2010 | Kelly |
| 2010/0221819 A1 | 9/2010 | Foody et al. |
| 2010/0227369 A1 | 9/2010 | Narendranath et al. |
| 2010/0317053 A1 | 12/2010 | Stromberg et al. |
| 2011/0020874 A1 | 1/2011 | Hata |
| 2011/0033268 A1 | 2/2011 | Craig et al. |
| 2011/0039317 A1 | 2/2011 | Medoff |
| 2011/0054059 A1 | 3/2011 | Li et al. |
| 2011/0079219 A1 | 4/2011 | McDonald et al. |
| 2011/0081689 A1 | 4/2011 | Flanegan et al. |
| 2011/0114765 A1 | 5/2011 | Brady et al. |
| 2011/0129886 A1 | 6/2011 | Howard et al. |
| 2011/0171709 A1 | 7/2011 | Bardsley et al. |
| 2011/0175358 A1 | 7/2011 | Langson |
| 2011/0197496 A1 | 8/2011 | O'Connor et al. |
| 2011/0201084 A1 | 8/2011 | Wyman et al. |
| 2011/0212487 A1 | 9/2011 | Emme et al. |
| 2011/0223641 A1 | 9/2011 | Stephanopoulos et al. |
| 2011/0244499 A1 | 10/2011 | Realff et al. |
| 2011/0258911 A1 | 10/2011 | Hanson et al. |
| 2011/0258913 A1 | 10/2011 | Stamires et al. |
| 2011/0262985 A1* | 10/2011 | Medoff .................. C12P 19/02 435/165 |
| 2011/0275860 A1 | 11/2011 | Beldring et al. |
| 2011/0300586 A1 | 12/2011 | Liu et al. |
| 2012/0006320 A1 | 1/2012 | Nguyen |
| 2012/0037325 A1 | 2/2012 | Beldring et al. |
| 2012/0041186 A1 | 2/2012 | Pschorn et al. |
| 2012/0100045 A1 | 4/2012 | Beldring et al. |
| 2012/0100577 A1 | 4/2012 | Medoff et al. |
| 2012/0107888 A1 | 5/2012 | Schmalisch et al. |
| 2012/0108798 A1 | 5/2012 | Wenger et al. |
| 2012/0116063 A1 | 5/2012 | Jansen et al. |
| 2012/0122162 A1 | 5/2012 | Romero et al. |
| 2012/0125324 A1* | 5/2012 | Fisk ........................ C11B 1/00 127/1 |
| 2012/0125738 A1* | 5/2012 | Ikeda .................... B29C 48/565 198/676 |
| 2012/0184721 A1* | 7/2012 | Wingerson ............... D21B 1/30 530/507 |
| 2012/0190092 A1 | 7/2012 | Jaquess et al. |
| 2012/0196233 A1 | 8/2012 | Ni et al. |
| 2012/0211427 A1 | 8/2012 | Bonanni et al. |
| 2012/0214205 A1* | 8/2012 | Iida ........................ C12M 33/16 435/72 |
| 2012/0214216 A1 | 8/2012 | Brady et al. |
| 2012/0269715 A1 | 10/2012 | Kamegawa et al. |
| 2012/0282655 A1 | 11/2012 | Gibbs |
| 2012/0302699 A1 | 11/2012 | Kobune et al. |
| 2013/0014749 A1 | 1/2013 | Dottori et al. |
| 2013/0071903 A1 | 3/2013 | Rowland et al. |
| 2013/0118483 A1 | 5/2013 | Gao et al. |
| 2013/0172540 A1 | 7/2013 | Simard et al. |
| 2013/0199518 A1 | 8/2013 | Dahl |
| 2013/0210101 A1 | 8/2013 | Parekh et al. |
| 2013/0225854 A1 | 8/2013 | Ryba et al. |
| 2013/0252293 A1 | 9/2013 | Chen et al. |
| 2013/0274455 A1 | 10/2013 | Parekh et al. |
| 2013/0274456 A1 | 10/2013 | Parekh et al. |
| 2013/0323830 A1 | 12/2013 | Horton |
| 2014/0034047 A1 | 2/2014 | Retsina et al. |
| 2014/0038243 A1 | 2/2014 | Balan et al. |
| 2014/0106418 A1 | 4/2014 | Parekh et al. |
| 2014/0110324 A1 | 4/2014 | Lehoux et al. |
| 2014/0121359 A1 | 5/2014 | Thies et al. |
| 2014/0154756 A1 | 6/2014 | Nelson et al. |
| 2014/0178944 A1 | 6/2014 | Parekh et al. |
| 2014/0188543 A1 | 7/2014 | Pearlmutter et al. |
| 2014/0200334 A1 | 7/2014 | Lake et al. |
| 2014/0242867 A1 | 8/2014 | Jansen et al. |
| 2014/0248676 A1 | 9/2014 | Griffin et al. |
| 2014/0262727 A1 | 9/2014 | Felix et al. |
| 2014/0275500 A1 | 9/2014 | Mikhnevich et al. |
| 2014/0342423 A1 | 11/2014 | Parekh et al. |
| 2015/0018584 A1 | 1/2015 | Parekh et al. |
| 2015/0075738 A1 | 3/2015 | Wimby et al. |
| 2015/0183948 A1 | 7/2015 | Chuang et al. |
| 2015/0196893 A1 | 7/2015 | Mennell et al. |
| 2015/0197424 A1 | 7/2015 | Mennell et al. |
| 2015/0224428 A1 | 8/2015 | Lehoux et al. |
| 2015/0232902 A1 | 8/2015 | Romero et al. |
| 2015/0322170 A1 | 11/2015 | Haggblom et al. |
| 2015/0329927 A1 | 11/2015 | Parekh |
| 2015/0343405 A1 | 12/2015 | Gastaldo et al. |
| 2015/0368441 A1 | 12/2015 | Retsina et al. |
| 2016/0002467 A1 | 1/2016 | Erdmann et al. |
| 2016/0031713 A1 | 2/2016 | Fish et al. |
| 2016/0032414 A1 | 2/2016 | Parekh et al. |
| 2016/0032525 A1 | 2/2016 | Kurple et al. |
| 2016/0194433 A1 | 7/2016 | Langlois et al. |
| 2016/0222045 A1 | 8/2016 | Argyropoulos |
| 2016/0268107 A1 | 9/2016 | White et al. |
| 2016/0273009 A1 | 9/2016 | Lumpkin et al. |
| 2016/0312259 A1 | 10/2016 | Vainio et al. |
| 2016/0333146 A1 | 11/2016 | Miettinen et al. |
| 2017/0016179 A1 | 1/2017 | Olkowski et al. |
| 2017/0226535 A1 | 8/2017 | Tudman |
| 2017/0247255 A1 | 8/2017 | Wittmann et al. |
| 2017/0313826 A1 | 11/2017 | Jansen et al. |
| 2018/0002451 A1 | 1/2018 | Ge et al. |

(56) References Cited

U.S. PATENT DOCUMENTS

| | | | |
|---|---|---|---|
| 2018/0016355 A1 | 1/2018 | Nelson et al. | |
| 2018/0030555 A1 | 2/2018 | Van Tuel et al. | |
| 2018/0079871 A1 | 3/2018 | Tudman | |
| 2019/0010660 A1 | 1/2019 | Srivastava et al. | |
| 2019/0390405 A1 | 12/2019 | Geigle et al. | |

FOREIGN PATENT DOCUMENTS

| | | |
|---|---|---|
| CN | 102216435 A | 10/2011 |
| CN | 102585248 A | 7/2012 |
| EP | 0037912 A2 | 10/1981 |
| EP | 0105937 B1 | 11/1987 |
| EP | 0364632 A1 | 4/1990 |
| EP | 0150933 B2 | 8/1997 |
| EP | 1259466 B1 | 10/2008 |
| EP | 1307735 B1 | 11/2008 |
| EP | 1299170 B1 | 8/2010 |
| EP | 2812437 A1 | 12/2014 |
| EP | 2836602 A1 | 2/2015 |
| JP | 2006149343 A | 6/2006 |
| KR | 20100123093 A | 11/2010 |
| KR | 20110046090 | 5/2011 |
| KR | 20110046090 A | 5/2011 |
| KR | 20130115577 | 10/2013 |
| KR | 20130115577 A | 10/2013 |
| KR | 101391435 B1 | 5/2014 |
| KR | 20140072866 A | 6/2014 |
| WO | WO-9640970 A1 | 12/1996 |
| WO | WO-0132715 A1 | 5/2001 |
| WO | WO-0160752 A1 | 8/2001 |
| WO | WO-0200324 A1 | 1/2002 |
| WO | WO-0201220 A2 | 1/2002 |
| WO | WO-0201220 A3 | 9/2002 |
| WO | WO-2004011501 A1 | 2/2004 |
| WO | WO-2004081193 A2 | 9/2004 |
| WO | WO-2004108969 A1 | 12/2004 |
| WO | WO-2004113551 A1 | 12/2004 |
| WO | WO-2005052195 A1 | 6/2005 |
| WO | WO-2005087937 A2 | 9/2005 |
| WO | WO-2005118828 A1 | 12/2005 |
| WO | WO-2006024242 A1 | 3/2006 |
| WO | WO-2006031175 A1 | 3/2006 |
| WO | WO-2006101832 A2 | 9/2006 |
| WO | WO-2007009463 A2 | 1/2007 |
| WO | WO-2007009463 A3 | 7/2007 |
| WO | WO-2008020901 A2 | 2/2008 |
| WO | WO-2008073186 A2 | 6/2008 |
| WO | WO-2006101832 A3 | 4/2009 |
| WO | WO-2009045651 A2 | 4/2009 |
| WO | WO-2009058276 A1 | 5/2009 |
| WO | WO-2009063138 A2 | 5/2009 |
| WO | WO-2009087680 A2 | 7/2009 |
| WO | WO-2010011328 A1 | 1/2010 |
| WO | WO-2010034055 A1 | 4/2010 |
| WO | WO-2010037780 A1 | 4/2010 |
| WO | WO-2010056940 A2 | 5/2010 |
| WO | WO-2010068637 A1 | 6/2010 |
| WO | WO-2010115488 A1 | 10/2010 |
| WO | WO-2010121348 A1 | 10/2010 |
| WO | WO-2010123932 A1 | 10/2010 |
| WO | WO-2011003962 A2 | 1/2011 |
| WO | WO-2011022811 A1 | 3/2011 |
| WO | WO-2011028554 A1 | 3/2011 |
| WO | WO-2011028853 A1 | 3/2011 |
| WO | WO-2011095335 A1 | 8/2011 |
| WO | WO-2011103033 A1 | 8/2011 |
| WO | WO-2012051523 A1 | 4/2012 |
| WO | WO-2012099967 A1 | 7/2012 |
| WO | WO-2012155239 A1 | 11/2012 |
| WO | WO-2013083876 A2 | 6/2013 |
| WO | WO-2013120035 A1 | 8/2013 |
| WO | WO-2013148415 A1 | 10/2013 |
| WO | WO-2013155496 A1 | 10/2013 |
| WO | WO-2013186184 A1 | 12/2013 |
| WO | WO-2014026154 A1 | 2/2014 |
| WO | WO-2014039984 A1 | 3/2014 |
| WO | WO-2013083876 A3 | 5/2014 |
| WO | WO-2014143753 A1 | 9/2014 |
| WO | WO-2014169079 A2 | 10/2014 |
| WO | WO-2014190294 A1 | 11/2014 |
| WO | WO-2015044528 A1 | 4/2015 |
| WO | WO-2015079107 A1 | 6/2015 |
| WO | WO-2015179243 A1 | 11/2015 |
| WO | WO-2016001484 A1 | 1/2016 |
| WO | WO-2016094594 A1 | 6/2016 |
| WO | WO-2016128224 A1 | 8/2016 |
| WO | WO-2017037349 A1 | 3/2017 |
| WO | WO-2017049090 A1 | 3/2017 |
| WO | WO-2018151833 A1 | 8/2018 |
| WO | WO-2019094444 A1 | 5/2019 |
| WO | WO-2020160565 A1 | 8/2020 |

OTHER PUBLICATIONS

Ballesteros, et al. Ethanol from lignocellulose materials by a simultaneous saccharification and fermentation process (SFS) with Kluyveromyces marxianus CECT 10875. Process Biochemistry, vol. 39, pp. 1843-1848, 2004.

Boggan. 2003. Alcohol, Chemistry and You Sources and Uses of Ethyl Alcohol. Kennesaw State University, pp. 1-5, Printed 05172010. http://www.chemcases.com/alcohol/alc-03.htm/.

Bolsen, et al. Silage Fermentation and Silage Additives: Review. AJAS 1996 vol. 9 (No. 5). pp. 483-493.

Brigham, et al. Bacterial Carbon Storage to Value Added Products. J Microbial Biochem Technol 2011, S3-002.

Dale, et al. Hydrolysis of lignocellulosics at low enzyme levels: Application of the AFEX process. Bioresource Technology. Apr. 1996; 56(1):111-116.

Dasari, et al. The effect of particle size on hydrolysis reaction rates and rheological properties in cellulosic slurries. Appl Biochem Biotechnol. Apr. 2007;136-140(1-12):289-99. doi: 10.1007/s12010-007-9059-x.

David W. Templeton, " Assessing corn stover composition and sources of variability via NIRS", Cellulose (2009) 16:621-639.

Dionex CarboPac PA10. Column Product Manual. Thermo Scientific. P/N: 065495-01. Dec. 2012.

Dowe, et al. 2001. SSF Experimental Protocols—Lignocellulosic Biomass Hydrolysis and Fermentation Laboratory Analytical Procedure (LAP), National Renewable Energy Laboratory. 1617 Cole Boulevard, Golden, Colorado. Issue Date: Oct. 30, 2001, pp. 1-18.

Dowe, et al. (SSF Experimental Protocols—Lignocellulosic Biomass Hydrolysis and Fermentation. Laboratory Analytical Procedure (LAP), Issue Date: Oct. 30, 2001. National Renewable Energy Laboratory, 1617 Cole Boulevard, Golden, Colorado 80401-3393, 76 Pages) 2008.

Felix et al. In vitro and in vivo digestibility of soya-bean straw treated with various alkalis. Anim Prod. 1990; 51:47-61.

Gibreel, et al. Fermentation of barley by using Saccharomyces cerevisiae: examination of barley as a feedstock for bioethanol production and value-added products. Appl Environ Microbiol. Mar. 2009;75(5):1363-72. doi: 10.1128/AEM.01512-08. Epub Dec. 2, 20089.

Gregorova, et al., Lignin-Containing Polyethylene Films With Antibacterial Activity.Brno, Czech Republic, EU, 2011; 21-23, 9.

Gum, et al. Structural characterization of a glycoprotein cellulase, 1,4-beta-D-glucan cellubiohydrolase C from trichodermaviride. Biochem. Biophys. Acta. 1976; 446:370-86.

Hong-Zhang Chen and Zhi-Hua Liu, "Steam explosion and its combinatorial pretreatment refining technology of plant biomass to bio-based products", Biotechnology Journal, 2015, 10, 866-885.

Jin, et al., Liquefaction of lignin by polyethyleneglycol and glycerol. Bioresource Technology 102 (2011) 3581-3583.

Jones, et al. (1994, Ethanolic Fermentation of Blackstrap Molasses and Sugarcane Juice Using Very High Gravity Technology. J. Agric. Food Chem, vol. 42, pp. 1242-1246).

Kamal, et al., Detoxification of sago trunk hydrolysate using activated charcoal for xylitol production, Procedia Food Science 1, (2011) 908-913.

(56) References Cited

OTHER PUBLICATIONS

Kim, et al. Lime pretreatment and enzymatic hydrolysis of corn stover. Bioresour Technol. Dec. 2005;96(18):1994-2006.
Kim, et al. Pretreatment and fractionation of corn stover by ammonia recycle percolation process. Bioresour Technol. Dec. 2005; 96(18):2007-13.
Larsson, et al. Comparison of different methods for the detoxification of lignocellulose hydrolyzates of spruce. Applied Biochemistry and Biotechnology. 1999; 77-79:91-103.
Lignimatch. Future use of lignin in value added products: A roadmap for possible Nordic/Baltic innovation. The roadmap compiles inputs from the detailed technical reports delivered in the LigniMatch project during 2007-2009. For more information, see the project website at http://www.chalmers.se/gmv/EN/projects/lignimatch.
Lloyd, et al. Combined sugar yields for dilute sulfuric acid pretreatment of corn stover followed by enzymatic hydrolysis of the remaining solids. Bioresour Technol. Dec. 2005; 96(18):1967-77.
Malherbe, et al. Lignocellulose biodegradation: Fundamentals and applications. Re/Views in Environmental Science & Bio/Technology. 2001; 1:105-114.
Marie Linde et al., " Steam Pretreatment of Acid-Sprayed and Acid-Soaked Barley Straw for Production of Ethanol", Applied Biochemistry and Biotechnology, vol. 129-132, 2006.
Milford Hanna et al., "Production of Microcrystalline Cellulose by Reactive Extrusion", University of Nebraska—Lincoln Digital Commons@University of Nebraska—Lincoln, May 8, 2001.
Mosier, et al. Features of promising technologies for pretreatment of lignocellulosic biomass. Bioresour Technol. Apr. 2005;96(6):673-86.
Mosier, et al. Optimization of pH controlled liquid hot water pretreatment of corn stover. Bioresour Technol. Dec. 2005;96(18):1986-93.
Nevoigt, et al. Osmoregulation and glycerol metabolism in the yeast *Saccharomyces cerevisiae*. FEMS Microbiol Rev. Nov. 1997;21(3):231-41.
Notice of allowance dated Jan. 9, 2013 for U.S. Appl. No. 13/646,425.
Notice of allowance dated Feb. 20, 2014 for U.S. Appl. No. 13/731,633.
Notice of allowance dated Jun. 7, 2013 for U.S. Appl. No. 12/633,555.
"Notice of allowance dated Jun. 27, 2017 for U.S. Appl. No. 14/776,411".
Notice of allowance dated Jul. 8, 2013 for U.S. Appl. No. 13/686,477.
Notice of allowance dated Jul. 14, 2016 for U.S. Appl. No. 14/050,244.
Notice of allowance dated Aug. 8, 2013 for U.S. Appl. No. 12/633,555.
Notice of allowance dated Oct. 15, 2012 for U.S. Appl. No. 11/974,129.
Office action dated Jan. 5, 2016 for U.S. Appl. No. 14/050,244.
"Office action dated Feb. 5, 2016 for U.S. Appl. No. 13/947,368."
Office action dated Feb. 20, 2013 for U.S. Appl. No. 13/686,477.
Office action dated Mar. 10, 2015 for U.S. Appl. No. 13/931,303.
Office action dated Mar. 12, 2015 for U.S. Appl. No. 14/050,244.
Office action dated Mar. 20, 2013 for U.S. Appl. No. 12/633,555.
Office action dated Mar. 24, 2014 for U.S. Appl. No. 13/724,763.
Office action dated Apr. 7, 2016 for U.S. Appl. No. 14/050,244.
Office action dated May 24, 2010 for U.S. Appl. No. 11/974,129.
Office action dated Jun. 25, 2013 for U.S. Appl. No. 13/731,633.
Office action dated Jul. 6, 2012 for U.S. Appl. No. 11/974,129.
"Office action dated Jul. 9, 2015 for U.S. Appl. No. 13/793,860."
"Office action dated Jul. 12, 2017 for U.S. Appl. No. 14/713,906".
Office action dated Jul. 28, 2016 for U.S. Appl. No. 14/254,441.
"Office action dated Sep. 11, 2015 for U.S. Appl. No. 14/254,441."
Office action dated Sep. 16, 2016 for U.S. Appl. No. 13/947,368.
"Office action dated Sep. 21, 2015 for U.S. Appl. No. 13/842,941."
Office action dated Oct. 3, 2012 for U.S. Appl. No. 12/633,555.
Office action dated Oct. 8, 2014 for U.S. Appl. No. 13/793,860.
Office action dated Oct. 18, 2013 for U.S. Appl. No. 13/724,763.
Office action dated Nov. 8, 2010 for U.S. Appl. No. 11/974,129.
"Office Action dated Nov. 8, 2017 for U.S. Appl. No. 14/340,179".
Office action dated Jan. 19, 2017 for U.S. Appl. No. 14/340,179.
Office action dated Dec. 5, 2016 for U.S. Appl. No. 13/842,941.
Office action dated Dec. 15, 2016 for U.S. Appl. No. 14/776,411.
Office action dated Dec. 29, 2014 for U.S. Appl. No. 13/842,941.
Office action dated Jan. 23, 2017 for U.S. Appl. No. 14/140,880.
Opposition against EP 2 836 602 dated Jul. 3, 2019 (21 pages).
Palmqvist, et al. Fermentation of lignocellulosic hydrolysates. I: inhibition and detoxification. Bioresource Technology. 2000; 74(1):17-24.
Parekh, et al. Production of glycerol by hansenula anomala. Biotechnol Bioeng. Jul. 1985;27(7):1089-91.
Quang A. Nguyen et al., "Two-Stage Dilute-Acid Pretreatment of Softwoods", Applied Biochemistry and Biotechnolgy, vol. 84-86, 200, 561-576.
"Quantitative Instrument Analysis, https://www.gmu.edu/depts/SRIF/tutorial/gcd/quant.htm, p, s1-3; Updated May 8, 1998, Printed Jun. 23, 2015."
Santoro, et al. A High-throughput Platform for Screening Milligram Quantities of Plant Biomass for Lignocellulose Digestibility. Bioenerg. Res. Jan. 2010; 3:93-102.
Shapouri, et al. 2006. The Economic Feasibility of Ethanol Production From Sugar in the United States, USDA, 78 Pages, Jul. 2006.
Shijie Liu, "Woody biomass: Niche position as a source of sustainable renewable chemicals and energy and kinetics of hot-water extraction/hydrolysis", Biotechnology Advances 28 (2010) 563-582.
Silva, et al. Downstream processing for xylitol recovery from fermented sugar cane bagasse hydrolysate using aluminium polychloride. Z Naturforsch C. Jan.-Feb. 2000; 55(1-2):10-5.
Sluiter, et al. Determination of structural carbohydrates and lignin in biomass. National Renewable Energy Laboratory. Technical report NREL/TP-510-42618. Revised Jun. 2010.
Huang, et al., Characterization of Biobased Polyurethane Foams Employing Lignin Fractionated from Microwave Liquefied Switchgrass. Hindawi International Journal of Polymer Science vol. 2017, Article ID 4207367, 8 pages https://doi.org/10.1155/2017/4207367.
Borregaard, Potential applications for different lignin sources based on experience from Borregaard and what about the future? Oct. 21, 2015; 26 Pages.
Sun, et al. Dilute acid pretreatment of rye straw and bermudagrass for ethanol production. Bioresour Technol. Sep. 2005;96(14):1599-606. Epub Feb. 24, 2005.
Taherzadeh, et al. Pretreatment of Lignocellulosic Wastes to Improve Ethanol and Biogas Production: A Review. International Journal of Molecular Sciences. 2008(9). pp. 1621-1651.
Taylor. From Raw Sugar to Raw materials. Chemical innovation. 2000; 30:45-48.
U.S. Appl. No. 14/340,179 Office Action dated Sep. 4, 2018.
U.S. Appl. No. 13/793,860 Office Action dated Apr. 7, 2016.
U.S. Appl. No. 15/267,617 Office Action dated Apr. 27, 2018.
USDA, "The Economic Feasibility of Ethanol Production From Sugar in the United States"; Jul. 2006, 69 pages.
Valery B. Agbor et al., "Biomass pretreatment: Fundamentals toward application", Biotechnology Advances 29 (2011) 675-685.
Varhegyi, et al. (1989. Kinetics of the thermal decomposition of cellulose, hemicellulose, and sugarcane bagasse. Energy Fuels, vol. 3, No. 3, pp. 329-335).
Waiss, et al. Improving Digestibility of Straws for Ruminant Feed by Aqueous Ammonia. Journal of Animal Science. 1972; 35(1):109-112.
Wallace., "Feasibility Study of Co-Locating and Integrating Ethanol Production Plants from Corn Starch and Lignocellulosic Feedstocks. United States Department of Agriculture, United States Department of Energy, 2005, NREL, Golden Colorado, Wyndmoor, PA."
Waltermann, et al. Rhodococcus opacus strain PD630 as a new source of high-value single-cell oil? Isolation and characterization of triacylglycerols and other storage lipids. Microbiology. 2000; 146:1143-1149.
Wen-Hua Chen et al., "Pretreatment efficiency and structural characterization of rice straw by an integrated process of dilute-acid and steam explosion for bioethanol production", Bioresource Technology 102 (2011) 2916-2924.

(56) References Cited

OTHER PUBLICATIONS

Woiciechowski, et al. Acid and Enzymatic Hydrolysis to Recover Reducing Sugars from Cassava Bagasse: an Economic Study. Brazilian Archives of Biology and Technology, vol. 45, No. 3, pp. 393-400, 2002.

Xue, et al., Producing Lignin-Based Polyols through Microwave-Assisted Liquefaction for Rigid Polyurethane Foam Production. Materials 2015, 8, 586-599; doi:10.3390/ma8020586.

"Zheng, et al. Extrusion Pretreatment of Lignocellulosic Biomass: A Review. Int. J. Mol. Sci. Oct. 2014, 15, 18967-18984."

Zou, et al. Preparation of Activated Carbons from Chinese Coal and Hydrolysis Lignin. Adsorption Science & Technology. 2001; 19(1): 59-72.

Cambridge University Press. (n.d.). Cut. In Cambridge Dictionary. Retrieved Sep. 2022, from https://dictionary.cambridge.org/us/dictionary/english/cut.

Cateto, C.A., et al. Lignins as macromonomers for polyurethane synthesis: A comparative study on hydroxyl group determination. Journal of Applied Polymer Science. Sep. 5, 2008;109(5):3008-17.

Chen, et al., "Pretreatment efficiency and structural characterization of rice straw by an integrated process of dilute-acid and steam explosion for bioethanol production" (2010) Bioresource Technology, 102, pp. 2916-2924.

ConvertUnits.com. (n.d.). psig to kpa conversion. In ConvertUnits.com. Retrieved Sep. 2022, from https://www.convertunits.com/from/psig/to/kpa.

Dictionary.com, LLC. (n.d.). Blender. In Dictionary.com. Retrieved Sep. 2022, from https://www.dictionary.com/browse/blender.

Fernandes Diniz, J. M. B., M. H. Gil, and J. A. A. M. Castro., "Hornification-its origin and interpretation in wood pulps." Wood Science and Technology 37.6 (2004): 489-494.

Guragain Y.N., et al. Novel biomass pretreatment using alkaline organic solvents: a green approach for biomass fractionation and 2,3-butanediol production. BioEnergy Research. Jun. 2016;9(2):643-55.

Holladay, JE, et al., "Top Value Added chemicals from Biomass", (2007). vol. II, Pacific Northwest National Laboratory (PNNL) and the National Renewable Energy Laboratory (NREL).

Hong-Zhang Chen and Zhi-Hua Liu, "Stem explosion and its combinatorial pretreatment refining technology of plant biomass to bio-based products", Biotechnology Journal, 2015, 10, pp. 866-885.

Li T, Takkellapati S. The current and emerging sources of technical lignins and their applications. Biofuel Bioprod Biorefin. Jul. 18, 2018;0:1-32.

Lloyd TA, Wyman CE., Combined sugar yields for dilute sulfuric acid pretreatment of corn stover followed by enzymatic hydrolysis of the remaining solids, Bioresour Technol. Dec. 2005;96(18):1967-77.doi: 10.1016/j.biortech.2005.01.011. PMID: 16112484.

Lourençon T.V., et al. Hardwood and softwood kraft lignins fractionation by simple sequential acid precipitation. Separation and purification technology. Nov. 5, 2015;154:82-8.

Mancera A, et al. Physicochemical characterisation of sugar cane bagasse lignin oxidized by hydrogen peroxide. Polymer Degradation and Stability. Apr. 1, 2010;95(4):470-6.

Merriam-Webster. (n.d.). Shear. In Merriam-Webster Dictionary. Retrieved Sep. 2022, from https://www.merriam-webster.com/dictionary/shear.

Office action dated Mar. 3, 2021 for U.S. Appl. No. 14/340,179.
Office action dated Mar. 30, 2020 for U.S. Appl. No. 14/340,179.
Office action dated Jun. 23, 2022 for U.S. Appl. No. 16/760,416.
Office action dated Jun. 27, 2019 for U.S. Appl. No. 14/340,179.
Office action dated Jul. 5, 2022 for U.S. Appl. No. 17/076,269.
Office action dated Sep. 29, 2022 for U.S. Appl. No. 17/465,382.

Oxford University Press. (n.d.). Concurrent. In Oxford Lexico Dictionary. Retrieved Sep. 2022, from https://www.dictionary.com/browse/concurrent.

Ramos LP. The chemistry involved in the steam treatment of lignocellulosic materials. Química Nova. Dec. 2003;26(6):863-71.

Shijie Liu "Woody biomass: Niche position as a source of sustainable renewable chemicals and energy and kinetics of hot-water extraction/hydrolysis", Biotechnology Advances 28 (2010) pp. 563-582.

Tucker, et al., "Effects of Temperature and Moisture" (2003) Applied Biochemistry and Biotechnology, 105-108, pp. 165-177.

Wang G, Chen H. Fractionation of alkali-extracted lignin from steam-exploded stalk by gradient acid precipitation. Separation and Purification Technology. Feb. 5, 2013;105:98-105. Epub Dec. 20, 2012.

Yoshida, H. et al., Kraft lignin in polyurethanes. II. Effects of the molecular weight of kraft lignin on the properties of polyurethanes from a kraft lignin-polyether triol-polymeric MDI system. Journal of Applied Polymer Science. 40. 1819-1832. (1990). Abstract.

* cited by examiner

HIGH PRESSURE ZONE FORMATION FOR PRETREATMENT

CROSS-REFERENCE

This application claims the benefit of U.S. Provisional Application No. 62/460,037, filed Feb. 16, 2017, which application is incorporated herein by reference in its entirety.

BACKGROUND

Extrusion devices are of a highly versatile nature and can be used for the production of a wide variety of end products. Extruders can be used to pretreat materials containing polymers, including biomass materials such as agricultural residues and woody materials. Such materials have varying densities, chemical bonds, moisture content and expansion ratios, making it difficult to process them. In the production of pretreatment end-products from biomass, it can be useful to carry out the pretreatment hydrolysis reactions as quickly and efficiently as possible to prevent exposure of the materials to excessively severe conditions resulting in the formation of inhibitors. It can also be important, to keep the temperature and pressure constant and uniform in the process. In this manner, cellulose and hemicellulose polymers can be separated from lignin polymers quickly and efficiently. Improved pretreatment techniques are desirable for better efficiency of converting biomass from renewable resources and/or waste materials to high yields of more valuable products.

One pretreatment process for producing hydrolyzed polymers from biomass is carried out by exposing the feedstock to dilute acid, high temperature, and high pressure steam for a period of time followed by steam explosion. To accomplish this treatment uniformly throughout the biomass, the biomass can be subjected to size reduction by milling, grinding, shredding or other mechanical action, can be further reduced in size to very small particles, and then fed into a short reaction zone where it is treated within a few seconds prior to steam explosion. (See, US20160273009A1) The small size of the particles allows the treatment to be efficiently executed without underexposure or overexposure to acid, temperature and pressure. However, it is difficult to reduce size uniformly and pretreat as biomass is moving through the system, because it is hard to maintain constant pressure. Modifications to such techniques can improve the efficiency of converting biomass from renewable resources and/or waste materials to high yields of more valuable products.

SUMMARY

In one aspect, disclosed herein are industrial scale methods for pretreating biomass, the method comprising: (a) feeding the biomass into an extrusion system comprising: (i) a barrel defining an inner chamber comprising a feeder zone and a reaction zone; and (ii) one or more rotatable screws configured to move the biomass through the extrusion system from the feeder zone through the reaction zone, wherein the one or more rotatable screws comprise section elements configured to form: (1) a preconditioning section in the feeder zone that produces a homogenized biomass by reducing particle size of the biomass and evenly distributing water within the biomass, and (2) a high pressure zone that compacts the homogenized biomass to form a steam impervious plug separating the feeder zone and the reaction zone; and (b) treating the biomass at an elevated temperature and pressure within the reaction zone for less than about one minute to produce a pretreated biomass composition comprising a liquid/solids fraction comprising monosaccharides and solid particles comprising cellulose and/or lignin.

In another aspect, disclosed herein are pretreated biomass compositions produced by the methods disclosed herein.

In another aspect, disclosed herein are systems for industrial scale pretreatment of biomass, the system comprising: (a) a barrel defining an inner chamber comprising a feeder zone and a reaction zone; and (b) one or more rotatable screws configured to move the biomass through the inner chamber of the barrel from the feeder zone through the reaction zone, wherein the one or more rotatable screws comprise section elements configured to form: (1) a preconditioning section in the feeder zone that produces a homogenized biomass by reducing particle size of the biomass and evenly distributing water within the biomass, and (2) a high pressure zone that compacts the homogenized biomass to form a steam impervious plug separating the feeder zone and the reaction zone; wherein the system is configured to treat the biomass at an elevated temperature and pressure within the reaction zone for less than about one minute to produce a pretreated biomass composition comprising a liquid fraction comprising monosaccharides and solid particles comprising cellulose, lignin or a combination thereof.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent that a term incorporated by reference conflicts with a term defined herein, this specification shall control.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION

Figure 1:
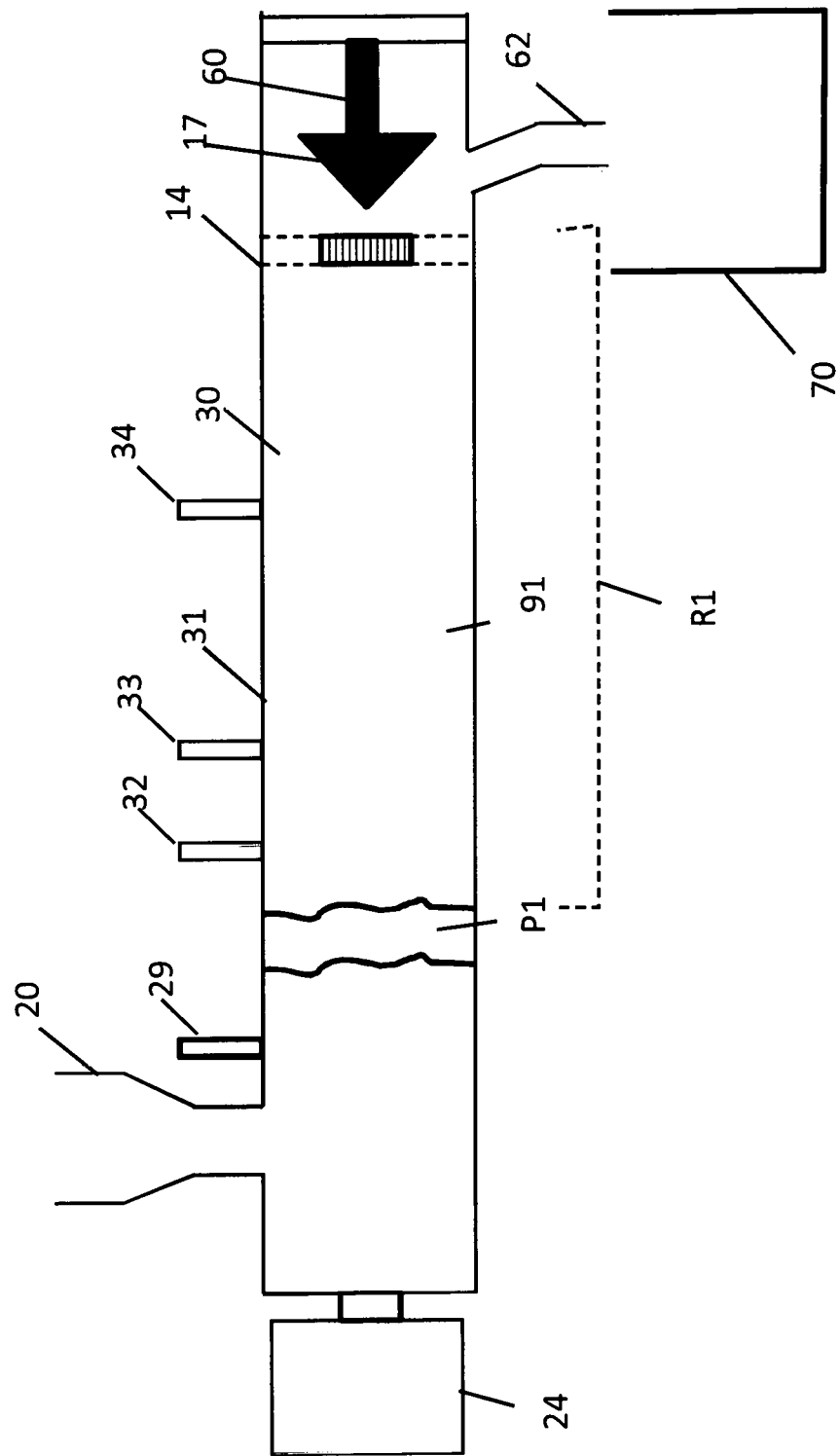
FIG. 1 is a schematic diagram of one embodiment of an apparatus disclosed herein with one impermeable plug.

As used in the specification and the appended claims, the singular forms "a," "an" and "the" include plural referents unless the context clearly dictates otherwise. Thus, for example, reference to "a purified monomer" includes mixtures of two or more purified monomers. The term "comprising" as used herein is synonymous with "including," "containing," or "characterized by," and is inclusive or open-ended and does not exclude additional, unrecited elements or method steps.

All numbers expressing quantities of ingredients, reaction conditions, and so forth used in the specification are to be understood as being modified in all instances by the term "about." Accordingly, unless indicated to the contrary, the numerical parameters set forth herein are approximations that can vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

Wherever the phrase "for example," "such as," "including" and the like are used herein, the phrase "and without limitation" is understood to follow unless explicitly stated otherwise. Therefore, "for example ethanol production" means "for example and without limitation ethanol production."

In this specification and in the claims that follow, reference will be made to a number of terms which shall be defined to have the following meanings. Unless characterized otherwise, technical and scientific terms used herein have the same meaning as commonly understood by one of ordinary skill in the art.

Definitions

Unless characterized otherwise, technical and scientific terms used herein have the same meaning as commonly understood by one of ordinary skill in the art.

"Optional" or "optionally" means that the subsequently described event or circumstance may or may not occur, and that the description includes instances where said event or circumstance occurs and instances where it does not. For example, the phrase "the medium can optionally contain glucose" means that the medium may or may not contain glucose as an ingredient and that the description includes both media containing glucose and media not containing glucose.

"About" means a referenced numeric indication plus or minus 10% of that referenced numeric indication. For example, the term "about 4" would include a range of 3.6 to 4.4.

Fermentation is an anaerobic chemical process by which molecules such as glucose and xylose are broken down to release energy and fermentation end products are synthesized. Industrial fermentation processes begin with suitable microorganisms, such as yeasts and bacteria, and specified conditions, such as careful adjustment of nutrient concentration. The products are of many types: alcohols, glycerol, and carbon dioxide from yeast fermentation of various sugars; butyl alcohol, acetone, lactic acid, monosodium glutamate, and acetic acid from various bacteria; and citric acid, gluconic acid, and small amounts of antibiotics, vitamin B12, and riboflavin (vitamin B2) from mold fermentation. Ethyl alcohol and/or butanol are produced via the fermentation of starch or sugar and are important sources of liquid biofuel.

"Fermentive end-product" and "fermentation end-product" are used interchangeably herein to include biofuels, chemicals, compounds suitable as liquid fuels, gaseous fuels, triacylglycerols (TAGs), reagents, chemical feedstocks, chemical additives, processing aids, food additives, bioplastics and precursors to bioplastics, and other products. Examples of fermentive end-products include but are not limited to 1,4 diacids (succinic, fumaric and malic), 2,5 furan dicarboxylic acid, 3 hydroxy propionic acid, aspartic acid, glucaric acid, glutamic acid, itaconic acid, levulinic acid, 3-hydroxybutyrolactone, glycerol, sorbitol, xylitol/arabinitol, butanediol, butanol, methane, methanol, ethane, ethene, ethanol, n-propane, 1-propene, 1-propanol, propanal, acetone, propionate, n-butane, 1-butene, 1-butanol, butanal, butanoate, isobutanal, isobutanol, 2-methylbutanal, 2-methylbutanol, 3-methylbutanal, 3-methylbutanol, 2-butene, 2-butanol, 2-butanone, 2,3-butanediol, 3-hydroxy-2-butanone, 2,3-butanedione, ethylbenzene, ethenylbenzene, 2-phenylethanol, phenylacetaldehyde, 1-phenylbutane, 4-phenyl-1-butene, 4-phenyl-2-butene, 1-phenyl-2-butene, 1-phenyl-2-butanol, 4-phenyl-2-butanol, 1-phenyl-2-butanone, 4-phenyl-2-butanone, 1-phenyl-2,3-butandiol, 1-phenyl-3-hydroxy-2-butanone, 4-phenyl-3-hydroxy-2-butanone, 1-phenyl-2,3-butanedione, n-pentane, ethylphenol, ethenylphenol, 2-(4-hydroxyphenyl)ethanol, 4-hydroxyphenylacetaldehyde, 1-(4-hydroxyphenyl) butane, 4-(4-hydroxyphenyl)-1-butene, 4-(4-hydroxyphenyl)-2-butene, 1-(4-hydroxyphenyl)-1-butene, 1-(4-hydroxyphenyl)-2-butanol, 4-(4-hydroxyphenyl)-2-butanol, 1-(4-hydroxyphenyl)-2-butanone, 4-(4-hydroxyphenyl)-2-butanone, 1-(4-hydroxyphenyl)-2,3-butandiol, 1-(4-hydroxyphenyl)-3-hydroxy-2-butanone, 4-(4-hydroxyphenyl)-3-hydroxy-2-butanone, 1-(4-hydroxyphenyl)-2,3-butanonedione, indolylethane, indolylethene, 2-(indole-3-) ethanol, n-pentane, 1-pentene, 1-pentanol, pentanal, pentanoate, 2-pentene, 2-pentanol, 3-pentanol, 2-pentanone, 3-pentanone, 4-methylpentanal, 4-methylpentanol, 2,3-pentanediol, 2-hydroxy-3-pentanone, 3-hydroxy-2-pentanone, 2,3-pentanedione, 2-methylpentane, 4-methyl-1-pentene, 4-methyl-2-pentene, 4-methyl-3-pentene, 4-methyl-2-pentanol, 2-methyl-3-pentanol, 4-methyl-2-pentanone, 2-methyl-3-pentanone, 4-methyl-2,3-pentanediol, 4-methyl-2-hydroxy-3-pentanone, 4-methyl-3-hydroxy-2-pentanone, 4-methyl-2,3-pentanedione, 1-phenylpentane, 1-phenyl-1-pentene, 1-phenyl-2-pentene, 1-phenyl-3-pentene, 1-phenyl-2-pentanol, 1-phenyl-3-pentanol, 1-phenyl-2-pentanone, 1-phenyl-3-pentanone, 1-phenyl-2,3-pentanediol, 1-phenyl-2-hydroxy-3-pentanone, 1-phenyl-3-hydroxy-2-pentanone, 1-phenyl-2,3-pentanedione, 4-methyl-1-phenylpentane, 4-methyl-1-phenyl-1-pentene, 4-methyl-1-phenyl-2-pentene, 4-methyl-1-phenyl-3-pentene, 4-methyl-1-phenyl-3-pentanol, 4-methyl-1-phenyl-2-pentanol, 4-methyl-1-phenyl-3-pentanone, 4-methyl-1-phenyl-2-pentanone, 4-methyl-1-phenyl-2,3-pentanediol, 4-methyl-1-phenyl-2,3-pentanedione, 4-methyl-1-phenyl-3-hydroxy-2-pentanone, 4-methyl-1-phenyl-2-hydroxy-3-pentanone, 1-(4-hydroxyphenyl) pentane, 1-(4-hydroxyphenyl)-1-pentene, 1-(4-hydroxyphenyl)-2-pentene, 1-(4-hydroxyphenyl)-3-pentene, 1-(4-hydroxyphenyl)-2-pentanol, 1-(4-hydroxyphenyl)-3-pentanol, 1-(4-hydroxyphenyl)-2-pentanone, 1-(4-hydroxyphenyl)-3-pentanone, 1-(4-hydroxyphenyl)-2,3-pentanediol, 1-(4-hydroxyphenyl)-2-hydroxy-3-pentanone, 1-(4-hydroxyphenyl)-3-hydroxy-2-pentanone, 1-(4-hydroxyphenyl)-2,3-pentanedione, 4-methyl-1-(4-hydroxyphenyl) pentane, 4-methyl-1-(4-hydroxyphenyl)-2-pentene, 4-methyl-1-(4-hydroxyphenyl)-3-pentene, 4-methyl-1-(4-hydroxyphenyl)-1-pentene, 4-methyl-1-(4-hydroxyphenyl)-3-pentanol, 4-methyl-1-(4-hydroxyphenyl)-2-pentanol, 4-methyl-1-(4-hydroxyphenyl)-3-pentanone, 4-methyl-1-(4-hydroxyphenyl)-2-pentanone, 4-methyl-1-(4-hydroxyphenyl)-2,3-pentanediol, 4-methyl-1-(4-hydroxyphenyl)-2,3-pentanedione, 4-methyl-1-(4-hydroxyphenyl)-3-hydroxy-2-pentanone, 4-methyl-1-(4-hydroxyphenyl)-2-hydroxy-3-pentanone, 1-indole-3-pentane, 1-(indole-3)-1-pentene, 1-(indole-3)-2-pentene, 1-(indole-3)-3-pentene, 1-(indole-3)-2-pentanol, 1-(indole-3)-3-pentanol, 1-(indole-3)-2-pentanone, 1-(indole-3)-3-pentanone, 1-(indole-3)-2,3-pentanediol, 1-(indole-3)-2-hydroxy-3-pentanone, 1-(indole-3)-3-hydroxy-2-pentanone, 1-(indole-3)-2,3-pentanedione, 4-methyl-1-(indole-3-)pentane, 4-methyl-1-(indole-3)-2-pentene, 4-methyl-1-(indole-3)-3-pentene, 4-methyl-1-(indole-3)-1-pentene, 4-methyl-2-(indole-3)-3-pentanol, 4-methyl-1-(indole-3)-2-pentanol, 4-methyl-1-(indole-3)-3-pentanone, 4-methyl-1-(indole-3)-2-pentanone, 4-methyl-1-(indole-3)-2,3-pentanediol, 4-methyl-1-(indole-3)-2,3-pentanedione, 4-methyl-1-(indole-3)-3-hydroxy-2-pentanone, 4-methyl-1-(indole-3)-2-hydroxy-3-pentanone, n-hexane, 1-hexene, 1-hexanol, hexanal, hexanoate, 2-hexene, 3-hexene, 2-hexanol, 3-hexanol, 2-hexanone, 3-hexanone, 2,3-hexanediol, 2,3-hexanedione, 3,4-hexanediol, 3,4-hexanedione, 2-hydroxy-3-hexanone, 3-hydroxy-2-hexanone, 3-hydroxy-4-hexanone, 4-hydroxy-3-hexanone, 2-methylhexane, 3-methylhexane, 2-methyl-2-hexene, 2-methyl-3-hexene, 5-methyl-1-hexene, 5-methyl-2-hexene, 4-methyl-1-hexene, 4-methyl-2-hexene, 3-methyl-3-hexene, 3-methyl-2-hexene, 3-methyl-1-hexene, 2-methyl-3-hexanol, 5-methyl-2-hexanol, 5-methyl-3-hexanol, 2-methyl-3-hexanone, 5-methyl-2-hexanone, 5-methyl-3-hexanone, 2-methyl-3,4-hexanediol, 2-methyl-3,4-hexanedione, 5-methyl-2,3-hexanediol, 5-methyl-2,3-hexanedione, 4-methyl-2,3-hexanediol, 4-methyl-2,3-hexanedione, 2-methyl-3-hydroxy-4-hexanone, 2-methyl-4-hydroxy-3-hexanone, 5-methyl-2-hydroxy-3-hexanone, 5-methyl-3-hydroxy-2-hexanone, 4-methyl-2-hydroxy-3-hexanone, 4-methyl-3-hydroxy-2-hexanone, 2,5-dimethylhexane, 2,5-dimethyl-2-hexene, 2,5-dimethyl-3-hexene, 2,5-dimethyl-3-hexanol, 2,5-dimethyl-3-hexanone, 2,5-dimethyl-3,4-hexanediol, 2,5-dimethyl-3,4-hexanedione, 2,5-dimethyl-3-hydroxy-4-hexanone, 5-methyl-1-phenylhexane, 4-methyl-1-phenylhexane, 5-methyl-1-phenyl-1-hexene, 5-methyl-1-phenyl-2-hexene, 5-methyl-1-phenyl-3-hexene, 4-methyl-1-phenyl-1-hexene, 4-methyl-1-phenyl-2-hexene, 4-methyl-1-phenyl-3-hexene, 5-methyl-1-phenyl-2-hexanol, 5-methyl-1-phenyl-3-hexanol, 4-methyl-1-phenyl-2-hexanol, 4-methyl-1-phenyl-3-hexanol, 5-methyl-1-phenyl-2-hexanone, 5-methyl-1-phenyl-3-hexanone, 4-methyl-1-phenyl-2-hexanone, 4-methyl-1-phenyl-3-hexanone, 5-methyl-1-phenyl-2,3-hexanediol, 4-methyl-1-phenyl-2,3-hexanediol, 5-methyl-1-phenyl-3-hydroxy-2-hexanone, 5-methyl-1-phenyl-2-hydroxy-3-hexanone, 4-methyl-1-phenyl-3-hydroxy-2-hexanone, 4-methyl-1-phenyl-2-hydroxy-3-hexanone, 5-methyl-1-phenyl-2,3-hexanedione, 4-methyl-1-phenyl-2,3-hexanedione, 4-methyl-1-(4-hydroxyphenyl) hexane, 5-methyl-1-(4-hydroxyphenyl)-1-hexene, 5-methyl-1-(4-hydroxyphenyl)-2-hexene, 5-methyl-1-(4-hydroxyphenyl)-3-hexene, 4-methyl-1-(4-hydroxyphenyl)-1-hexene, 4-methyl-1-(4-hydroxyphenyl)-2-hexene, 4-methyl-1-(4-hydroxyphenyl)-3-hexene, 5-methyl-1-(4-hydroxyphenyl)-2-hexanol, 5-methyl-1-(4-hydroxyphenyl)-3-hexanol, 4-methyl-1-(4-hydroxyphenyl)-2-hexanol, 4-methyl-1-(4-hydroxyphenyl)-3-hexanol, 5-methyl-1-(4-hydroxyphenyl)-2-hexanone, 5-methyl-1-(4-hydroxyphenyl)-3-hexanone, 4-methyl-1-(4-hydroxyphenyl)-2-hexanone, 4-methyl-1-(4-hydroxyphenyl)-3-hexanone, 5-methyl-1-(4-hydroxyphenyl)-2,3-hexanediol, 4-methyl-1-(4-hydroxyphenyl)-2,3-hexanediol, 5-methyl-1-(4-hydroxyphenyl)-3-hydroxy-2-hexanone, 5-methyl-1-(4-hydroxyphenyl)-2-hydroxy-3-hexanone, 4-methyl-1-(4-hydroxyphenyl)-3-hydroxy-2-hexanone, 4-methyl-1-(4-hydroxyphenyl)-2-hydroxy-3-hexanone, 5-methyl-1-(4-hydroxyphenyl)-2,3-hexanedione, 4-methyl-1-(4-hydroxyphenyl)-2,3-hexanedione, 4-methyl-1-(indole-3-) hexane, 5-methyl-1-(indole-3)-1-hexene, 5-methyl-1-(indole-3)-2-hexene, 5-methyl-1-(indole-3)-3-hexene, 4-methyl-1-(indole-3)-1-hexene, 4-methyl-1-(indole-3)-2-hexene, 4-methyl-1-(indole-3)-3-hexene, 5-methyl-1-(indole-3)-2-hexanol, 5-methyl-1-(indole-3)-3-hexanol, 4-methyl-1-(indole-3)-2-hexanol, 4-methyl-1-(indole-3)-3-hexanol, 5-methyl-1-(indole-3)-2-hexanone, 5-methyl-1-(indole-3)-3-hexanone, 4-methyl-1-(indole-3)-2-hexanone, 4-methyl-1-(indole-3)-3-hexanone, 5-methyl-1-(indole-3)-2,3-hexanediol, 4-methyl-1-(indole-3)-2,3-hexanediol, 5-methyl-1-(indole-3)-3-hydroxy-2-hexanone, 5-methyl-1-(indole-3)-2-hydroxy-3-hexanone, 4-methyl-1-(indole-3)-3-hydroxy-2-hexanone, 4-methyl-1-(indole-3)-2-hydroxy-3-hexanone, 5-methyl-1-(indole-3)-2,3-hexanedione, 4-methyl-1-(indole-3)-2,3-hexanedione, n-heptane, 1-heptene, 1-heptanol, heptanal, heptanoate, 2-heptene, 3-heptene, 2-heptanol, 3-heptanol, 4-heptanol, 2-heptanone, 3-heptanone, 4-heptanone, 2,3-heptanediol, 2,3-heptanedione, 3,4-heptanediol, 3,4-heptanedione, 2-hydroxy-3-heptanone, 3-hydroxy-2-heptanone, 3-hydroxy-4-heptanone, 4-hydroxy-3-heptanone, 2-methylheptane, 3-methylheptane, 6-methyl-2-heptene, 6-methyl-3-heptene, 2-methyl-3-heptene, 2-methyl-2-heptene, 5-methyl-2-heptene, 5-methyl-3-heptene, 3-methyl-3-heptene, 2-methyl-3-heptanol, 2-methyl-4-heptanol, 6-methyl-3-heptanol, 5-methyl-3-heptanol, 3-methyl-4-heptanol, 2-methyl-3-heptanone, 2-methyl-4-heptanone, 6-methyl-3-heptanone, 5-methyl-3-heptanone, 3-methyl-4-heptanone, 2-methyl-3,4-heptanediol, 2-methyl-3,4-heptanedione, 6-methyl-3,4-heptanediol, 6-methyl-3,4-heptanedione, 5-methyl-3,4-heptanediol, 5-methyl-3,4-heptanedione, 2-methyl-3-hydroxy-4-heptanone, 2-methyl-4-hydroxy-3-heptanone, 6-methyl-3-hydroxy-4-heptanone, 6-methyl-4-hydroxy-3-heptanone, 5-methyl-3-hydroxy-4-heptanone, 5-methyl-4-hydroxy-3-heptanone, 2,6-dimethylheptane, 2,5-dimethylheptane, 2,6-dimethyl-2-heptene, 2,6-dimethyl-3-heptene, 2,5-dimethyl-2-heptene, 2,5-dimethyl-3-heptene, 3,6-dimethyl-3-heptene, 2,6-dimethyl-3-heptanol, 2,6-dimethyl-4-heptanol, 2,5-dimethyl-3-heptanol, 2,5-dimethyl-4-heptanol, 2,6-dimethyl-3,4-heptanediol, 2,6-dimethyl-3,4-heptanedione, 2,5-dimethyl-3,4-heptanediol, 2,5-dimethyl-3,4-heptanedione, 2,6-dimethyl-3-hydroxy-4-heptanone, 2,6-dimethyl-4-hydroxy-3-heptanone, 2,5-dimethyl-3-hydroxy-4-heptanone, 2,5-dimethyl-4-hydroxy-3-heptanone, n-octane, 1-octene, 2-octene, 1-octanol, octanal, octanoate, 3-octene, 4-octene, 4-octanol, 4-octanone, 4,5-octanediol, 4,5-octanedione, 4-hydroxy-5-octanone, 2-methyloctane, 2-methyl-3-octene, 2-methyl-4-octene, 7-methyl-3-octene, 3-methyl-3-octene, 3-methyl-4-octene, 6-methyl-3-octene, 2-methyl-4-octanol, 7-methyl-4-octanol, 3-methyl-4-octanol, 6-methyl-4-octanol, 2-methyl-4-octanone, 7-methyl-4-octanone, 3-methyl-4-octanone, 6-methyl-4-octanone, 2-methyl-4,5-octanediol, 2-methyl-4,5-octanedione, 3-methyl-4,5-octanediol, 3-methyl-4,5-octanedione, 2-methyl-4-hydroxy-5-octanone, 2-methyl-5-hydroxy-4-octanone, 3-methyl-4-hydroxy-5-octanone, 3-methyl-5-hydroxy-4-octanone, 2,7-dimethyloctane, 2,7-dimethyl-3-octene, 2,7-dimethyl-4-octene, 2,7-dimethyl-4-octanol, 2,7-dimethyl-4-octanone, 2,7-dimethyl-4,5-octanediol, 2,7-dimethyl-4,5-octanedione, 2,7-dimethyl-4-hydroxy-5-octanone, 2,6-dimethyloctane, 2,6-dimethyl-3-octene, 2,6-dimethyl-4-octene, 3,7-dimethyl-3-octene, 2,6-dimethyl-4-octanol, 3,7-dimethyl-4-octanol, 2,6-dimethyl-4-octanone, 3,7-dimethyl-4-octanone, 2,6-dimethyl-4,5-octanediol, 2,6-dimethyl-4,5-octanedione, 2,6-dimethyl-4-hydroxy-5-octanone, 2,6-dimethyl-5-hydroxy-4-octanone, 3,6-dimethyloctane, 3,6-dimethyl-3-octene, 3,6-dimethyl-4-octene, 3,6-dimethyl-4-octanol, 3,6-dimethyl-4-octanone, 3,6-dimethyl-4,5-octanediol, 3,6-dimethyl-4,5-octanedione, 3,6-dimethyl-4-hydroxy-5-octanone, n-nonane, 1-nonene, 1-nonanol, nonanal, nonanoate, 2-methylnonane, 2-methyl-4-nonene, 2-methyl-5-nonene, 8-methyl-4-nonene, 2-methyl-5-nonanol, 8-methyl-4-nonanol, 2-methyl-5-nonanone, 8-methyl-4-nonanone, 8-methyl-4,5-nonanediol, 8-methyl-4,5-nonanedione, 8-methyl-4-hydroxy-5-nonanone, 8-methyl-5-hydroxy-4-nonanone, 2,8-dimethyl-nonane, 2,8-dimethyl-3-nonene, 2,8-dimethyl-4-nonene, 2,8-dimethyl-5-nonene, 2,8-dimethyl-4-nonanol, 2,8-dimethyl-5-nonanol, 2,8-dimethyl-4-nonanone, 2,8-dimethyl-5-nonanone, 2,8-dimethyl-4,5-nonanediol, 2,8-dimethyl-4,5-nonanedione, 2,8-dimethyl-4-hydroxy-5-nonanone, 2,8-dimethyl-5-hydroxy-4-nonanone, 2,7-dimethylnonane, 3,8-dimethyl-3-nonene, 3,8-dimethyl-4-nonene, 3,8-dimethyl-5-nonene, 3,8-dimethyl-4-nonanol, 3,8-dimethyl-5-nonanol, 3,8-dimethyl-4-nonanone, 3,8-dimethyl-5-nonanone, 3,8-dimethyl-4,5-nonanediol, 3,8-dimethyl-4,5-nonanedione, 3,8-dimethyl-4-hydroxy-5-nonanone, 3,8-dimethyl-5-hydroxy-4-nonanone, n-decane, 1-decene, 1-decanol, decanoate, 2,9-dimethyldecane, 2,9-dimethyl-3-decene, 2,9-dimethyl-4-decene, 2,9-dimethyl-5-decanol, 2,9-dimethyl-5-decanone, 2,9-dimethyl-5,6-decanediol, 2,9-dimethyl-6-hydroxy-5-decanone, 2,9-dimethyl-5,6-decanedionen-undecane, 1-undecene, 1-undecanol, undecanal, undecanoate, n-dodecane, 1-dodecene, 1-dodecanol, dodecanal, dodecanoate, n-dodecane, 1-decadecene, n-tridecane, 1-tridecene, 1-tridecanol, tridecanal, tridecanoate, n-tetradecane, 1-tetradecene, 1-tetradecanol, tetradecanal, tetradecanoate, n-pentadecane, 1-pentadecene, 1-pentadecanol, pentadecanal, pentadecanoate, n-hexadecane, 1-hexadecene, 1-hexadecanol, hexadecanal, hexadecanoate, n-heptadecane, 1-heptadecene, 1-heptadecanol, heptadecanal, heptadecanoate, n-octadecane, 1-octadecene, 1-octadecanol, octadecanal, octadecanoate, n-nonadecane, 1-nonadecene, 1-nonadecanol, nonadecanal, nonadecanoate, eicosane, 1-eicosene, 1-eicosanol, eicosanal, eicosanoate, 3-hydroxy propanal, 1,3-propanediol, 4-hydroxybutanal, 1,4-butanediol, 3-hydroxy-2-butanone, 2,3-butandiol, 1,5-pentane diol, homocitrate, homoisocitorate, b-hydroxy adipate, glutarate, glutarsemialdehyde, glutaraldehyde, 2-hydroxy-1-cyclopentanone, 1,2-cyclopentanediol, cyclopentanone, cyclopentanol, (S)-2-acetolactate, (R)-2,3-Dihydroxy-isovalerate, 2-oxoisovalerate, isobutyryl-CoA, isobutyrate, isobutyraldehyde, 5-amino pentaldehyde, 1,10-diaminodecane, 1,10-diamino-5-decene, 1,10-diamino-5-hydroxydecane, 1,10-diamino-5-decanone, 1,10-diamino-5,6-decanediol, 1,10-diamino-6-hydroxy-5-decanone, phenylacetoaldehyde, 1,4-diphenylbutane, 1,4-diphenyl-1-butene, 1,4-diphenyl-2-butene, 1,4-diphenyl-2-butanol, 1,4-diphenyl-2-butanone, 1,4-diphenyl-2,3-butanediol, 1,4-diphenyl-3-hydroxy-2-butanone, 1-(4-hydeoxyphenyl)-4-phenylbutane, 1-(4-hydeoxyphenyl)-4-phenyl-1-butene, 1-(4-hydeoxyphenyl)-4-phenyl-2-butene, 1-(4-hydeoxyphenyl)-4-phenyl-2-butanol, 1-(4-hydeoxyphenyl)-4-phenyl-2-butanone, 1-(4-hydeoxyphenyl)-4-phenyl-2,3-butanediol, 1-(4-hydeoxyphenyl)-4-phenyl-3-hydroxy-2-butanone, 1-(indole-3)-4-phenylbutane, 1-(indole-3)-4-phenyl-1-butene, 1-(indole-3)-4-phenyl-2-butene, 1-(indole-3)-4-phenyl-2-butanol, 1-(indole-3)-4-phenyl-2-butanone, 1-(indole-3)-4-phenyl-2,3-butanediol, 1-(indole-3)-4-phenyl-3-hydroxy-2-butanone, 4-hydroxyphenylacetoaldehyde, 1,4-di(4-hydroxyphenyl)butane, 1,4-di(4-hydroxyphenyl)-1-butene, 1,4-di(4-hydroxyphenyl)-2-butene, 1,4-di(4-hydroxyphenyl)-2-butanol, 1,4-di(4-hydroxyphenyl)-2-butanone, 1,4-di(4-hydroxyphenyl)-2,3-butanediol, 1,4-di(4-hydroxyphenyl)-3-hydroxy-2-butanone, 1-(4-hydroxyphenyl)-4-(indole-3-)butane, 1-(4-hydroxyphenyl)-4-(indole-3)-1-butene, 1-di(4-hydroxyphenyl)-4-(indole-3)-2-butene, 1-(4-hydroxyphenyl)-4-(indole-3)-2-butanol, 1-(4-hydroxyphenyl)-4-(indole-3)-2-butanone, 1-(4-hydroxyphenyl)-4-(indole-3)-2,3-butanediol, 1-(4-hydroxyphenyl-4-(indole-3)-3-hydroxy-2-butanone, indole-3-acetoaldehyde, 1,4-di(indole-3-)butane, 1,4-di(indole-3)-1-butene, 1,4-di(indole-3)-2-butene, 1,4-di(indole-3)-2-butanol, 1,4-di(indole-3)-2-butanone, 1,4-di(indole-3)-2,3-butanediol, 1,4-di(indole-3)-3-hydroxy-2-butanone, succinate semialdehyde, hexane-1,8-dicarboxylic acid, 3-hexene-1,8-dicarboxylic acid, 3-hydroxy-hexane-1,8-dicarboxylic acid, 3-hexanone-1,8-dicarboxylic acid, 3,4-hexanediol-1,8-dicarboxylic acid, 4-hydroxy-3-hexanone-1,8-dicarboxylic acid, glycerol, fucoidan, iodine, chlorophyll, carotenoid, calcium, magnesium, iron, sodium, potassium, phosphate, lactic acid, acetic acid, formic acid, isoprenoids, and polyisoprenes, including rubber. Further, such products can include succinic acid, pyruvic acid, enzymes such as cellulases, polysaccharases, lipases, proteases, ligninases, and hemicellulases and may be present as a pure compound, a mixture, or an impure or diluted form.

Fermentation end-products can also include polyols or sugar alcohols; for example, methanol, glycol, glycerol, erythritol, threitol, arabitol, xylitol, ribitol, mannitol, sorbitol, dulcitol, fucitol, iditol, inositol, volemitol, isomalt, maltitol, lactitol, and/or polyglycitol.

The term "pH modifier" as used herein has its ordinary meaning as known to those skilled in the art and can include any material that will tend to increase, decrease or hold steady the pH of the broth or medium. A pH modifier can be an acid, a base, a buffer, or a material that reacts with other materials present to serve to raise, lower, or hold steady the pH. In one embodiment, more than one pH modifier can be used, such as more than one acid, more than one base, one or more acid with one or more bases, one or more acids with one or more buffers, one or more bases with one or more buffers, or one or more acids with one or more bases with one or more buffers. In one embodiment, a buffer can be produced in the broth or medium or separately and used as an ingredient by at least partially reacting in acid or base with a base or an acid, respectively. When more than one pH modifiers are utilized, they can be added at the same time or at different times. In one embodiment, one or more acids and one or more bases are combined, resulting in a buffer. In one embodiment, media components, such as a carbon source or a nitrogen source serve as a pH modifier; suitable media components include those with high or low pH or those with buffering capacity. Exemplary media components include acid- or base-hydrolyzed plant polysaccharides having residual acid or base, ammonia fiber explosion (AFEX) treated plant material with residual ammonia, lactic acid, corn steep solids or liquor.

The term "plant polysaccharide" as used herein has its ordinary meaning as known to those skilled in the art and can comprise one or more polymers of sugars and sugar derivatives as well as derivatives of sugar polymers and/or other polymeric materials that occur in plant matter. Exemplary plant polysaccharides include cellulose, starch, pectin, and hemicellulose. Others are chitin, sulfonated polysaccharides such as alginic acid, agarose, carrageenan, porphyran, furcelleran and funoran. Generally, the polysaccharide can have two or more sugar units or derivatives of sugar units. The sugar units and/or derivatives of sugar units can repeat in a regular pattern, or otherwise. The sugar units can be hexose units or pentose units, or combinations of these. The derivatives of sugar units can be sugar alcohols, sugar acids, amino sugars, etc. The polysaccharides can be linear, branched, cross-linked, or a mixture thereof. One type or class of polysaccharide can be cross-linked to another type or class of polysaccharide. The concentration of saccharides in a biomass containing plant polysaccharides such as cellulose, hemicellulose, starch, or pectin can be given in terms of monosaccharide equivalents. A monosaccharide equivalent concentration is the concentration of saccharides assuming complete hydrolysis of polysaccharides to monosaccharides.

The term "saccharification" as used herein has its ordinary meaning as known to those skilled in the art and can include conversion of plant polysaccharides to lower molecular weight species that can be utilized by the organism at hand. For some organisms, this would include conversion to monosaccharides, disaccharides, trisaccharides, and oligosaccharides of up to about seven monomer units, as well as similarly sized chains of sugar derivatives and combinations of sugars and sugar derivatives.

The term "biomass" as used herein has its ordinary meaning as known to those skilled in the art and can include one or more biological materials that can be converted into a biofuel, chemical or other product. Biomass as used herein is synonymous with the term "feedstock" and includes corn syrup, molasses, silage, agricultural residues (corn stalks, grass, straw, grain hulls, fibers, bagasse, etc.), animal waste (manure from cattle, poultry, and hogs), Distillers Dried Solubles (DDS), Distillers Dried Grains (DDG), Condensed Distillers Solubles (CDS), Distillers Wet Grains (DWG), Distillers Dried Grains with Solubles (DDGS), woody materials (wood or bark, sawdust, timber slash, and mill scrap), municipal waste (waste paper, recycled toilet papers, yard clippings, etc.), and energy crops (poplars, willows, switchgrass, *Miscanthus* sp., alfalfa, prairie bluestem, algae, including macroalgae, etc.). One exemplary source of biomass is plant matter. Plant matter can be, for example, woody plant matter, including softwoods or hardwoods, non-woody plant matter, cellulosic material, lignocellulosic material, hemicellulosic material, carbohydrates, pectin, starch, inulin, fructans, glucans, corn, sugar cane, grasses such as rice, corn, barley, wheat, switchgrass, sorghum, high biomass sorghum, bamboo or the like, algae and material derived from these. Plants can be in their natural state or genetically modified, e.g., to increase the cellulosic or hemicellulosic portion of the cell wall, or to produce additional exogenous or endogenous enzymes to increase the separation of cell wall components. Plant matter can also include plant cell culture or plant cell tissue culture. Plant matter can be further described by reference to the chemical species present, such as proteins, polysaccharides and oils. Polysaccharides include polymers of various monosaccharides and derivatives of monosaccharides including glucose, fructose, lactose, galacturonic acid, rhamnose, etc. Plant matter also includes agricultural waste byproducts or side streams such as pomace, corn steep liquor, corn steep solids, distillers grains, peels, pits, fermentation waste, straw, lumber, sewage, garbage and food leftovers. Peels can be citrus which include, but are not limited to, tangerine peel, grapefruit peel, orange peel, tangerine peel, lime peel and lemon peel. These materials can come from farms, forestry, industrial sources, households, etc. Another non-limiting example of biomass is animal matter, including, for example milk, meat, fat, animal processing waste, and animal waste. "Feedstock" is frequently used to refer to biomass being used for a process, such as those described herein.

Biomass can be derived from agricultural crops, crop residues, trees, woodchips, sawdust, paper, cardboard, grasses, algae, municipal waste and other sources as described supra. In one embodiment, the biomass contains cellulosic, hemicellulosic, and/or lignocellulosic material. In one embodiment the biomass is woody (e.g., poplar, *Eucalyptus*, willow, pine.). In another embodiment, the biomass is non-woody plant material, such as grasses, dicots, and monocots. Other biomasses include algal biomass, nonvascular plant biomass, and processed materials derived from plants; e.g., hulls, distiller's grains, municipal sewage waste, and the like.

In one embodiment, a biomass composition comprising cellulose, hemicellulose, and/or lignocellulose comprises alfalfa, algae, bagasse, bamboo, corn stover, corn cobs, corn fiber, corn kernels, corn mash, corn steep liquor, corn steep solids, distiller's grains, distiller's dried solubles, distiller's dried grains, condensed distiller's solubles, distiller's wet grains, distiller's dried grains with solubles, *eucalyptus*, food waste, fruit peels, garden residue, grass, grain hulls, modified crop plants, municipal waste, oat hulls, paper, paper pulp, prairie bluestem, poplar, rice hulls, seed hulls, silage, sorghum, straw, sugarcane, switchgrass, wheat, wheat straw, wheat bran, de-starched wheatbran, willows, wood, plant cells, plant tissue cultures, tissue cultures, or a combination thereof.

The term "dry weight" of biomass is meant the weight of the biomass having all or essentially all water removed. Dry weight is typically measured according to American Society for Testing and Materials (ASTM) Standard El 756-01 (Standard Test method for Determination of Total Solids in Biomass) or Technical Association of the Pulp and Paper Industry, Inc. (TAPPI) Standard T-412 om-02 (Moisture in Pulp, Paper and Paperboard).

The term "productivity" as used herein has its ordinary meaning as known to those skilled in the art and can include the mass of a material of interest produced in a given time in a given volume. Units can be, for example, grams per liter-hour, or some other combination of mass, volume, and time. In fermentation, productivity can be used to characterize how fast a product can be made within a given fermentation volume. The volume can be referenced to the total volume of the fermentation vessel, the working volume of the fermentation vessel, or the actual volume of broth being fermented. The context of the phrase will indicate the meaning intended to one of skill in the art. Productivity is different from "titer" in that productivity includes a time term, and titer is analogous to concentration. Titer and Productivity can generally be measured at any time during the fermentation, such as at the beginning, the end, or at some intermediate time, with titer relating the amount of a particular material present or produced at the point in time of interest and the productivity relating the amount of a particular material produced per liter in a given amount of time. The amount of time used in the productivity determination can be from the beginning of the fermentation or from some other time, and go to the end of the fermentation, such as when no additional material is produced or when harvest occurs, or some other time as indicated by the context of the use of the term. "Overall productivity" can refer to the productivity determined by utilizing the final titer and the overall fermentation time.

The term "biocatalyst" as used herein has its ordinary meaning as known to those skilled in the art and can include one or more enzymes and/or microorganisms, including solutions, suspensions, and mixtures of enzymes and microorganisms. In some contexts, this word will refer to the possible use of either enzymes or microorganisms to serve a particular function, in other contexts the word will refer to the combined use of the two, and in other contexts the word will refer to only one of the two. The context of the phrase will indicate the meaning intended to one of skill in the art. For example, a biocatalyst can be a fermenting microorganism. The term biocatalyst includes fermenting microorganisms such as yeast, bacteria, or algae.

The terms "conversion efficiency" or "yield" as used herein have their ordinary meaning as known to those skilled in the art and can include the mass of product made from a mass of substrate. The term can be expressed as a percentage yield of the product from a starting mass of substrate. For the production of ethanol from glucose, the net reaction is generally accepted as:

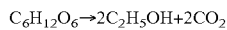

$$C_6H_{12}O_6 \rightarrow 2C_2H_5OH + 2CO_2$$

and the theoretical maximum conversion efficiency, or yield, is 51% (wt.). Frequently, the conversion efficiency will be referenced to the theoretical maximum, for example, "80% of the theoretical maximum." In the case of conversion of glucose to ethanol, this statement would indicate a conversion efficiency of 41% (wt.). The context of the phrase will indicate the substrate and product intended to one of skill in the art.

"Pretreatment" or "pretreated" is used herein to refer to any mechanical, chemical, thermal, biochemical process or combination of these processes whether in a combined step or performed sequentially, that achieves disruption or expansion of the biomass so as to render the biomass more susceptible to attack by enzymes and/or microbes. In one embodiment, pretreatment includes removal or disruption of lignin so as to make the cellulose and hemicellulose polymers in the plant biomass more available to cellulolytic enzymes and/or microbes, for example, by treatment with acid or base. In one embodiment, pretreatment includes disruption or expansion of cellulosic and/or hemicellulosic material. Chemical pretreatment processes include, but are not limited to, bleaching, oxidation, reduction, acid treatment, base treatment, sulfite treatment, acid sulfite treatment, basic sulfite treatment, ammonia treatment, and hydrolysis. Thermal pretreatment processes include, but are not limited to, sterilization, ammonia fiber expansion or explosion ("AFEX"), steam explosion, holding at elevated temperatures, pressurized or unpressurized, in the presence or absence of water, and freezing. Biochemical processes include, but are not limited to, treatment with enzymes, including enzymes produced by genetically-modified plants, and treatment with microorganisms. Various enzymes that can be utilized include cellulase, amylase, β-glucosidase, xylanase, gluconase, and other polysaccharases; lysozyme; laccase, and other lignin-modifying enzymes; lipoxygenase, peroxidase, and other oxidative enzymes; proteases; and lipases. One or more of the mechanical, chemical, thermal, thermochemical, and biochemical processes can be combined or used separately. Such combined processes can also include those used in the production of paper, cellulose products, microcrystalline cellulose, and cellulosics and can include pulping, Kraft pulping, acidic sulfite processing. The feedstock can be a side stream or waste stream from a facility that utilizes one or more of these processes on a biomass material, such as cellulosic, hemicellulosic or lignocellulosic material. Examples include paper plants, cellulosics plants, distillation plants, cotton processing plants, and microcrystalline cellulose plants. The feedstock can also include cellulose-containing or cellulosic containing waste materials. The feedstock can also be biomass materials, such as wood, grasses, corn, starch, or saccharide, produced or harvested as an intended feedstock for production of ethanol or other products such as by biocatalysts.

Pretreatment of the biomass composition can be performed such that any solids are reduced in size. Reducing the size of solids in the biomass composition can be advantageous because smaller particles have larger surface area to volume ratios. Increasing the ratio of surface area to volume can be advantageous because it can, for example, increase the rate of particle wetting (e.g., with water or a chemical agent such as an acid or a base), increase the accessibility of enzymes to the polysaccharides in the biomass, enable the use of a smaller dose of enzymes during a hydrolysis of the biomass, enable the use of fewer or lower amounts of chemicals (e.g., acids or bases) during a pretreatment and/or hydrolysis step, enable the use of weaker acids or bases or ionic liquids in a pretreatment or hydrolysis step, enable the use of higher concentrations of solids in any further processing step (e.g., during a hydrolysis step), and/or increase the yield of saccharides from the hydrolysis of the biomass.

Biomass compositions can be reduced in size to a mixture of particles having a uniform, or substantially uniform, size. Such mixtures can be referred to as homogeneous mixtures. Homogeneous mixtures of particles can have many advantages over mixtures of particles having heterogeneous sizes with respect to further pretreatment processes and/or during hydrolysis to produce saccharide streams. For example, heterogeneous mixtures of particles can experience uneven heating during thermal and thermochemical processing steps. Uneven heating can lead to overcooking (e.g., charring/burning) of particles and/or undercooking of particles. Charring or burning of particles can reduce the yield of saccharide from the hydrolysis of the particles; this can be due to degradation or denaturation of saccharide polymers such as starch, hemicellulose, cellulose. Undercooking of particles can lead to unhydrolyzed saccharide polymers (e.g., starch, hemicellulose, cellulose) during enzymatic or chemical hydrolysis, which can also reduce the yield of saccharide. In contrast, uniform heating, wetting, chemical treatment (e.g., acid or base treatment), and/or enzyme hydrolysis can be achieved with mixtures of particles having uniform sizes (e.g., homogeneous mixtures).

"Sugar compounds", "sugar streams", "saccharide compounds", or "saccharide streams" is used herein to indicate mostly monosaccharide sugars, dissolved, crystallized, evaporated, or partially dissolved, including but not limited to hexoses and pentoses; sugar alcohols; sugar acids; sugar amines; compounds containing two or more of these linked together directly or indirectly through covalent or ionic bonds; and mixtures thereof. Included within this description are disaccharides; trisaccharides; oligosaccharides; polysaccharides; and sugar chains, branched and/or linear, of any length. A sugar stream can consist of primarily or substantially C6 sugars, C5 sugars, or mixtures of both C6 and C5 sugars in varying ratios of said sugars. C6 sugars have a six-carbon molecular backbone and C5 sugars have a five-carbon molecular backbone. The terms "sugar" and "saccharide" are used interchangeably herein.

A "liquid" or "aqueous" composition may contain solids and a "solids" composition may contain liquids. A liquid composition refers to a composition in which the material is primarily liquid, and a solids composition is one in which the material is primarily solid.

The term "kPa" refers to kilopascal, a unit of pressure. Standard atmospheric pressure, the pressure exerted by a 10 g mass resting on a 1 $cm^2$ area, is defined as 101.325 kPa. The term "psi" or "PSI" refers to pound-force per square inch. It is the pressure resulting from a force of one pound-force applied to an area of one square inch.

DESCRIPTION

The following description and examples illustrate some exemplary embodiments of the disclosure in detail. Those of skill in the art will recognize that there are numerous variations and modifications of this disclosure that are encompassed by its scope. Accordingly, the description of a certain exemplary embodiment should not be deemed to limit the scope of the present disclosure.

Disclosed herein are methods for efficient, rapid treatment of biomass using high biomass concentration conditions. Unlike present methods, which retain biomass materials in a chamber for a long period of time, it has been discovered that pre-processing of these materials can avoid long retention times under thermal and chemical treatment, thereby avoiding the degradation of C5 sugars, proteins and lignins into undesirable products such as hydroxymethyl furfural (HMF) and furfurals, while allowing the separation of carbohydrate materials, both monomeric and polymeric sugars, from other biomass components. The inhibitors usually formed during pretreatment include acetic acid (formed during the release of C5 sugars) and also formic acid, furfural and HMF. Formation of the latter three compounds is largely dependent on the temperature, pressure and biomass residence time during pretreatment.

Further, it has been discovered that the solubilization of crystalline cellulose is not impeded by the short exposure time. The methods provided herein also allow biomass to be heated and pressurized uniformly for improved access of treatment reactants to the biomass. During this process, concentrated masses (plugs) can be produced that can shear the biomass into smaller particles and can further increase access of reactants to hydrolyze and release the C5 polymers while also releasing and solubilizing the C6 polymers. In one embodiment, the biomass is moved through a reaction zone wherein steam and pressure are applied, followed by the addition of acid, and finally release of the material to atmospheric pressure by a rapidly opening and closing an end valve. The whole process can happen within seconds, resulting in a thermo-mechanically and/or chemically-hydrolyzed biomass with lower or reduced levels of inhibitors as compared to pretreatment methods known in the art.

In one embodiment, there is the establishment of a high pressure zone in a reactive extruder upstream of a pressurized reaction zone. The conveying elements within the extruder can effectively move biomass toward a specialized arrangement of screw elements that is configured to allow for a relative velocity drop and material accumulation, thereby creating a very high pressure zone just prior to the start of the reaction zone. The specialized arrangement of the screw elements resulting in the high pressure zone can be feedstock-dependent. In some embodiments, the high pressure zone is impermeable to steam, which can have a number of benefits.

High Pressure Zone Formation—The pressures achieved within this zone can allow for direct injection of steam and aids in directional flow, facilitate turbulence and intimate mixing of a 1-3-phase system, and keep the steam from backflowing (flowing upstream) to the extruder feed, thereby maintaining elevated pressure and temperature in the reaction zone. A dilute acid (or possibly base, or possibly an ionic liquid or another chemical reactant) can also be added in the reaction zone to speed up the conversion process. Further, the high pressure zone that is formed can keep the reactive material in the reaction zone, allowing for a less expensive, more durable metal to be used for the manufacture of the barrel liners and screw elements in the conveying zone. Examples of such materials include ceramics, glass, aluminum, hastelloy, titanium, through-hardened tool steel, abrasion-resistant metals manufactured via HIP process (Hot Isostatic Pressing), and the like.

The direct steam injection can allow for a rapid and uniform heating of the biomass, greatly assisted by the high surface area created by the small, uniform particle size. The combination of high temperature, intimate mixing, small particle size, high surface area and even distribution of reactive solutions (dilute acid, ionic liquid, etc.) can facilitats fast thermal and mass transfer and a rapid pretreatment process that produces low inhibitors.

Tying the formation of the high pressure zone with the outlet valve described infra closes the loop on the actual formation of a high pressure reactive zone within the extruder. High pressures in the reaction zone have been attained from 1 psi to 800 psi, and even over 1000 psi without backflow of the steam through the high pressure zone.

A "steam impervious plug" as described herein can refer to a highly concentrated plug formed by compacting the biomass, through which steam at a pressure of at least about 500 psi, at least about 600 psi, at least about 700 psi, at least about 800 psi, at least about 900 psi, or at least about 500 psi, is not able to premeat. In some embodiments, the steam impervious plug can be maintained continuously for at least about 1 hr, at least about 2 hrs, at least about 4 hrs, at least about 5 hrs, at least about 6 hrs, at least about 8 hrs, at least about 10 hrs, at least about 12 hrs, at least about 13 hrs, at least about 14 hrs, at least about 15 hrs, at least about 16 hrs, at least about 17 hrs, or at least about 18 hrs. In some embodiments, the steam impervious plug formed according to the methods and systems described herein can be maintained continuously while the biomass feeding rate is in a range from about 60 to about 350 dry kg/hr.

In one embodiment, the mechanical grinding of biomass in a high pressure zone creates a material that is very amenable for further pretreatment such as exposure to chemical reagents, pressure and/or heat. The small homogeneous particle size can allow for rapid pretreatment of the biomass under less severe conditions, yielding a high sugar conversion with a low inhibitor production. The particle downsizing can also speed up the subsequent enzymatic hydrolysis and other further processing.

In another embodiment, the size of the particles can be controlled by the combination of the screw elements and the speed at which the motor and the screw elements work together. Thus an optimal size can be produced depending on the type of biomass moving through the extruder and the kind of pretreatment required in the high pressure reaction zone.

In some cases, the pretreatment methods provided herein permit the release and depolymerization of sugars in a rapid time frame. The sugars can be released and depolymerized within a very short period of time. The period of time can be less than 1 minute. The period of time can be less than 20 seconds. Generally, the time in the reaction zone can range from a second to less than 20 seconds, preferably less than 10 seconds, but ultimately less than 1 minute. This provides continuously moving biomass through the barrel tube resulting in a rapidly-pretreated biomass containing few, no, or substantially no inhibitors.

Described herein are improved, low cost, energy-efficient pretreatment devices and methods for the rapid processing of lignocellulose, cellulose, hemicellulose, and the like biomass materials prior to enzymatic hydrolysis, which includes a thermo-mechanical treatment with or without chemicals and a reaction extrusion controlled by a high pressure zone and a pressure-driven variable end valve. The methods disclosed herein can include the use of a device that comprises a cylindrical chamber divided into tubular zones, wherein biomass can be moved either continuously or in batches through the cylindrical chamber; reduced in size; and treated with pressure, heat, chemicals, or a combination thereof in the different tubular zones prior to being subjected to a rapid difference in temperature and pressure (e.g., explosive decompression). The biomass can be moved by screw-type mechanism, such as a single, twin, or even triple screw as found in an extruder. Alternatively, the biomass can be moved by a mechanism such as a block or other mechanical pressure, differential hydrostatic pressure managed by air, oil, piston, vacuum, or gravity. These mechanisms can also have a function for pushing or driving forward or separating the biomass into chambers or zones for particular treatment or addition of materials.

In some embodiments, an extruder for use in the systems provided herein includes an elongated barrel presenting a material inlet and a material outlet adjacent opposed ends thereof, respectively, with one or more elongated, axially rotatable screw(s) within the barrel which serves to advance the material from the inlet end to the outlet end thereof. The one or more screws are turned by a drive shaft coupled to a motor. The screw can be designed to smooth the flow of material while reducing it in size and various screw elements can be arranged to increase or decrease the flow, sizing, mixing, or to form plugs of the biomass within the barrel. The screw(s) coupled with an end valve under pressure at the outlet can control the speed, pressure, and partly the temperature applied to the biomass as it moves through and out of the barrel.

The systems and methods disclosed herein can be used for industrial scale pretreatment of biomass at a high rate of throughput. For example, it is estimated that biomass can move through and be processed in accordance with the following Table 1 by continuous operation of a twin screw extruder in accordance with some of the methods disclosed herein.

TABLE 1

| Screw Diameter | Dry Matter Throughput Dry Tons/Day |
|---|---|
| 30 mm | 3.3 |
| 52 mm | 17.0 |
| 92 mm | 94.4 |
| 124 mm | 231.1 |

In a general overview, the apparatus and its use in an extruder are described as follows. The barrel screw reactor can comprise a metal cylindrical barrel (which can be lined with specialty materials such as ceramic, glass, aluminum, hastelloy, titanium, through-hardened tool steel, abrasion-resistant metals manufactured via HIP process (Hot Isostatic Pressing), and the like) having a size that can range from, e.g., 30 mm to 220 mm diameter or larger equipped with one or more screws, oriented horizontally or vertically. The barrel can be divided into separate sections and can be equipped with multiple use ports along the top, side, and/or bottom surfaces. Such multiple use ports can be sealable ports. The multiple use ports can allow the injection of water, steam, acid or other chemicals. The multiple use ports can allow the insertion of thermocouples and/or pressure gauges for measurement of temperature and pressure inside the barrel. Additional ports can be added as required. The reactor barrel can be equipped with electric heating elements or a steam jacket for even heating of the barrel. Heating can alternatively or additionally be supplied by the injection of steam. Alternatively, or in addition to a heating device or method, a cooling jackets or a heating/cooling system can be supplied or built into the system to quench reactions and control reaction temperatures. In another embodiment, both cooling devices/methods and one or more injections of fluids (such as water) in the reaction zone can be used to quench reactions and control the relative release of monosaccharides. Cooling can also be accomplished by varying pressure.

The reactor barrel can be attached to a pipe that discharges into a flash tank or other container. The flash tank can be constructed using stainless steel. The barrel can be isolated from the flash tank by a pipe with a seat end having a pressure actuated discharge valve arrangement capable of continuously adjusting position depending upon the back pressure on the valve and the pressure within the system. The discharge valve arrangement can comprise a metal or ceramic sealing seat in between to allow for an explosive discharge of biomass. Other materials can be used as well. The pressure actuated valve arrangement can comprise a conical nozzle connected to a shaft (see in FIGS. 1 and 2). The diameter of the end valve can vary with the size of the machine, and typically range from 30 mm to 220 mm or larger. The conical nozzle can be connected to a shaft that is attached to an actuator in a backpressure generator. The actuator can provide the pneumatic pressure that is regulated by the backpressure generator, which monitors the pressure. The pressure can be a high pressure such that no backflow occurs and there is a restricted flow of material out of the tube. The backpressure on the conical nozzle and seat can be adjustable. For example, operations can be performed using 50 psi to 600 psi (gauge pressure) or higher of backpressure onto the shaft connected to the conical nozzle of the end shear valve. The cone of the end shearing valve can travel between a fully closed and a fully open position, and any intermediate position. In normal practice, however, there is always an small annular space for material to exit as a safety feature. A pipe at the outlet of the end shear valve can direct the treated solids down into the bottom of the flash tank, where the solids and vapor can be separated and easily removed.

FIG. 1 shows an embodiment of one type of a design of a reactor as provided herein. The reactor can be a commercial scale reactor. It comprises a horizontal cylindrical barrel 31 fitted with twin screws (not shown) and a discharge valve 17 attached at a special end flange 14 at the second end of the barrel. The barrel can be insulated and can have impermeable walls. A motor 24 for moving the screws via a drive shaft can be attached near the first end. The motor can be, e.g., an electrically-driven motor and gearbox combination, with or without pulleys and V-belts or any other mechanism to turn the screws. The motor can also be, for example and without being limited, a synchronous torque motor. A hopper 20 can be attached to the inlet of the sealed end of the barrel 31. Biomass can be added through the opening of the hopper 20. The biomass can be any biomass as provided herein. There can be a feeder for non-compacting or compacting flow generation (not shown) such as a crammer to control biomass addition from the hopper 20 to the barrel 31. The compacting and/or non-compacting feeder can be any compacting and/or non-compacting loader known in the art. For example, a non-compacting flow inducing feeder can be a non-compacting feeder or various types of live-bottom bin flow inducers followed by flow metering conveyors such as various types of drag chains, bucket elevators, or rotating helixes. In its simplest form a non-compacting feeder can refer to loading biomass by hand into an open first end of the cylindrical barrel. Compacting feeders can comprise mechanical compaction. Mechanical compaction can be achieved by provision of a mechanical compaction device such as a reciprocating plunger or screw feeder. The barrel 31 can have a first sealable port 29 for adding water to hydrate the biomass in the tube as it moves away from the hopper end. The screws can be designed with sections to form a high-shear and high-pressure plug P1, which can occur after the optional addition of water but prior to the addition of steam through the ports 32 and 33. Plug P1 is configured to have a high shear, and to have a high pressure to become impervious to steam. Movement through the high shear plug P1 can break the biomass into smaller-sized particles (e.g., of about 10 to 200 microns). Further, because the plug P1 is impervious to steam and the pressure within the plug is high (e.g., about 1000 psi or higher), there is no backflow and the pressure in the reaction zone R1 is maintained throughout the reaction zone R1. This is in contrast to the plugs described in U.S. Pat. No. 8,328,947, that are permeable to steam and cannot maintain such a pressure differential. Further, as provided herein, there is no need to use a plug or compacted area to dewater the feedstock prior to its movement into the reaction zone, as required in U.S. Pat. Nos. 8,328,947, 5,232,649, or PCT Publ. No. WO2016/128224 A1. In some embodiments, the high pressure nature of plug P1 can be attributed to the small particle size of the material moving through P1 and/or the combination of screw elements causing the reverse flow and/or kneading.

Figure 14:
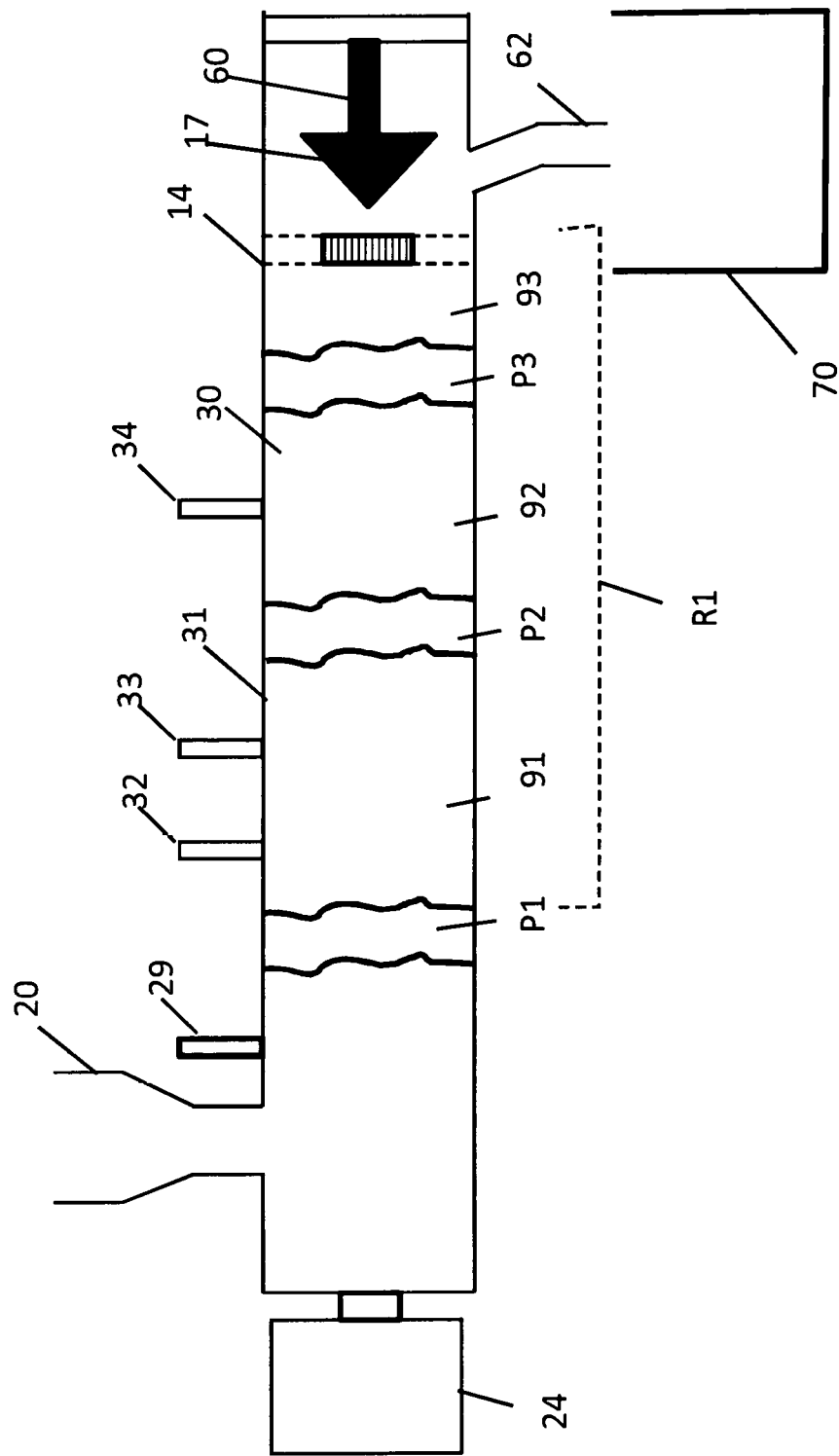
FIG. 14 is a schematic diagram of one embodiment of an apparatus with an impermeable and two permeable plugs disclosed herein.

Other plugs such as P2 and P3 can be formed as required in the reaction zone R1 using different configurations of the screws, as shown in FIG. 14. The plugs that are formed in the reaction zone R1 can separate the biomass into sections or zones that can be treated differently from one another. The nature of the high pressure plug P1 is different from that of P2 and P3. P1 can be a compacted area of the highest pressure. The subsequent "plugs", e.g., P2 and P3, formed in the reaction zone can be of lower pressure and can be configured to assist in the intimate mixing of a 3-phase system. The subsequent plug, e.g., P2 and P3, can be permeable to the steam, thus the pressure can remain substantially the same between the upstream and downstream sections of the reaction zone that are divided by the plugs therein.

Movement of the screws through the impermeable barrel chamber 30 pushes the biomass and water mixture from the feeder zone into the reaction zone 91. The residence time in the reaction zone can be controlled by varying the biomass feed rate and/or motor speed that moves the drive shafts. Ports 32, 33 add pressurized steam (e.g., to about 300 psi to 600 psi) to the barrel after the high pressure plug P1 is formed, increasing the barrel pressure to a desired temperature and pressure (for example, 600 psi and a temperature of 253° C.). The aqueous acid (or other chemical, e.g., a base) addition through port 34 solubilizes and hydrolyzes C6 polymers and/or C5 polymers into monosaccharides or monosaccharides and some remaining polymers, depending on the thermo-mechanical conditions maintained in this reaction zone R1. As the biomass moves through the cylindrical barrel chamber 30, more water can be added through another port (not shown).

If needed, a second plug P2 can be formed prior to the addition of aqueous chemical, e.g., acid, and can separate the material into a second zone 92, as shown in FIG. 14. In this second zone, C6 polymers can be solubilized and/or C5 polymers can be hydrolyzed into monosaccharides. Following the aqueous chemical addition through 34, a third plug P3, if required, can be formed as the biomass moves through the cylindrical barrel chamber 30. The chemical solution can also be added after the third plug is formed. Further solubilization of sugars can occur in this third zone 93 and, if needed, more water can be added through another port (not shown) in the third zone 93.

The end valve 17 comprises a part of the reaction zone R1. The end valve can be under constant pressure. A back pressure regulator (e.g., see FIGS. 11 and 12) can be added to the barrel cylinder 31 such that the back-pressure regulator monitors the pressure at the end of the zone R1. The monitoring can be continuous. The back pressure regulator acts to maintain a set pressure by opening and closing the end valve (e.g., on a continuous basis) 17 through a shaft 60 connected to an actuator (e.g., see FIGS. 12 and 13). The actuator can be any actuator as provided herein. For example, the actuator can be a pneumatic actuator. The valve activity can occur rapidly to open the end valve 17 and release pressurized material into a pipe 62 that leads to the open flash tank 70, thus blowing out the treated biomass and rapidly dropping the temperature and pressure from several hundred psi to atmospheric pressure. As the pressure drops, the back pressure regulator causes the actuator to close the end valve 17 via movement of the shaft 60. The pressure differential can be varied depending on the amount needed to further solubilize the C5 and/or C6 sugars. When operating at ideal conditions, the end valve 17 can never be completely closed and never be completely open, the shaft 60 moving back and forth under the control of the actuator.

In some cases, any device as provided herein comprises an actuator. The actuator can be controlled by a regulator. The actuator on a device as provided herein can be any type of mechanical, electro-mechanical, linear, piezoelectric, ultrasonic, hydraulic, electrohydraulic, pneumatic, segmented spindle, moving coil, or moving iron controllable actuator or motor known in the art. In some cases, the actuator in a device as provided herein comprises a pneumatic actuator. The pneumatic actuator can be a piston actuator. In some embodiments, the actuator in a device as provided herein comprises a hydraulic actuator. Examples of mechanical actuators can include, screw type actuators (e.g., leadscrew, screw jack, ball screw, or roller screw), wheel and axle (e.g., hoist, winch, rack and pinion, chain drive, belt drive, rigid chain, or rigid belt), piston actuators, diaphragm actuators, or cam actuators. A regulator for controlling an actuator in any device as provided herein can be a pressure regulator. The pressure regulator can be a back-pressure regulator. The pressure regulator (e.g., back-pressure regulator) can be a single stage regulator or double stage regulator. The pressure regulator can comprise a restricting element, a loading element, and a measuring element. The restricting element can be a variable orifice valve such as a globe, butterfly or poppet valve. For precise control, a valve such as a linear globe can work well. Others types of valves can be a fast-opening globe, a ball, a butterfly, or an equal percentage globe valve.

The loading element can be a weight, a spring, or an actuator (e.g., piston or diaphragm actuator) in combination with a spring. In some cases, the pressure regulator in any device provided herein is a pneumatic pressure regulator. The pneumatic pressure regulator works with a modified poppet valve. For example, an E/P pressure regulator, series ED05 (Bosch Rexroth AG) can be used. In some cases, the pressure regulator in any device provided herein is a hydraulic pressure regulator. The pressure regulator can also be in communication and/or comprise a flow meter for measuring flow rates within a device as provided herein. The flow meter can be a flow meter, rotometer or mass flow controller known in the art.

The cylindrical chambers (zones), whether they comprise one or two or more chambers such as 91, 92, and 93 within the barrel cylinder 31 and discharge pipe 62 through the valve to atmospheric pressure comprise the reaction zone R1 where pretreatment of the biomass occurs. Pretreatment of the biomass inputted into the barrel cylinder 31 occurs within the barrel chamber 30 as long as the material is at elevated temperatures and pressures, so the reaction zone R1 ends when the material is flashed to atmosphere. The thermochemical and mechanical pressure in this zone, as well as the residence time, can be varied in accordance with the type of biomass being pretreated. Those of skill in the art will recognize that biomass material with a high concentration of easily solubilized and hydrolyzed carbohydrate polymers could require less time and/or less pressure and temperature.

The residence time in the reaction zone can be very short as compared to other pretreatment systems known in the art. The residence time in a reaction zone (e.g., FIG. 1, R1) of a device as provided herein can be less than 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 35, 40, 45, 50, 55, or 60 seconds. The residence time in a reaction zone (e.g., FIG. 1, R1) of a device as provided herein can be about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 35, 40, 45, 50, 55, or 60 seconds. The residence time in a reaction zone (e.g., FIG. 1, R1) of a device as provided herein can be between about 1 second to about 2, about 1 second to about 3 seconds, about 1 second to about 4 seconds, about 1 second to about 5 seconds, about 1 second to about 6 seconds, about 1 second to about 7 seconds, about 1 second to about 8 seconds, about 1 second to about 9 seconds, about 1 second to about 10 seconds, about 1 second to about 15 seconds, about 1 to about 20 seconds, about 2 second to about 4 seconds, about 2 second, to about 6 second, about 2 seconds to about 8 second, about 2 second, to about 10 seconds, about 2 seconds to about 15 second, about 2 seconds to about 20 seconds, about 5 seconds to about 10 seconds, about 5 seconds to about 10 seconds, about 5 seconds to about 15 seconds, about 5 seconds to about 20 seconds, about 10 second to about 12 second seconds, about 10 seconds to about 14 seconds, about 10 seconds, to about 16 seconds, about 10 seconds to about 18 seconds, about 10 seconds to about 20 seconds, about 15 seconds to about 20 seconds, about 20 seconds to about 30 seconds, about 30 seconds to about 45 seconds, or about 45 seconds to about 60 seconds. The pressure can vary from 0 to 1000 psi, preferably from 300-700 psi, or about 325-450 psi. The temperature range is wide, from 100 to 260° C. or more, preferably from 160-230° C. The temperature used often depends on the crystallinity of the cellulose fiber in the biomass; for example, softwood has a higher percent of crystalline cellulose and requires a temperature of 210-240° C. Acid or another chemical may or may not be added to assist with the reaction and can range from 0 wt % of pure chemical per dry tonne of biomass to 8 wt % of pure chemical per dry tonne of biomass, preferably from 1 wt % to 5 wt %.

In another embodiment, the temperature and pressure can be varied to control the output of monosaccharides versus polysaccharides, or C5 versus C6 sugars. Because this system provides uniform, consistent pretreatment of biomass, treatment parameters can be varied to produce particular ratios of C5:C6 sugars with minimal inhibitor formation and high yields. Table 6 is an example of a higher C5:C6 (more than 3:1 ratio of C5 to C6 sugars) yield with reduced inhibitor levels.

In another embodiment, biomass as provided herein can be pre-treated at an elevated temperature and/or pressure in a device as provided herein. In one embodiment, biomass is pre-treated at a temperature range of 20° C. to 400° C. In another embodiment biomass is pretreated at a temperature of about 20° C., 25° C., 30° C., 35° C., 40° C., 45° C., 50° C., 55° C., 60° C., 65° C., 80° C., 90° C., 100° C., 120° C., 150° C., 200° C., 250° C., 300° C., 350° C., 400° C., 500° C. or higher. In another embodiment, biomass is pretreated at a temperature of about 220-238° C. In another embodiment, elevated temperatures are provided by the use of steam, hot water, or hot gases. In one embodiment steam can be injected into a biomass containing vessel or barrel chamber. In another embodiment the steam, hot water, or hot gas can be injected into a vessel jacket such that it heats, but does not directly contact the biomass. In an additional embodiment heat can be externally applied using electric barrel heaters. According to certain embodiments of the present disclosure, the elevated temperature is solely maintained by addition of the steam. In a further embodiment, a cooling jacket or a dual heating and cooling jacket, using water or glycol, can be used to reduce the temperature or quench reactions in the reaction zone. The heating and cooling systems can be built into the extruder system or can comprise an external system. In another embodiment, there can be provided a port for the addition of water or another chemical, to reduce temperature in the reaction zone and/or control the release of specific types of monosaccharides or polysaccharides.

In another embodiment, biomass as provided herein can be pre-treated at an elevated temperature and/or pressure in a device as provided herein. In one embodiment, biomass is pre-treated at a pressure range of from 0 to 1000 PSI. In some embodiments, heating the biomass pretreated in a device as provided herein is performed at a pressure higher than atmospheric. The pressure can be from about 25 PSI to about 800 PSI. The pressure can be from about 300 PSI and 500 PSI. The pressure can be about 400 PSI. For example, the pressure can be about 25-800, 25-700, 25-600, 25-500, 25-250 PSI, 25-225 PSI, 25-200 PSI, 25-175 PSI, 25-150 PSI, 25-125 PSI, 25-100 PSI, 25-75 PSI, 25-50 PSI, 50-225 PSI, 50-200 PSI, 50-175 PSI, 50-150 PSI, 50-125 PSI, 50-100 PSI, 50-75 PSI, 75-200 PSI, 75-175 PSI, 75-150 PSI, 75-125 PSI, 75-100 PSI, 100-175 PSI, 100-150 PSI, 100-125 PSI, 125-150 PSI, 25 PSI, 30 PSI, 35 PSI, 40 PSI, 45 PSI, 50 PSI, 55 PSI, 60 PSI, 65 PSI, 70 PSI, 75 PSI, 80 PSI, 85 PSI, 90 PSI, 95 PSI, 100 PSI, 105 PSI, 110 PSI, 115 PSI, 120 PSI, 125 PSI, 130 PSI, 135 PSI, 140 PSI, 145 PSI, 150 PSI, 155 PSI, 160 PSI, 165 PSI, 170 PSI, 175 PSI, 180 PSI, 185 PSI, 190 PSI, 195 PSI, 200 PSI, 205 PSI, 210 PSI, 215 PSI, 220 PSI, 225 PSI, 230 PSI, 235 PSI, 240 PSI, 245 PSI, 250 PSI, 300 PSI, 350 PSI, 400 PSI, 450 PSI, 500 PSI, 550 PSI, 600 PS, 650 PSI, 700 PSI, 750 PSI, 800 PSI, 850 PSI, 900 PSI, 950 PSI, or 1000 PSI. In one embodiment, the pressure is from about 25 PSI to about 250 PSI. In another embodiment, the pressure is from about 75 PSI to about 200 PSI. In another embodiment, the pressure is from about 100 PSI to about 400 PSI. In another embodiment, the pressure is from about 325 to about 450 PSI.

In one embodiment, one or more acids can be combined, resulting in a buffer that can be used for conducting pretreatment of biomass as provided herein in a device as provided herein. In some instances, the pH can be lowered to neutral pH or acidic pH, for example a pH of 7.0, 6.5, 6.0, 5.5, 5.0, 4.5, 4.0, or lower. For example, the non-neutral aqueous medium used to pretreat biomass as provided herein in a device as provided herein can have a pH that is less than 7, 6.5, 6, 5.5, 5, 4.5, 4, 3.5, 3, 2.5, 2, 1.5, or 1. For example, the non-neutral aqueous medium can have a pH that is about 6.5, 6.4, 6.3, 6.2, 6.1, 6, 5.9, 5.8, 5.7, 5.6, 5.5, 5.4, 5.3, 5.2, 5.1, 5, 4.9, 4.8, 4.7, 4.6, 4.5, 4.4, 4.3, 4.2, 4.1, 4, 3.9, 3.8, 3.7, 3.6, 3.5, 3.4, 3.3, 3.2, 3.1, 3, 2.9, 2.8, 2.7, 2.6, 2.5, 2.4, 2.3, 2.2, 2.1, 2, 1.9, 1.8, 1.7, 1.6, 1.5, 1.4, 1.3, 1.2, 1.1, 1, 0.9, 0.8, 0.7, 0.6, 0.5, 0.4, 0.3, 0.2, 0.1, or lower. In some embodiments, the pH is lowered and/or maintained within a range of about pH 4.5 to about 7.1, or about 4.5 to about 6.9, or about pH 5.0 to about 6.3, or about pH 5.5 to about 6.3, or about pH 6.0 to about 6.5, or about pH 5.5 to about 6.9 or about pH 6.2 to about 6.7.

In some embodiments, pretreatment of a biomass as provided herein in a device as provided herein comprises hydration of the biomass composition in a non-neutral aqueous medium having a pH that is greater than 7. For example, the non-neutral aqueous medium can have a pH that is greater than 7, 7.5, 8, 8.5, 9, 9.5, 10, 10.5, 11, 11.5, 12, 12.5, 13, 13.5 or higher. For example, the non-neutral aqueous medium can have a pH that is about 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, 10, 10.1, 10.2, 10.3, 10.4, 10.5, 10.6, 10.7, 10.8, 10.9, 11, 11.1, 11.2, 11.3, 11.4, 11.5, 11.6, 11.7, 11.8, 11.9, 12, 12.1, 12.2, 12.3, 12.4, 12.5, 12.6, 12.7, 12.8, 12.9, 13, 13.1, 13.2, 13.3, 13.4, 13.5, 13.6, 13.7, 13.8, 13.9, or higher. The non-neutral aqueous medium having a pH greater than 7 can comprise one or more bases such as sodium hydroxide, calcium hydroxide, potassium hydroxide, ammonia, ammonia hydroxide, hydrogen peroxide or a combination thereof. The one or more bases can be at any suitable concentration, such as any of the concentrations disclosed herein.

In some embodiments, pretreatment of a biomass composition comprises hydration of the biomass composition in a non-neutral aqueous medium comprises from about 0.1% to about 50% w/w or v/v by dry biomass weight of one or more acids or one or more bases. For example, the non-neutral aqueous medium can comprise about 25-50%, 10-50%, 10-25%, 5-50%, 5-25%, 5-10%, 4-50%, 4-25%, 4-10%, 4-5%, 3-50%, 3-25%, 3-10%, 3-5%, 3-4%, 2-50%, 2-25%, 2-10%, 2-5%, 2-4%, 2-3%, 1-50%, 1-25%, 1-10%, 1-5%, 1-4%, 1-3%, 1-2%, 0.5-50%, 0.5-25%, 0.5-10%, 0.5-5%, 0.5-4%, 0.5-3%, 0.5-2%, 0.5-1%, 0.5-%, 0.1-50%, 0.1-25%, 0.1-10%, 0.1-5%, 0.1-4%, 0.1-3%, 0.1-2%, 0.1-1%, 0.1-0.5%, 50%, 45%, 40%, 35%, 30%, 25%, 24%, 23%, 22%, 21%, 20%, 19%, 18%, 17%, 16%, 15%, 14%, 13%, 12%, 11%, 10%, 9.5%, 9%, 8.5%, 8%, 7.5%, 7%, 6.5%, 6%, 5.5%, 5%, 4.9%, 4.8%, 4.7%, 4.6%, 4.5%, 4.4%, 4.3%, 4.2%, 4.1%, 4%, 3.9%, 3.8%, 3.7%, 3.6%, 3.5%, 3.4%, 3.3%, 3.2%, 3.1%, 3%, 2.9%, 2.8%, 2.7%, 2.6%, 2.5%, 2.4%, 2.3%, 2.2%, 2.1%, 2%, 1.9%, 1.8%, 1.7%, 1.6%, 1.5%, 1.4%, 1.3%, 1.2%, 1.1%, 1%, 0.9%, 0.8%, 0.7%, 0.6%, 0.5%, 0.4%, 0.3%, 0.2%, or 0.1% of the one or more acids or the one or more bases. The one or more acids can be sulfuric acid, peroxyacetic acid, lactic acid, formic acid, acetic acid, citric acid, phosphoric acid, hydrochloric acid, sulfurous acid, chloroacetic acid, dichloroacetic acid, trichloroacetic acid, trifluoroacetic acid, oxalic acid, benzoic acid, or a combination thereof. The one or more bases can be sodium hydroxide, calcium hydroxide, potassium hydroxide, ammonia, ammonia hydroxide, hydrogen peroxide or a combination thereof. In some embodiments, the non-neutral aqueous medium comprises the one or more acids or the one or more bases at from about 1% to about 5% v/w by dry biomass weight. In some embodiments, the non-neutral aqueous medium comprises sulfuric acid at from about 1% to about 5% v/w by dry biomass weight. In some embodiments, the non-neutral aqueous medium comprises sulfuric acid at about 1.8% v/w by dry biomass weight. In some embodiments, the non-neutral aqueous medium comprises sulfuric acid at about 1% v/w by dry biomass weight. In some embodiments, the non-neutral aqueous medium comprises sulfuric acid at about 1-2% v/w by dry biomass weight. In some embodiments, the non-neutral aqueous medium comprises sulfuric acid at about 1.5% v/w by dry biomass weight.

In the flash tank 70, the biomass can move through a downward directed pipe. The pretreated biomass can be accessible from the flash tank 70. In some cases, a device for pretreating biomass as provided herein can be designed to move the biomass to a separation step or to an enzyme hydrolysis tank. Vapors can be discharged through the open top of the flash tank 70 or, in the alternative, the flash tank 70 can be closed and vapors discharged through a pipe to another area or chamber. Alternatively, the pipe can be connected through a tubing to a condenser.

The apparatus (e.g., barrel cylinder) can be constructed using carbon steel, stainless steel or any other material that is impervious to acid and alkali and that can withstand the pressures generated. It is also possible to have a chemically-inert coating on the inside of the chamber (e.g., barrel cylinder inner chamber) that does not react with acid or alkali or any chemical that is used in the methods provided herein. The cylindrical barrel may be horizontal or vertical with modifications for loading biomass or providing the proper discharge pressure. One skilled in the art could readily configure the apparatus with a vertical barrel for proper operation.

Figure 2:
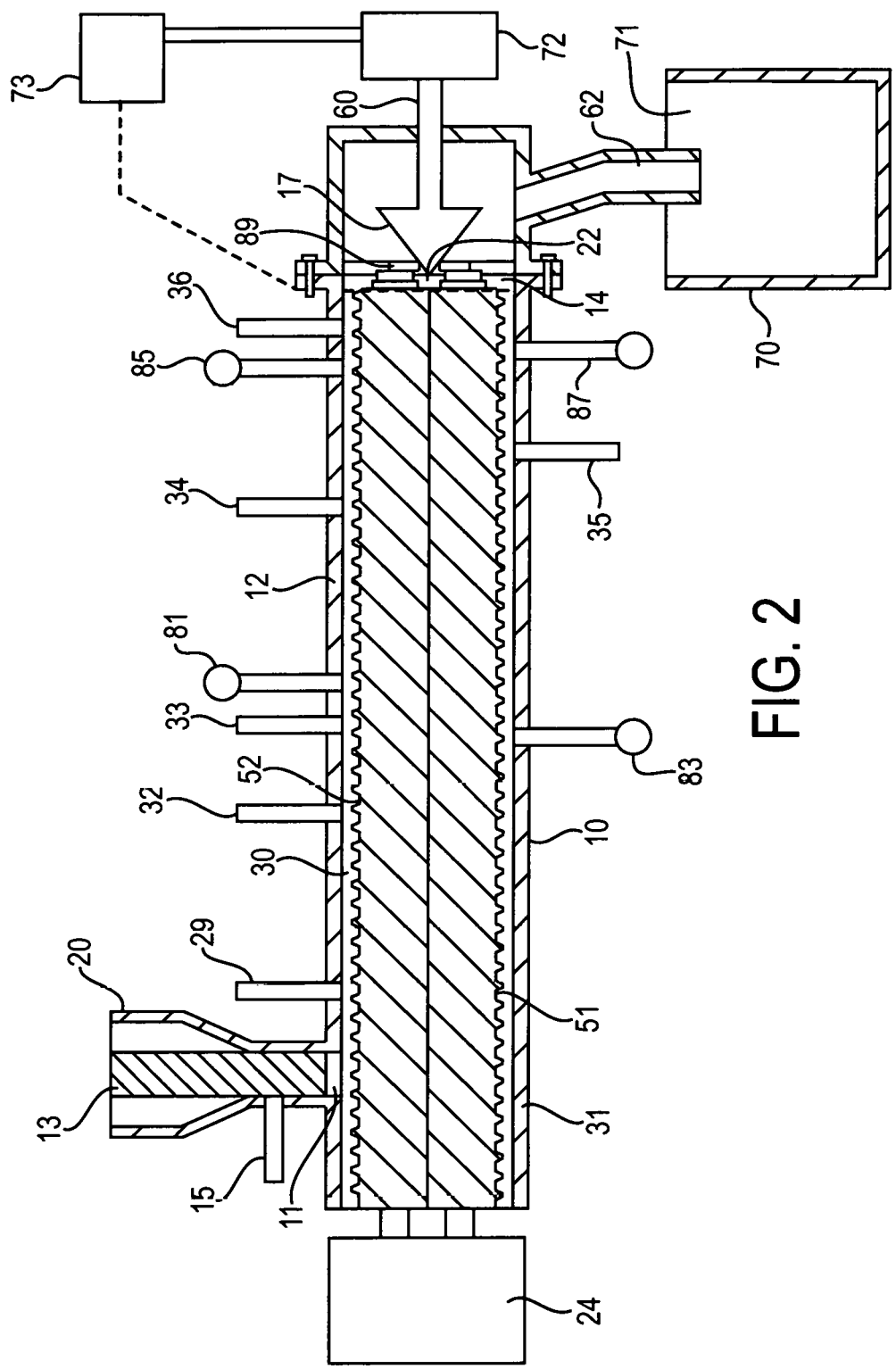
FIG. 2 is a horizontal fragmentary sectional view of an embodiment of an apparatus disclosed herein illustrating the barrel, screws, and end valve attached to a twin screw extruder of the invention.

In some cases, a device for pretreating biomass as provided herein comprises a twin-screw extruder. An example of a co-rotating, twin-screw extruder used for the methods provided herein is shown in FIG. 2. The twin-screw extruder in FIG. 2 comprises barrel 31, a horizontal cylindrical chamber 30, which includes two screw-type feeder mechanisms 51 and 52. The barrel comprises an open first end 11 for adding biomass. The biomass can be any biomass as provided herein. The overall extrusion apparatus 10 includes a primary feed hopper 20 to contain the biomass being added. Inside the hopper 20 is a delivery auger 13 to evenly distribute the material into the open first end 11. There is a port 15 into which water can be added as the biomass enters the extruder chamber 30. The cylindrical chamber 30 has another port 29 for water, sealable ports 32, 33 for the addition of pressurized steam and sealable ports 34, 35 for the addition of chemical reactant (e.g., acid). A third port 36 can be added if additional steam or water, or even a pH adjusting agent is needed downstream of ports 34 and 35. As in FIG. 1, the barrel chamber 30 is divided into 1-3 zones (not shown), produced by screw configurations, akin to 91 in FIG. 1, or 91, 92, and 93 in FIG. 14. Pressurized steam is injected to raise the temperature and pressure of the biomass, and chemical for the chemical reaction, if necessary. Insulation 12 can be provided outside or as part of the barrel 31 that can encompass the barrel chamber 30 and maintain the desired temperature inside the chamber. Temperature gauges 83, 87 and pressure gauges 81, 85 are used to monitor temperature and pressure inside the chamber, respectively.

As biomass is loaded through the hopper 20 into the chamber 30, thermo-mechanical pressure builds through the addition of steam and the configuration of the high pressure plug P1 (due to the shape and movement of various sections of the screw mechanisms). The twin screw mechanism 51, 52 moves the biomass through the tube to the opening 22 between the end plate 14 of the barrel chamber 30 and the discharge valve 89.

As in FIG. 1, the device of FIG. 2 produces a high pressure plug P1 during the process of moving biomass through the tube from one end to the other (see FIG. 1). While not shown in FIG. 2, P1 is formed after the optional addition of water through port 29 prior to the addition of steam through the ports 32 and 33. Ports 32, 33 add pressurized steam at about 300 psi to 1000 psi to the barrel after the first plug is formed increasing the barrel pressure to a desired temperature and pressure; for example, 600 psi and a temperature of 253° C. Also like FIG. 1, in FIG. 2 the zone within the barrel chamber 30 between P1 and the area of discharge is zone 91. The zone 91 between the high pressure plug and the area of discharge through the special end flange 14 collectively constitute the reaction zone R1 (as shown in FIG. 1). Reaction zone R1 may include any other permeable plugs and zones that can be formed as shown in FIG. 14. In some cases, chemicals used to assist in the pretreatment of the biomass (e.g., acid or alkali or another chemical) are added between the high pressure plug P1 and the discharge area in the reaction zone R1.

In some cases, pretreatment of biomass using a device as depicted in FIG. 2 entails sealing the ports in the device of FIG. 2 following movement of biomass through each section and addition of aqueous solution comprising acid and steam and subsequently maintaining a desired temperature. As shown in FIG. 2, the discharge valve 17 can be partially seated in a metal or ceramic seal 89 such that the discharge valve is mostly closed. In operation, (FIG. 2 and FIG. 12) as pressure in the barrel chamber 30 builds to a certain point, the discharge valve 17 is pushed open (away from the barrel chamber). The valve shaft 60 extends through a tube to an actuator 72 within or attached to a back pressure generator (control unit) 73. The mixture of biomass, sugars, and aqueous chemical is pushed through the discharge valve opening 22 by the movement of the twin screws 50, 51 in the chamber 30 from the first end towards the second (outlet) end and from the pressure buildup. The biomass passes through the discharge valve opening 22 and through a pipe 62 where it is collected in a flash tank 70 through an opening 71 in the top of the flash tank which allows access to pretreated biomass and the exit of vapors. There can also be a separate opening to allow discharge of vapors (not shown).

Pressure is built and maintained in the reaction zone. Due to the configuration of the screw elements and a combination of reversing and kneading blocks, material can be compacted as it approaches the special set of plug forming screw elements, and the elevated pressure to facilitate successful operation can be achieved as the material is compacted and conveyed through the plug formation zone. As described supra, the plug P1 that is formed is not only compacted but can also be impervious to liquid and steam. The rest of the plugs P2 and P3 can be high shear zones to aid in mixing as described supra. The forward motion of the screws can ensure that the pressure is built and correct pressure is maintained throughout the reaction zone R1. The plug P1 that is formed from the compacted material can be impervious to steam so that no pressure can be released back at a high pressure, e.g., between 500 to 1000 psi or higher. This configuration can contribute significantly to the rapid duration of pretreatment and/or the establishment of the difference in between the pressure at the discharge valve opening 22 and the internal pressure, so that the steam explosion can be most effective.

Steam explosion is the explosive decompression of the biomass that can result in a rupture of the biomass fibers rigid structure. The sudden pressure release can defibrillate the cellulose bundles, resulting in a better accessibility of the cellulose for enzymatic hydrolysis and fermentation. Depending on residence time and temperature, this rapid decompression to atmospheric pressure can result in anything from small cracks in a biomass structure, to total defibrillation of plant fibers.

Under this system, lignocellulosic biomass can be heated at high temperatures and pressures without variation in temperature and pressure due to leakage through the compacted materials in the extruder, which can be followed by mechanical disruption of the pretreated material by violent discharge into a collecting tank (explosion). This can result in uniformly-treated material due to the turning of the screws and the uniform exposure of the biomass to temperature, pressure, and various reactants in each treatment section of the extruder.

The high-pressure steam can radically modify the plant cell wall structure, yielding a dark brown material from which partially-hydrolyzed hemicelluloses can easily be recovered by water-washing, leaving a water-insoluble fraction composed of cellulose, residual hemicelluloses and lignin that can be further hydrolyzed through enzymatic hydrolysis or other treatments.

Dilute acid pretreatment, while significantly increasing accessibility to cellulose, can produces acidic conditions that may result in the destruction and loss of xylose. However, by bringing the particle size, temperature and pressure to correct parameters before the addition of acid, the acid treatment can be accomplished in a rapid (e.g., a few seconds) and uniform manner, thus limiting the loss of xylose and reducing inhibitor formation.

Figure 3:
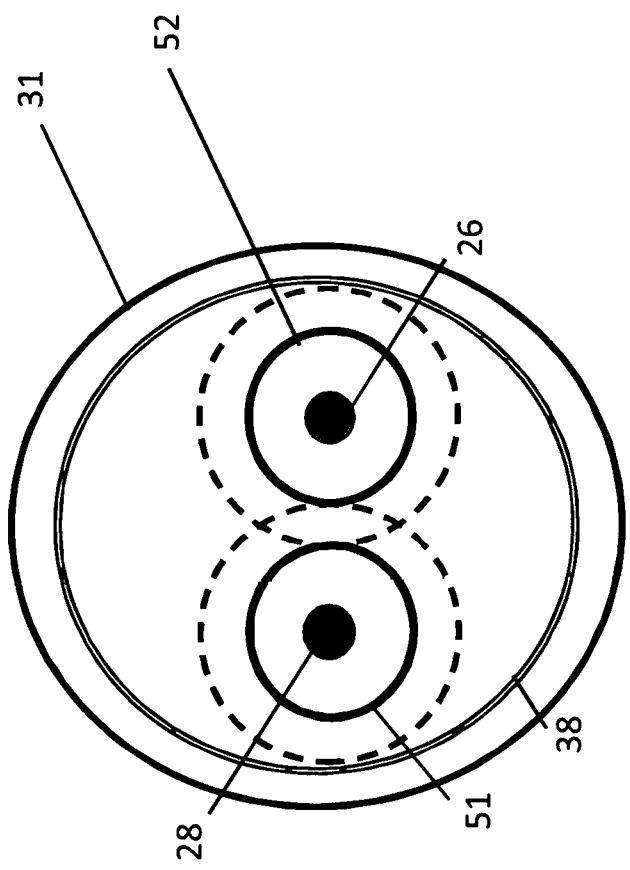
FIG. 3 is a cross-sectional view similar to that of FIG. 2 that depicts the extruder with the twin screws.
Figure 4:
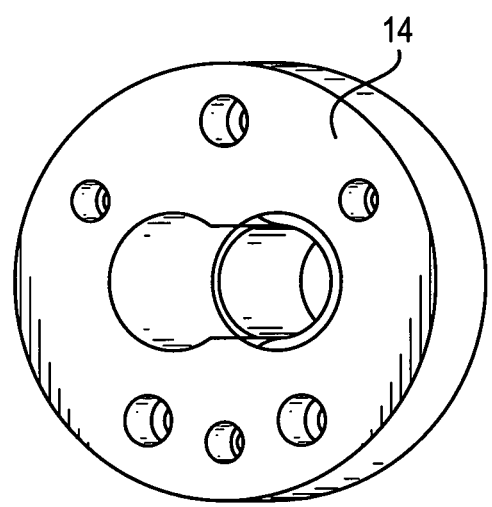
FIG. 4 is a cross-sectional view of the end plate of the extruder that abuts the end of the discharge valve.
Figure 5:
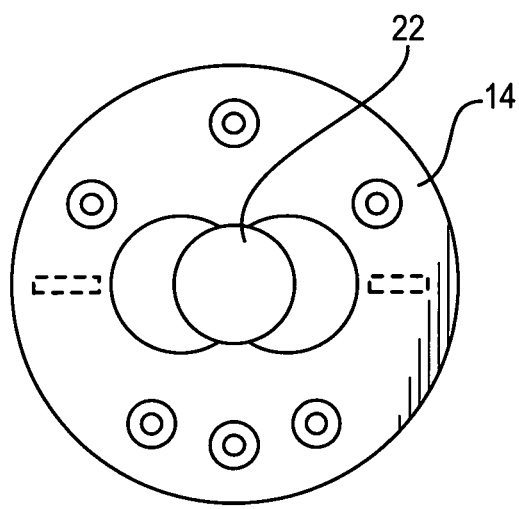
FIG. 5 is a schematic cross-sectional view of the end plate of the extruder and the opening of the valve plate that abuts the end of the extruder.
Figure 6:
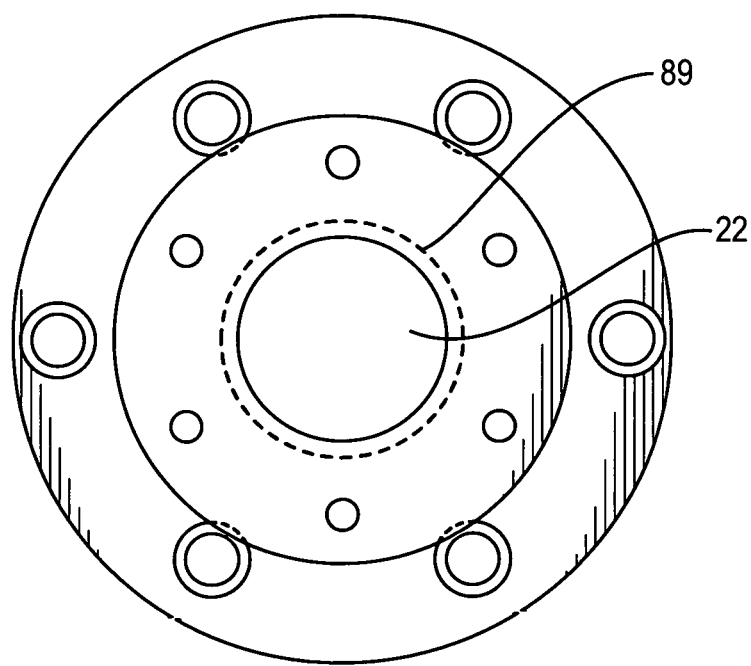
FIG. 6 is a cross-sectional view of the end of the discharge valve plate that abuts the end of the extruder showing the seal facing.

A cross section of the discharge end of the twin screw extruder shown in FIG. 2 is depicted in FIG. 3. As shown in FIG. 3, the barrel 31 houses the twin screws 51, 52 which are turned by the shafts 26, 28. In one embodiment, a replaceable solid barrel insert 38 of corrosion and wear-resistant specialty metal or other compound can surround the screws. The extent of the blade edges of the twin screws 51, 52 and the boundaries of the bored holes through the barrel insert 38 are represented by dotted lines. There is 1 mm or so between the tips of the screw elements and the barrel insert 38. In some instances, the dotted lines can be the actual barrel openings (instead of barrel 31) and can be comprised of specialty metal inserts added for wear resistance and bored out to match the diameter of the screws. In one embodiment, a heating or heating/cooling apparatus (not shown) is fitted around a whole cylindrical barrel. In another embodiment, the heating/cooling system (not shown) is built into the system. FIG. 4 shows a cross section of the discharge end special face flange 14 that is attached to the end of the extruder. The flange 14 is connected to the extruder and the twin screws convey material onward to the discharge valve. FIG. 5 depicts the transition from the two-screw opening in the extruder discharge end flange 14 to the single outlet of the valve opening 22 when looking from the end of the valve opening from the narrow end that connects with valve 17. The opening expands to encompass the two-screw opening of flange 14. FIG. 6 further depicts the discharge valve end housing 19 with a single cylindrical opening 22 that connects adjacent to the extruder flange 14. Pretreated biomass is discharged through the opening 22 surrounded by the metal or ceramic seal 89 which is secured in position to interact with the discharge valve mechanism. The ceramic or metal seal can also extend into the valve opening 22 and provide a coating or insert between the valve opening 22 and the valve housing 19.

Figure 7:
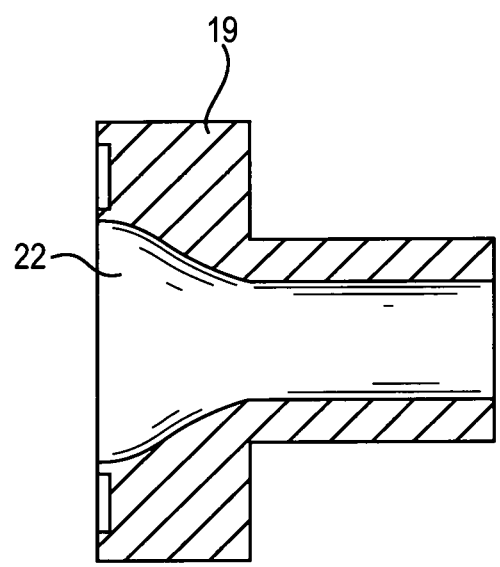
FIG. 7 is a horizontal fragmentary sectional view of the transition from the discharge of the twin screws to the outlet orifice.

The valve at the discharge end ("end valve") of an extruder as provided herein can be one of many different designs and can be a variable orifice valve. The end valve used in this process can be one of several types that can be precisely monitored and the discharge can be controlled by a back pressure generator. The end valve can be unidirectional or bidirectional. In some cases, an end valve in an extruder as provided herein is unidirectional while the flow through the extruder is unidirectional. In some cases, an end valve in an extruder as provided herein is bidirectional while the flow through the extruder is unidirectional. FIG. 7 is a horizontal view of the valve opening 22 in its housing 19 where it narrows from the two-screw openings of the extruder to the valve discharge end.

Figure 8:
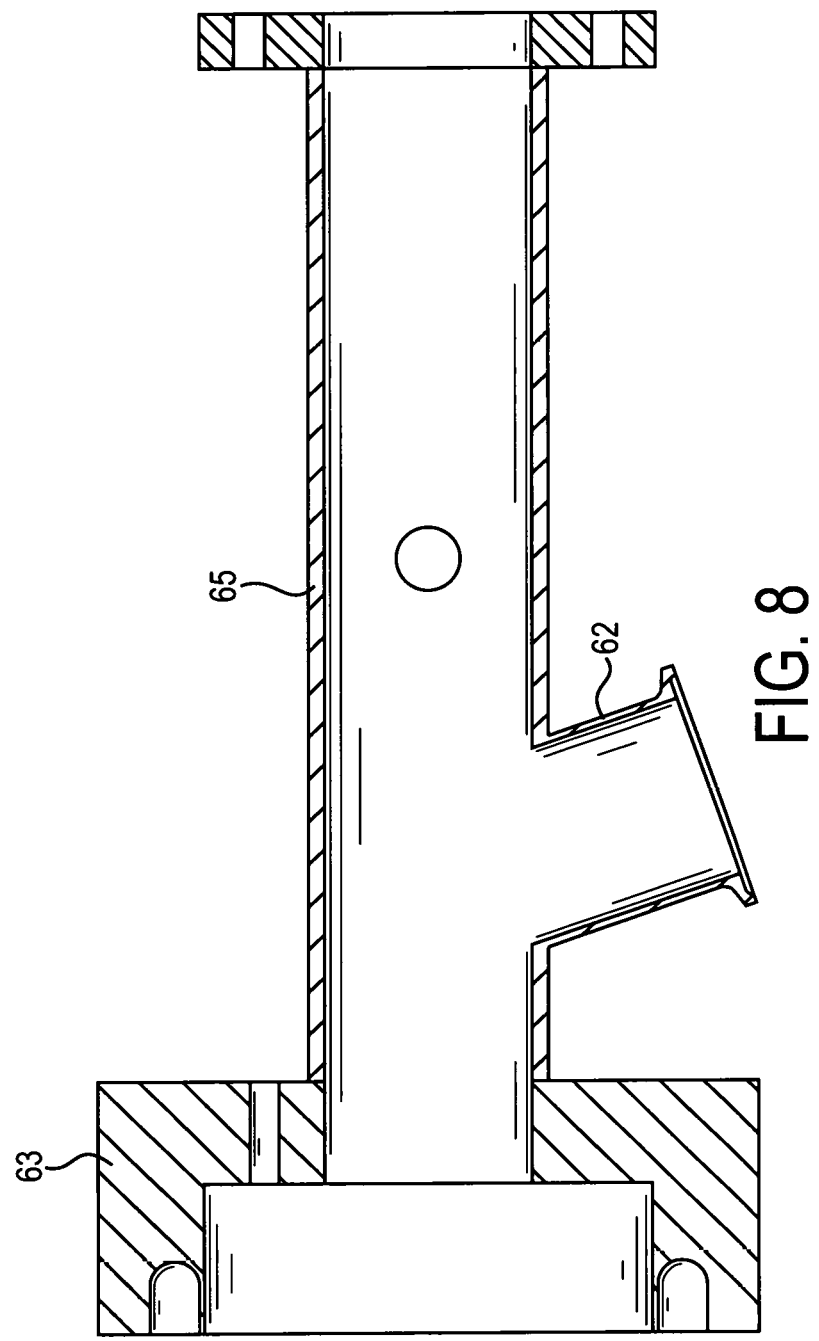
FIG. 8 is a horizontal sectional view of the housing for a valve assembly.
Figure 9:
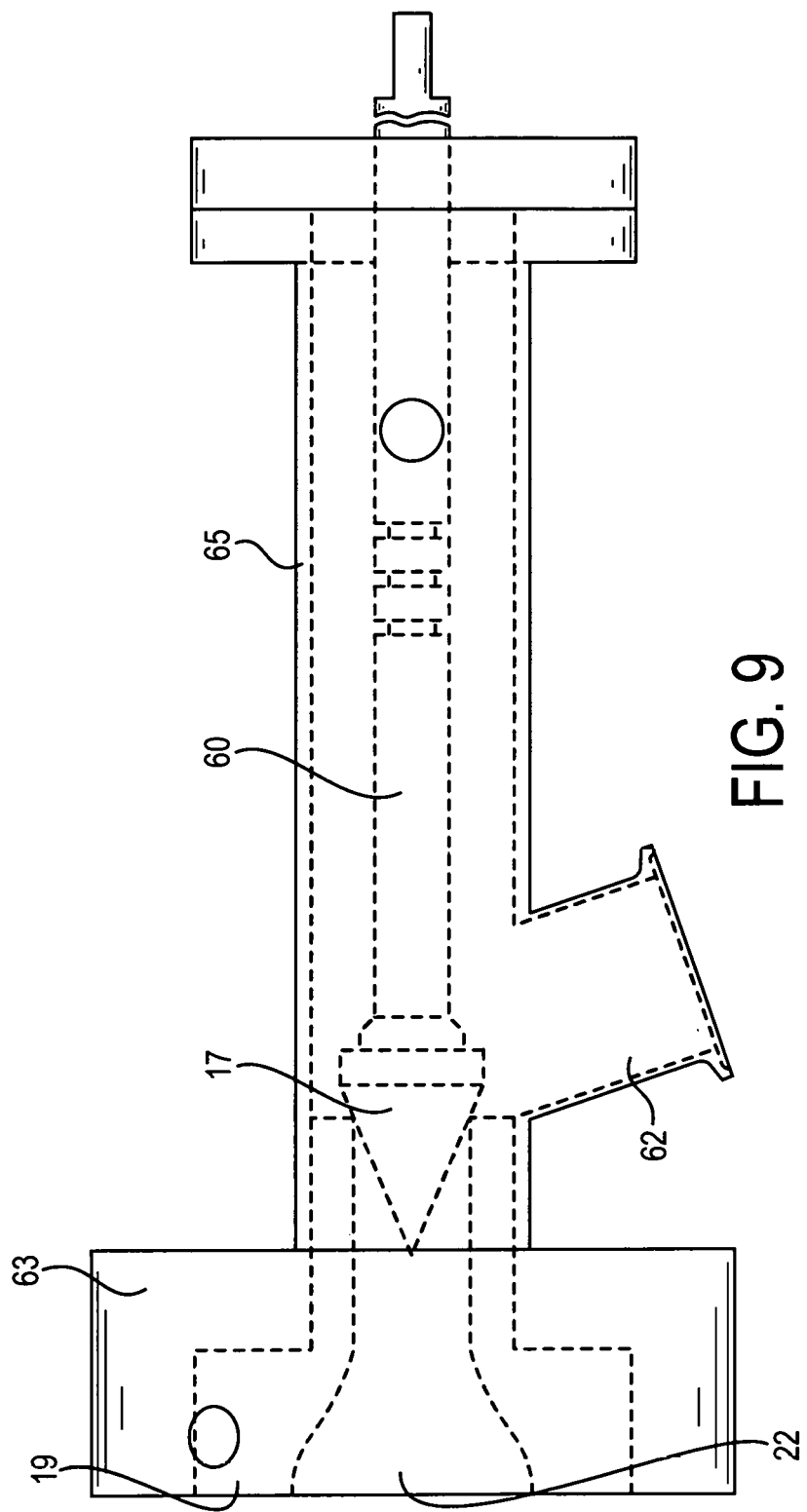
FIG. 9 is a schematic drawing showing how the valve assembly fits into the housing.
Figure 10:
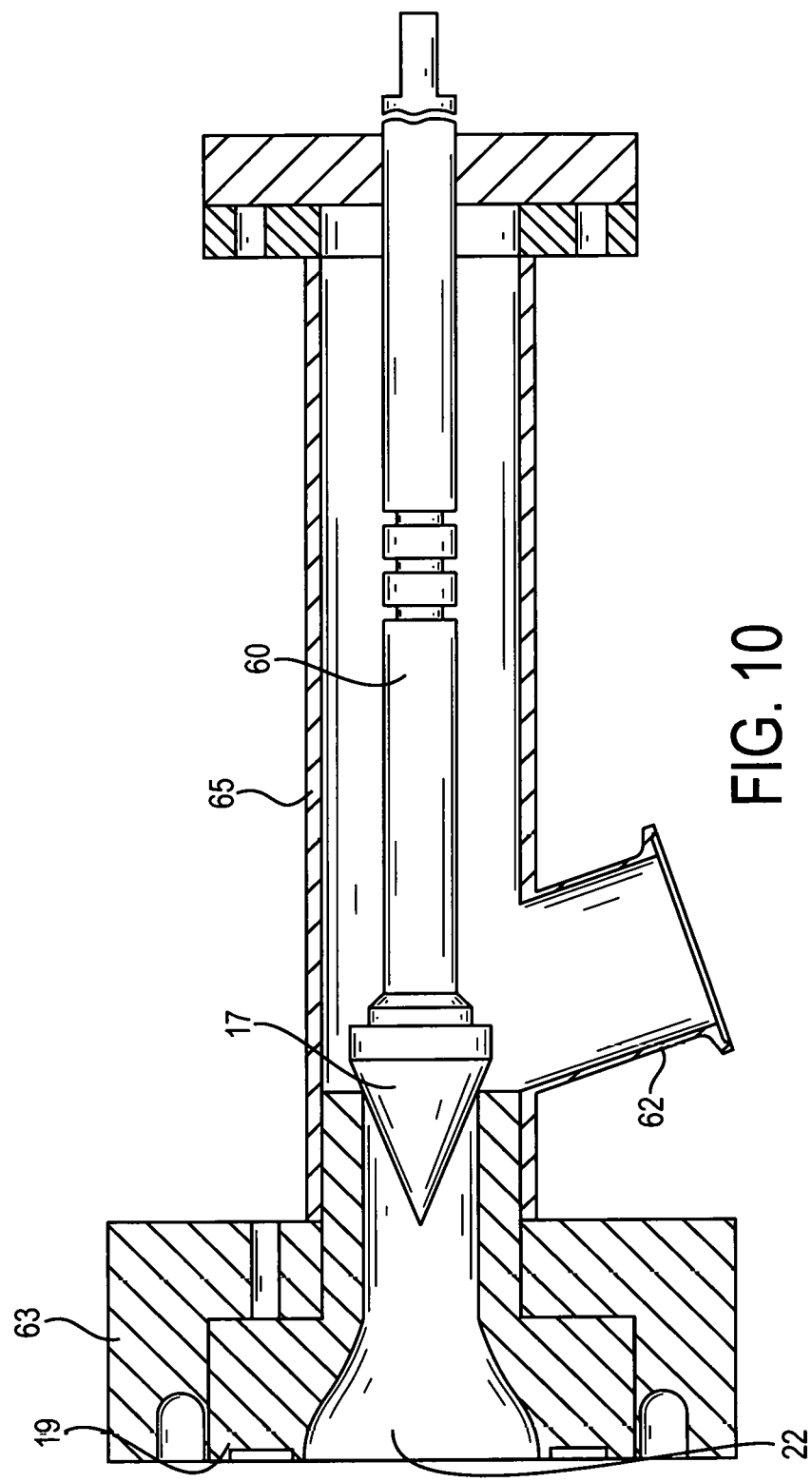
FIG. 10 is a horizontal sectional view of the valve assembly in the housing.

FIG. 8 is a horizontal view of the valve housing assembly 65 with the discharge pipe 62, including the housing 63 that holds the valve opening and housing 19 as shown in FIG. 7. FIG. 9 depicts the housing of FIG. 8, showing how the valve assembly is integrated with the housing. FIG. 10 is a horizontal sectional view with the valve 17 and valve shaft 60 seated in the valve opening housing 19 within the housings 65 and 63.

FIGS. 2 and 14 are embodiments that show the movement of the biomass through reactors using plugs to chamber different reactions, to maintain temperature and pressure, to facilitate intimate and complete mixing of all materials introduced into the system, and to reduce particle size. These embodiments can be varied to accommodate different types and sizes of biomass for optimal processing and the recovery of monosaccharides or even oligomers. For example, the size of the second chamber can be reduced if the biomass contains a small percentage of hemicellulose compared to the cellulosic portion. Residence time in any chamber can be varied and those of skill in the art will understand that the types of screw elements in sections that produce the plugs, and cut and move the processing materials forward and their placement can have an infinite number of permutations. The combinations used will depend on the type of biomass and the size of the particles desired for optimum pretreatment. Thus residence time, temperature, time, and chemical treatment can be unlimited using this method.

Screw sections incorporated into this system can include, for example, conveying elements for moving materials through the extruder and kneading block elements for forming plugs. One suitable system can be comprised of a single flight screw element with mixing grooves in the screw profile. The element can have a left hand (reversed conveying) or right hand (forward conveying pitched screw profile). These elements can comprise less mixing grooves and reduced groove depth to reduce the product cross flow between the screw profile channels, thus assisting to maintain a uniform pressure and movement of the biomass and reduce backflow. The screw elements can be comprised of various materials, including, for example, Stellite, Hastelloy, Inconell, PM steel, Chromium steel, and nitride steel, and/or can be manufactured with various surface coatings to reduce wear and abrasion. Examples of such elements can be found at Extricom GmbH (www.extricom.de) or Century Extrusion (www.centuryextrusion.com). Those of skill in the art will understand the types of elements and their arrangement are unlimited and can be organized in many different patterns for specific biomass materials.

The initial dry weight of biomass used in the methods of this invention is at least about 10% of the total weight of the biomass and aqueous acid mixture. More typically, the dry weight of biomass is at least about 20%, and can be at least about 30%, 45%, 50%, or more. Feedstock biomass will typically range between 30 wt % and 90 wt % solids, and the biomass exiting the pretreater will typically range between 21 wt % and 40 wt % solids. The percent dry weight of biomass may vary and the optimal percent may be different for different types of biomass. For example, biomass of at least about 40% is desired when using sawdust (sawdust will get diluted with a small amount of steam condensate), to provide pretreated biomass that is saccharified to produce fermentable sugars concentrated sufficiently for cost-effective fermentation to ethanol. More suitable is sawdust biomass that is at least about 30%. The preferred percent dry weight of a particular type of biomass for use in the present methods for producing a high sugars hydrolysate can be readily determined by one skilled in the art.

The biomass can be loaded into a feeder apparatus such as the hopper diagrammed in FIG. 1, which, in turn, feeds it to the reactor. The loading can be facilitated by use of a flow conveyor such as a screw conveyor, crammer, drag chain, bucket elevator, conveyor belt, or the like. The feeding of the biomass into the reactor can be made more uniform by the addition of a conical screw or the like, that allows the biomass to enter the reactor at a uniform rate and density that is helpful to keep the feeder apparatus from clogging.

Using this method, an aqueous solution comprising acid or base can comprise any concentration that is necessary to hydrolyze the carbohydrate polymers. Thus, for example, acid at a concentration of 0.01% to over 7 or 8%, or concentrations of 1%, 2%, 3%, 4%, 5%, 6% or anything in between can be used. In pretreatment devices as provided herein, ports, excluding the one or more through which steam is being added, can be sealed. Valves for use in the devices as provided herein can be any type of valve known in the art with a variable orifice that can be opened or closed. The valves can be ball valves, poppet valves, check valves, or rotating knife-gate valves, or combinations thereof.

Steam can be added through one or more ports in the cylindrical barrel at the beginning of the reaction zone, after the first plug is formed, in an amount that is needed to raise the temperature of the biomass and aqueous acid mixture to the desired point. More than one port can be used, with ports being spaced so that steam contact is distributed over the biomass or to raise the temperature and pressure more quickly. Pressurized steam can be added to raise the temperature of the biomass and aqueous acid mixture to between about 80° C. and about 300° C., preferably between 160° C. and 230° C. The temperature of the biomass and aqueous acid can be about 20° C., 25° C., 30° C., 35° C., 40° C., 45° C., 50° C., 55° C., 60° C., 65° C., 80° C., 90° C., 100° C., 120° C., 150° C., 200° C., 250° C., 300° C., 350° C., or 400° C. The temperature of the biomass and aqueous acid can be from about 20° C. to about 400° C., about 50° C. to about 350° C., about 80° C. to about 300° C., about 100° C. to about 250° C., or about 160° C. to about 210° C. Additional steam can be added through a port between the second and third plug formation of cylindrical chamber, if needed, to maintain the desired temperature and pressure. The apparatus can include a heating jacket, steam jacket, band heaters, barrel heaters, or insulation jacket to contribute to raising and/or maintaining the temperature and pressure. Heating or steam jackets are particularly suited to small scale reactors while insulation jackets are suited to large scale reactors. Heating can occur at different stages, including preheating the barrel prior to treating or pretreating. The type of biomass being pretreated also can affect the optimum time and temperature for treatment in the present method, as can readily be assessed by one skilled in the art.

Bringing the biomass to the described temperatures using pressurized steam in these methods results in pressures within the reactor chamber that are between about 300 psi and about 1000 psi. More typically, pressure is between about 300 psi to 800 psi. The pressurized steam is added through the ports at about 300 to 600 psi. The pressures within the reactor chamber can be 25-250 PSI, 25-225 PSI, 25-200 PSI, 25-175 PSI, 25-150 PSI, 25-125 PSI, 25-100 PSI, 25-75 PSI, 25-50 PSI, 50-225 PSI, 50-200 PSI, 50-175 PSI, 50-150 PSI, 50-125 PSI, 50-100 PSI, 50-75 PSI, 75-200 PSI, 75-175 PSI, 75-150 PSI, 75-125 PSI, 75-100 PSI, 100-175 PSI, 100-150 PSI, 100-125 PSI, 125-150 PSI, 25 PSI, 30 PSI, 35 PSI, 40 PSI, 45 PSI, 50 PSI, 55 PSI, 60 PSI, 65 PSI, 70 PSI, 75 PSI, 80 PSI, 85 PSI, 90 PSI, 95 PSI, 100 PSI, 105 PSI, 110 PSI, 115 PSI, 120 PSI, 125 PSI, 130 PSI, 135 PSI, 140 PSI, 145 PSI, 150 PSI, 155 PSI, 160 PSI, 165 PSI, 170 PSI, 175 PSI, 180 PSI, 185 PSI, 190 PSI, 195 PSI, 200 PSI, 205 PSI, 210 PSI, 215 PSI, 220 PSI, 225 PSI, 230 PSI, 235 PSI, 240 PSI, 245 PSI, 250 PSI, 300 PSI, 350 PSI, 400 PSI, 450 PSI, 500 PSI, 550 PSI, 600 PS, 650 PSI, 700 PSI, 750 PSI, 800 PSI, 850 PSI, 900 PSI, 950 PSI, or 1000 PSI. However, under certain circumstances a lower pressure could be desirable. For example, it takes little or no pressure to release C5 polymers from a C5-rich and/or lignin-free biomass.

In the embodiments of this invention (e.g., FIGS. 1 and 2), following pre-treatment of a biomass as provided herein for the desired time at the proper pressure and temperature, the biomass and aqueous chemical or other mixture is moved through a discharge valve 17 at the end of the cylindrical band 30 into a flash tank 70. The discharge valve 17 can be closed during biomass reaction with aqueous acid or other chemical at the desired temperature, then opened for passage of the biomass. In a twin screw chamber reactor, as exemplified in FIG. 2, the discharge valve 17 opens under pressure of the extruder with the opening of the valve between the end of the extruder and the valve chamber, after the steam and biomass has built up pressure in the reaction chamber, and discharges pretreated biomass to relieve the pressure to the point that the pressure delivered to the end valve through the shaft is greater. The use of the external valve is a great advantage over attempting to maintain homogeneous pressure in the barrel when using plug formation to maintain various zones. The zones can be maintained more easily when a release of pressurized material is controlled by a separately-responsive pressurized valve.

Figure 11:
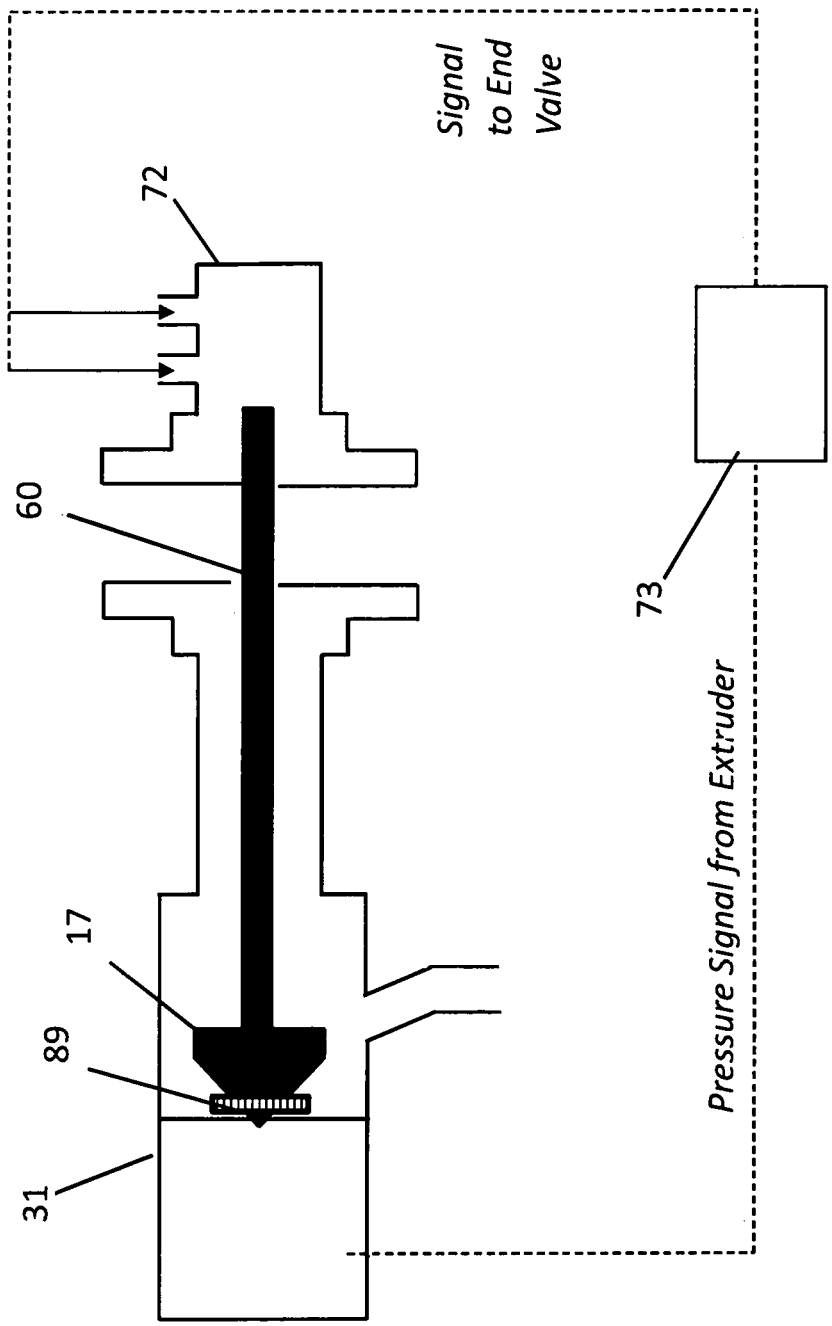
FIG. 11 is a schematic drawing of one embodiment of a gradual expansion venturi used as a discharge valve with the valve mostly closed.
Figure 12:
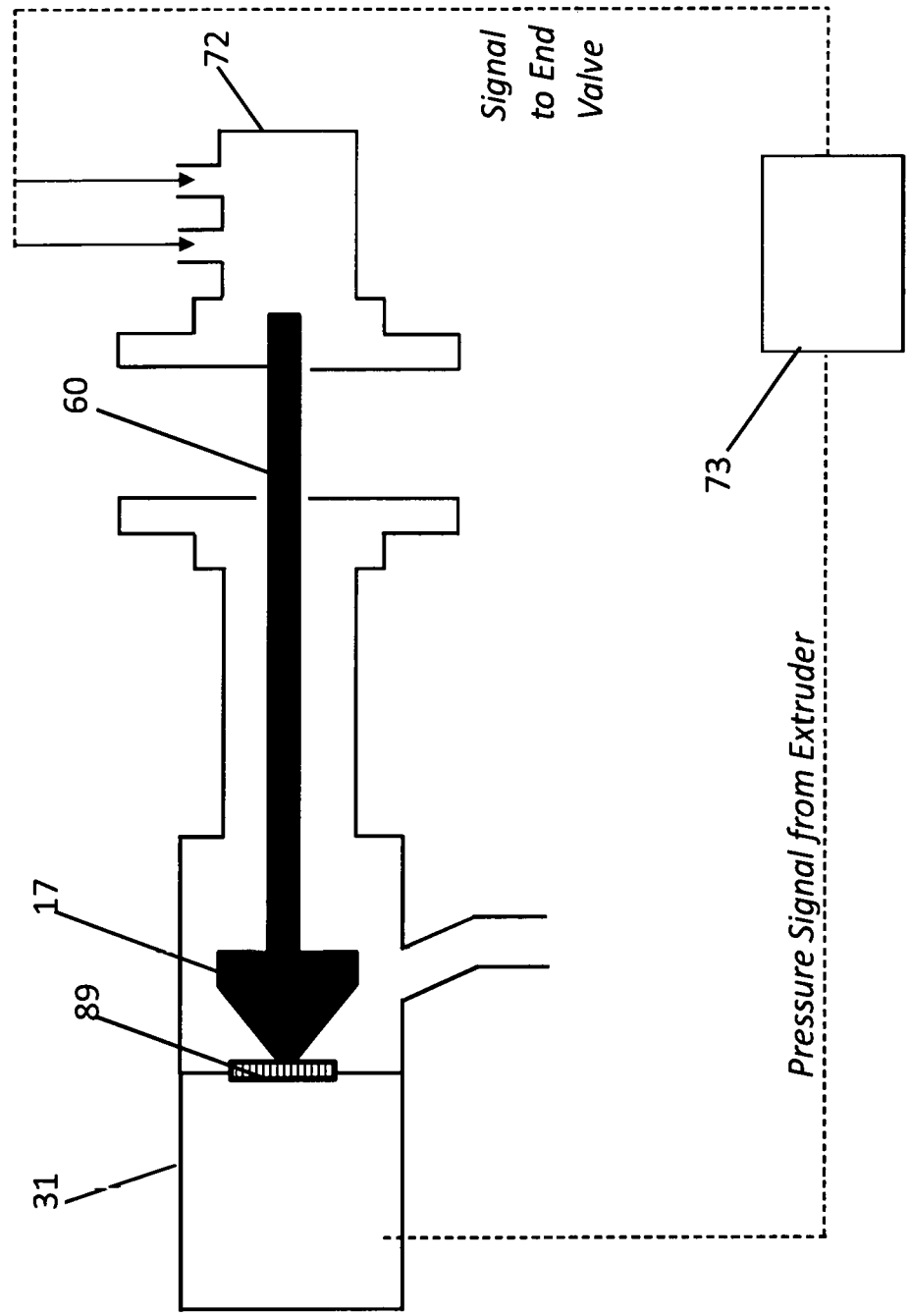
FIG. 12 is a schematic drawing of the gradual expansion venturi embodiment of FIG. 11, with the valve mostly open.
Figure 13:
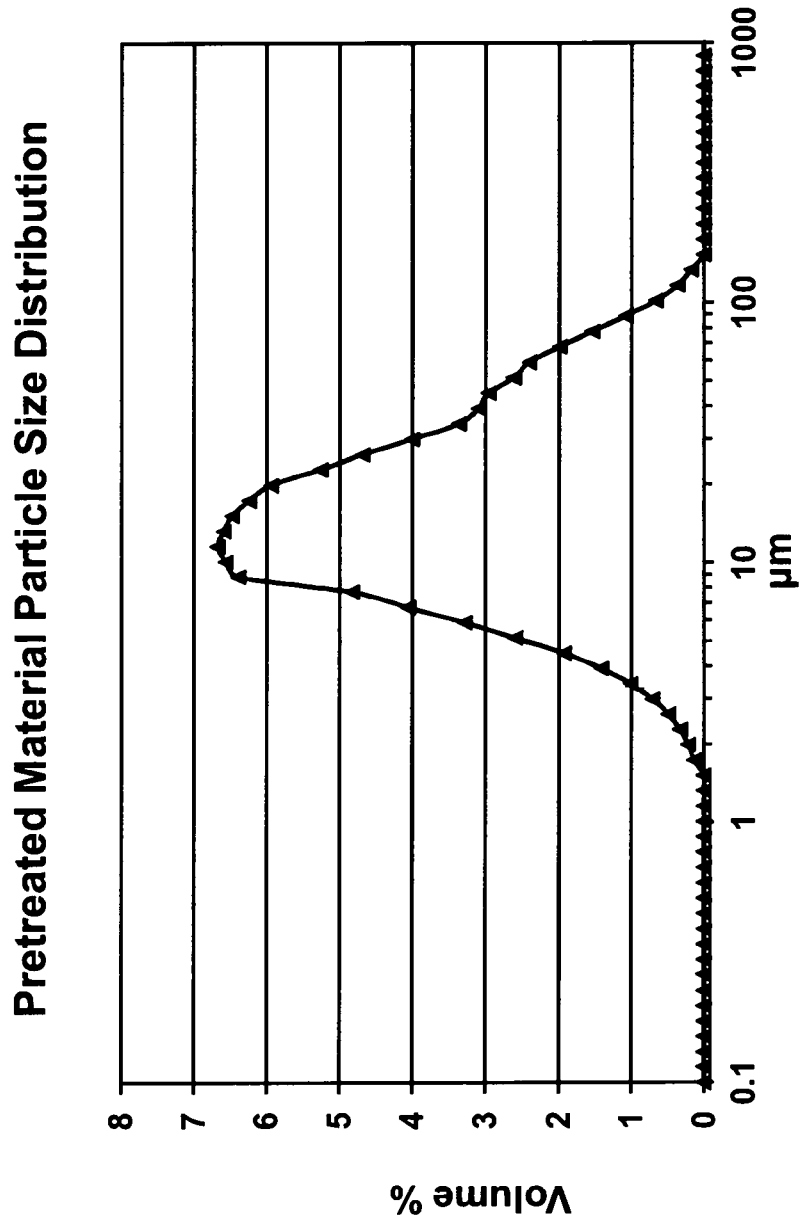
FIG. 13 is a graph showing the particle size distribution of cherry sawdust biomass following pretreatment according to an embodiment of the methods disclosed herein.

For example FIG. 12, illustrates an open valve 17 in a device as depicted in FIG. 2, which occurs when the pressure of the steam and biomass in the barrel chamber 30 (in FIG. 2) in the cylindrical barrel 31 is greater than the pressure delivered to the end valve 17. As the pressure in the chamber is reduced, the shaft pressure on the end valve 17 pushes the valve towards closure against the end of the extruder, thus reducing the release of biomass into the flash tank 70 in FIG. 2 and allowing pressure to build in the extruder again. In contrast, FIG. 11 illustrates the position of the valve 17 when it is seated in the metal or ceramic seal 89 and the shaft pressure is greater than the pressure in the extruder. In combination, FIGS. 11 and 12 depict a constant movement of the end valve forward and back as biomass is treated in the cylindrical barrel 31. In some cases, the end valve 17 is never completely closed and never completely open. Thus, the end valve remains substantially open throughout operation while a consistent pressure is maintained in the extruder as biomass is treated and released.

The application described herein can be continuous, and in some instances, the key to the outlet valve is the constant monitoring of the system pressure. There can be a feedback loop that continuously adjusts the valve opening in order to maintain a specific system pressure. See FIGS. 11 and 12. This can allow for a continuous flash process and the extruder can be continuously adjusted to maintain a desired pressure in the continuous process. Overall, this can be a more complex mechanism than traditional pretreatment discharge systems, and offers very tight, precise control of a continuous process.

Examples of variable orifice discharge valves that can be used include poppet discharge valves, knife gate valves, seat valves, butterfly valves, rotary V-port valves, and the like. Particularly useful in a smaller scale reactor, can be a piston-operated linear globe or a poppet-type discharge valve, where a hard-faced upstream side of the valve seat is a ceramic discharge orifice, and a softer downstream side of the valve seat seals against a hard-faced valve plunger, with the flow area increasing continually beyond the valve seat when the valve plunger is retracted to open.

Most suitably, the poppet-type discharge valve would incorporate a gradual expansion venturi. One embodiment of a gradual expansion venturi poppet valve that is suitable for a biomass pretreatment reactor is diagrammed in FIG. 10. This valve incorporates a conical nozzle and a metal or ceramic seat end valve arrangement. To avoid plugging, the gradual expansion venturi as exemplified in FIG. 11 (closed position) and FIG. 12 (open position) can be designed to accelerate solids through a steadily enlarging gap between the stationary cylinder 89 of the venturi and the moveable inside cone 17 of the venturi that is mounted on the end of a valve shaft 60. The discharge cylinder that the cone fits into can be generally seated into the discharge valve housing 19 at the reactor chamber exit. The venturi inside cone 89 can be the nose on the end of the valve shaft 60. The valve shaft 60 can be attached to an actuator 72 for control of movement. The actuator 72 may be any device known in the art that can be able to move the valve shaft back and forth in a horizontal motion, such as an electric, pneumatic or hydraulic motor, pneumatic valve actuator, or hydraulic piston or any other type actuator known in the art and/or provided herein. The actuator, in turn, can be within or attached to an electronic pressure regulator 73 that receives a pressure signal from the reaction chamber. For example, an E/P pressure regulator, series ED05 (Bosch Rexroth AG) can be used. When the valve shaft is in its farthest leftward position, the outer edge of the inside cone seats against the inner edge of the metal or ceramic outside cylinder to seal the discharge end of the reactor. During pretreatment, the valve shaft can be moved to the right to provide the size of opening that is desired for the flash venturi. This design can provide a flash zone of some length which expands smoothly in the direction of flow. In this design, biomass solids can be accelerated down the axis of the gradually-opening annular cone until the pressure in the chamber can be released to the point where an electronic signal from the reaction chamber results in pressure delivered to the end valve that causes the end valve to move towards the chamber, closing the gap between the flash venturi and the metal or ceramic seat.

The treated biomass can be flashed through the discharge valve moving into a pipe that leads into the flash tank. Vapors can then be released and the biomass can be cooled in preparation for pH adjustment, solids separation and/or enzymatic hydrolysis. Any typical flash tank may be used. The flash tank can be The flashing can result in a drop in pressure from the pressure maintained inside the reaction zone (e.g., the reaction zone depicted in FIGS. 1 and 2) to a pressure near atmospheric and can typically cool the biomass material to about 100° C. The temperature can then be reduced to about 50° C. which can be desired for enzymatic saccharification. The biomass can be removed from the flash tank and saccharified in batches. Generally, at this point, the C5 polymers have been hydrolyzed into oligomers or monosaccharides, depending on the amount of acid or alkali used and the temperature and pressure maintained during the treatment in the reaction zones of the barrel chamber (see FIGS. 1 and 2), as well as hydrolysis of a certain fraction or percentage of amorphous regions and C6 polymers, leaving fragmented C6 crystalline lattices opened for saccharification (e.g., enzymatic saccharification).

In some cases, the pH of a feedstock pretreated by the methods provided herein in a device as provided herein is adjusted prior to further treatment (e.g., enzymatic saccharification). Alteration of the pH of a pretreated feedstock can be accomplished by washing the feedstock (e.g., with water) one or more times to remove an alkaline or acidic substance, or other substance used or produced during pretreatment. Washing can comprise exposing the pretreated feedstock to an equal volume of water 2, 3, 4, 5, 6, 7, 8, 9, 10, 11, 12, 13, 14, 15, 16, 17, 18, 19, 20, 21, 22, 23, 24, 25 or more times. In another embodiment, a pH modifier can be added. For example, an acid, a buffer, or a material that reacts with other materials present can be added to modulate the pH of the feedstock. In one embodiment, more than one pH modifier can be used, such as one or more bases, one or more bases with one or more buffers, one or more acids, one or more acids with one or more buffers, or one or more buffers. When more than one pH modifiers are utilized, they can be added at the same time or at different times. Other non-limiting exemplary methods for neutralizing feedstocks treated with alkaline substances have been described, for example in U.S. Pat. Nos. 4,048,341; 4,182,780; and 5,693,296.

In some cases, a system can be designed to hydrolyze and remove the C5 polymers in a first reaction chamber or zone prior to subjecting them to a strong acid treatment and/or high temperatures or pressures in a second reaction chamber zone. Dilute acid and hot water treatment methods can be used to solubilize all or a portion of the hemicellulose. Methods employing alkaline reagents can be used to remove all, most, or a portion of the lignin during the pretreatment step. The remaining C6 polymers and lignin residues can be treated at high acid concentrations and high temperatures and pressures without the formation of C5 byproducts, such as furfurals and acetic acid. This would result in a mixture of C6 polymers essentially without C5 sugars and inhibitors from hydrolysis of C5 polymers. A pure C6 stream of this type is desirable to produce particular end-products such as bioplastics and to supplement starch fermentation to ethanol and other biofuels.

In some cases, a biomass or feedstock as provided herein Is subject to pretreatment using a device as provided herein such that the sugars (saccharides) produced from the pretreatment are separated and recovered for an end product as provided herein. The sugars separated and recovered can be used without a hydrolysis step. The sugars separated and recovered can be monosaccharides or saccharide oligomers or a combination thereof. The sugars (e.g., monosaccharides and/or oligomers) can be C5 and/or C6 saccharides or a combination thereof. In some cases, the biomass subjected to pretreatment for the production of saccharide oligomers in corn fiber. The saccharide oligomers produced from the corn fiber can be C5 oligomers. In one embodiment, pretreatment of biomass or feedstock as provided herein produces a pretreated feedstock concentration of soluble oligomers in the pretreated feedstock that is 1%, 10%, 15%, 20%, 25%, 30%, 35%, 40%, 45%, 50%, 55%, 60%, 65%, 70%, 75%, 80%, 85%, 90%, 95%, or 99%. Examples of soluble oligomers include, but are not limited to, cellobiose and xylobiose. In one embodiment, the parameters of the pretreatment produce a concentration of soluble oligomers in the pretreated feedstock that is 30% to 90%. In one embodiment, the parameters of the pretreatment are such that the concentration of soluble oligomers in the pretreated feedstock is 45% to 80%.

In one embodiment, the biomass recovered from pretreatment is washed and the C5 and/or soluble C6 fraction recovered from the wash water. The bound cellulose lignin fraction can be subject to further processing wherein the lignin can be solubilized with base and removed. What remains following neutralization can be a very fine microcrystalline cellulose that can be easily converted to nanocellulose and other cellulose-containing products.

Enzymatic Hydrolysis

In one embodiment, the enzyme treatment is used to hydrolyze various higher saccharides (higher molecular weight) present in biomass to lower saccharides (lower molecular weight), such as in preparation for fermentation by biocatalysts such as yeasts to produce ethanol, hydrogen, or other chemicals such as organic acids including succinic acid, formic acid, acetic acid, and lactic acid. These enzymes and/or the hydrolysate can be used in fermentations to produce various products including fuels, and other chemicals.

In one example, the process for converting biomass material into ethanol includes pretreating the biomass material (e.g., "feedstock"), hydrolyzing the pretreated biomass to convert polysaccharides to oligosaccharides, further hydrolyzing the oligosaccharides to monosaccharides, and converting the monosaccharides to biofuels and chemical products. Enzymes such as cellulases, polysaccharases, lipases, proteases, ligninases (also known as LMEs or lignases, and hemicellulases, help produce the monosaccharides can be used in the biosynthesis of fermentation endproducts. Biomass material that can be utilized includes woody plant matter, non-woody plant matter, cellulosic material, lignocellulosic material, hemicellulosic material, carbohydrates, pectin, starch, inulin, fructans, glucans, corn, algae, sugarcane, other grasses, switchgrass, bagasse, wheat straw, barley straw, rice straw, corncobs, bamboo, citrus peels, sorghum, high biomass sorghum, seed hulls, and material derived from these. The final product can then be separated and/or purified, as indicated by the properties for the desired final product. In some instances, compounds related to sugars such as sugar alcohols or sugar acids can be utilized as well.

Chemicals used in the methods of the present invention are readily available and can be purchased from a commercial supplier, such as Sigma-Aldrich. Additionally, commercial enzyme cocktails (e.g. Accellerase™ 1000, CelluSeb-TL, CelluSeb-TS, Cellic™, CTec, STARGEN™, Maxalig™, Spezyme®, Distillase®, G-Zyme®, Fermenzyme®, Fermgen™, GC 212, or Optimash™) or any other commercial enzyme cocktail can be purchased from vendors such as Specialty Enzymes & Biochemicals Co., Genencor, or Novozymes. Alternatively, enzyme cocktails can be prepared by growing one or more organisms such as for example a fungi (e.g. a *Trichoderma*, a *Saccharomyces*, a *Pichia*, a White Rot Fungus etc.), a bacteria (e.g. a *Clostridium*, or a coliform bacterium, a *Zymomonas* bacterium, *Sacharophagus degradans* etc.) in a suitable medium and harvesting enzymes produced therefrom. In some embodiments, the harvesting can include one or more steps of purification of enzymes.

In one embodiment, treatment of biomass following pretreatment of the biomass using methods and devices provided herein comprises enzyme hydrolysis. In one embodiment a biomass following pretreatment as provided herein is treated with an enzyme or a mixture of enzymes, e.g., endonucleases, exonucleases, cellobiohydrolases, cellulase, beta-glucosidases, glycoside hydrolases, glycosyltransferases, lyases, esterases and proteins containing carbohydrate-binding modules. In one embodiment, the enzyme or mixture of enzymes is one or more individual enzymes with distinct activities. In another embodiment, the enzyme or mixture of enzymes can be enzyme domains with a particular catalytic activity. For example, an enzyme with multiple activities can have multiple enzyme domains, including for example glycoside hydrolases, glycosyltransferases, lyases and/or esterases catalytic domains.

In one embodiment, enzymes that degrade polysaccharides are used for the hydrolysis of biomass and can include enzymes that degrade cellulose, namely, cellulases. Examples of some cellulases include endocellulases and exo-cellulases that hydrolyze beta-1,4-glucosidic bonds.

In one embodiment, enzymes that degrade polysaccharides are used for the hydrolysis of biomass and can include enzymes that have the ability to degrade hemicellulose, namely, hemicellulases. Hemicellulose can be a major component of plant biomass and can contain a mixture of pentoses and hexoses, for example, D-xylopyranose, L-arabinofuranose, D-mannopyranose, Dglucopyranose, D-galactopyranose, D-glucopyranosyluronic acid and other sugars. In one embodiment, enzymes that degrade polysaccharides are used for the hydrolysis of biomass and can include enzymes that have the ability to degrade pectin, namely, pectinases. In plant cell walls, the cross-linked cellulose network can be embedded in a matrix of pectins that can be covalently cross-linked to xyloglucans and certain structural proteins. Pectin can comprise homogalacturonan (HG) or rhamnogalacturonan (RH).

In one embodiment, hydrolysis of biomass includes enzymes that can hydrolyze starch. Enzymes that hydrolyze starch include alpha-amylase, glucoamylase, beta-amylase, exo-alpha-1,4-glucanase, and pullulanase.

In one embodiment, hydrolysis of biomass comprises hydrolases that can include enzymes that hydrolyze chitin, namely, chitinase. In another embodiment, hydrolases can include enzymes that hydrolyze lichen, namely, lichenase.

In one embodiment, more than one of these steps can occur at any given time. For example, hydrolysis of the pretreated feedstock and hydrolysis of the oligosaccharides can occur simultaneously, and one or more of these can occur simultaneously to the conversion of monosaccharides to a fuel or chemical.

In another embodiment, an enzyme can directly convert the polysaccharide to monosaccharides. In some instances, an enzyme can hydrolyze the polysaccharide to oligosaccharides and the enzyme or another enzyme can hydrolyze the oligosaccharides to monosaccharides.

In another embodiment, the enzymes can be added to the fermentation or they can be produced by microorganisms present in the fermentation. In one embodiment, the microorganism present in the fermentation produces some enzymes. In another embodiment, enzymes are produced separately and added to the fermentation.

For the overall conversion of pretreated biomass to final product to occur at high rates, it is generally necessary for each of the necessary enzymes for each conversion step to be present with sufficiently high activity. If one of these enzymes is missing or is present in insufficient quantities, the production rate of an end product can be reduced. The production rate can also be reduced if the microorganisms responsible for the conversion of monosaccharides to product only slowly take up monosaccharides and/or have only limited capability for translocation of the monosaccharides and intermediates produced during the conversion to end product. Additions of fractions obtained from pretreatment and/or pretreatment and hydrolysis can increase initial or overall growth rates. In another embodiment, oligomers are taken up slowly by a biocatalyst, necessitating an almost complete conversion of polysaccharides and oligomers to monomeric sugars.

In another embodiment, the enzymes of the method are produced by a biocatalyst, including a range of hydrolytic enzymes suitable for the biomass materials used in the fermentation methods. In one embodiment, a biocatalyst is grown under conditions appropriate to induce and/or promote production of the enzymes needed for the saccharification of the polysaccharide present. The production of these enzymes can occur in a separate vessel, such as a seed fermentation vessel or other fermentation vessel, or in the production fermentation vessel where ethanol production occurs. When the enzymes are produced in a separate vessel, they can, for example, be transferred to the production fermentation vessel along with the cells, or as a relatively cell free solution liquid containing the intercellular medium with the enzymes. When the enzymes are produced in a separate vessel, they can also be dried and/or purified prior to adding them to the hydrolysis or the production fermentation vessel. The conditions appropriate for production of the enzymes are frequently managed by growing the cells in a medium that includes the biomass that the cells will be expected to hydrolyze in subsequent fermentation steps. Additional medium components, such as salt supplements, growth factors, and cofactors including, but not limited to phytate, amino acids, and peptides can also assist in the production of the enzymes utilized by the microorganism in the production of the desired products.

Fermentation

The present disclosure also provides a fermentative mixture comprising: a cellulosic feedstock pre-treated with an alkaline or acid substance and at a temperature of from about 160° C. to about 210° C.; subsequently hydrolyzed with an enzyme mixture, and a microorganism capable of fermenting a five-carbon sugar and/or a six-carbon sugar. In one embodiment, the five-carbon sugar is xylose, arabinose, or a combination thereof. In one embodiment, the six-carbon sugar is glucose, galactose, mannose, or a combination thereof. In one embodiment, the alkaline substance is NaOH. In some embodiments, NaOH is added at a concentration of about 0.5% to about 2% by weight of the feedstock. In one embodiment, the acid is equal to or less than 2% HCl or $H_2SO_4$. In one embodiment, the microorganism is a *Rhodococcus* strain, a *Clostridium* strain, a *Trichoderma* strain, a *Saccharomyces* strain, a *Zymomonas* strain, or another microorganism suitable for fermentation of biomass. In another embodiment, the fermentation process comprises fermentation of the biomass using a microorganism that is *Clostridium phytofermentans, Clostridium algidixylanolyticum, Clostridium xylanolyticum, Clostridium cellulovorans, Clostridium cellulolyticum, Clostridium thermocellum, Clostridium josui, Clostridium papyrosolvens, Clostridium cellobioparum, Clostridium hungatei, Clostridium cellulosi, Clostridium stercorarium, Clostridium termitidis, Clostridium thermocopriae, Clostridium celerecrescens, Clostridium polysaccharolyticum, Clostridium populeti, Clostridium lentocellum, Clostridium chartatabidum, Clostridium aldrichii, Clostridium herbivorans, Acetivibrio cellulolyticus, Bacteroides cellulosolvens, Caldicellulosiruptor saccharolyticum, Rhodococcus opacus, Ruminococcus albus, Ruminococcus flavefaciens, Fibrobacter succinogenes, Eubacterium cellulosolvens, Butyrivibrio fibrisolvens, Anaerocellum thermophilum, Halocella cellulolytica, Thermoanaerobacterium thermosaccharolyticum, Sacharophagus degradans,* or *Thermoanaerobacterium saccharolyticum*. In still another embodiment, the microorganism is genetically modified to enhance activity of one or more hydrolytic enzymes, such as a genetically-modified *Saccharomyces cerevisiae*.

In one embodiment a wild type or a genetically-improved microorganism can be used for chemical production by fermentation. Methods to produce a genetically-improved strain can include genetic modification, protoplast fusion, mutagenesis, and adaptive processes, such as directed evolution. For example, yeasts can be genetically-modified to ferment C5 sugars. Other useful yeasts are species of *Candida, Cryptococcus, Debaryomyces, Deddera, Hanseniaspora, Kluyveromyces, Pichia, Schizosaccharomyces,* and *Zygosaccharomyces. Rhodococcus* strains, such as *Rhodococcus opacus* variants are a source of triacylglycerols and other storage lipids. (See, e.g., Waltermann, et al., Microbiology 146:1143-1149 (2000)). Other useful organisms for fermentation include, but are not limited to, yeasts, especially *Saccaromyces* strains and bacteria such as *Clostridium phytofermentans, Thermoanaerobacter ethanolicus, Clostridium thermocellum, Clostridium beijerinickii, Clostridium acetobutylicum, Clostridium tyrobutyricum, Clostridium thermobutyricum, Thermoanaerobacterium saccharolyticum, Thermoanaerobacter thermohydrosulfuricus, Clostridium acetobutylicum, Moorella* ssp., *Carboxydocella* ssp., *Zymomonas mobilis*, recombinant *E. Coli, Klebsiella oxytoca, Rhodococcus opacus* and *Clostridium beijerickii*.

An advantage of yeasts is their ability to grow under conditions that include elevated ethanol concentration, high sugar concentration, low sugar concentration, and/or operate under anaerobic conditions. These characteristics, in various combinations, can be used to achieve operation with long or short fermentation cycles and can be used in combination with batch fermentations, fed batch fermentations, self-seeding/partial harvest fermentations, and recycle of cells from the final fermentation as inoculum.

In one embodiment, fed-batch fermentation is performed on the pre-treated and subsequently treated biomass to produce a fermentation end-product, such as alcohol, ethanol, organic acid, succinic acid, TAG, or hydrogen. In one embodiment, the fermentation process comprises simultaneous hydrolysis and fermentation (SSF) of the biomass using one or more microorganisms such as a *Rhodococcus* strain, a *Clostridium* strain, a *Trichoderma* strain, a *Saccharomyces* strain, a *Zymomonas* strain, or another microorganism suitable for fermentation of biomass. In another embodiment, the fermentation process comprises simultaneous hydrolysis and fermentation of the biomass using a microorganism that is *Clostridium algidixylanolyticum, Clostridium xylanolyticum, Clostridium cellulovorans, Clostridium cellulolyticum, Clostridium thermocellum, Clostridium josui, Clostridium papyrosolvens, Clostridium cellobioparum, Clostridium hungatei, Clostridium cellulosi, Clostridium stercorarium, Clostridium termitidis, Clostridium thermocopriae, Clostridium celerecrescens, Clostridium polysaccharolyticum, Clostridium populeti, Clostridium lentocellum, Clostridium chartatabidum, Clostridium aldrichii, Clostridium herbivorans, Clostridium phytofermentans, Acetivibrio cellulolyticus, Bacteroides cellulosolvens, Caldicellulosiruptor saccharolyticum, Ruminococcus albus, Ruminococcus flavefaciens, Fibrobacter succinogenes, Eubacterium cellulosolvens, Butyrivibrio fibrisolvens, Anaerocellum thermophilum, Halocella cellulolytica, Thermoanaerobacterium thermosaccharolyticum, Sacharophagus degradans,* or *Thermoanaerobacterium saccharolyticum*.

In one embodiment, the fermentation process can include separate hydrolysis and fermentation (SHF) of a biomass with one or more enzymes, such as a xylanases, endo-1,4-beta-xylanases, xylosidases, beta-D-xylosidases, cellulases, hemicellulases, carbohydrases, glucanases, endoglucanases, endo-1,4-beta-glucanases, exoglucanases, glucosidases, beta-D-glucosidases, amylases, cellobiohydrolases, exocellobiohydrolases, phytases, proteases, peroxidase, pectate lyases, galacturonases, or laccases. In one embodiment one or more enzymes used to treat a biomass is thermostable. In another embodiment a biomass is treated with one or more enzymes, such as those provided herein, prior to fermentation. In another embodiment a biomass is treated with one or more enzymes, such as those provided herein, during fermentation. In another embodiment a biomass is treated with one or more enzymes, such as those provided herein, prior to fermentation and during fermentation. In another embodiment an enzyme used for hydrolysis of a biomass is the same as those added during fermentation. In another embodiment an enzyme used for hydrolysis of biomass is different from those added during fermentation.

In some embodiments, fermentation can be performed in an apparatus such as bioreactor, a fermentation vessel, a stirred tank reactor, or a fluidized bed reactor. In one embodiment the treated biomass can be supplemented with suitable chemicals to facilitate robust growth of the one or more fermenting organisms. In one embodiment a useful supplement includes but is not limited to, a source of nitrogen and/or amino acids such as yeast extract, cysteine, or ammonium salts (e.g. nitrate, sulfate, phosphate etc.); a source of simple carbohydrates such as corn steep liquor, and malt syrup; a source of vitamins such as yeast extract; buffering agents such as salts (including but not limited to citrate salts, phosphate salts, or carbonate salts); or mineral nutrients such as salts of magnesium, calcium, or iron. In some embodiments redox modifiers are added to the fermentation mixture including but not limited to cysteine or mercaptoethanol.

In one embodiment the titer and/or productivity of fermentation end-product production by a microorganism is improved by culturing the microorganism in a medium comprising one or more compounds comprising hexose and/or pentose sugars. In one embodiment, a process comprises conversion of a starting material (such as a biomass) to a biofuel, such as one or more alcohols. In one embodiment, methods of the invention comprise contacting substrate comprising both hexose (e.g. glucose, cellobiose) and pentose (e.g. xylose, arabinose) saccharides with a microorganism that can hydrolyze C5 and C6 saccharides to produce ethanol. In another embodiment, methods of the invention comprise contacting substrate comprising both hexose (e.g. glucose, cellobiose) and pentose (e.g. xylose, arabinose) saccharides with *R. opacus* to produce TAG.

In some embodiments of the present invention, batch fermentation with a microorganism of a mixture of hexose and pentose saccharides using the methods of the present invention provides uptake rates of about 0.1-8 g/L/h or more of hexose and about 0.1-8 g/L/h or more of pentose (xylose, arabinose, etc.). In some embodiments of the present invention, batch fermentation with a microorganism of a mixture of hexose and pentose saccharides using the methods of the present invention provides uptake rates of about 0.1, 0.2, 0.4, 0.5, 0.6 0.7, 0.8, 1, 2, 3, 4, 5, or 6 g/L/h or more of hexose and about 0.1, 0.2, 0.4, 0.5, 0.6 0.7, 0.8, 1, 2, 3, 4, 5, or 6 g/L/h or more of pentose.

In one embodiment, a method for production of ethanol or another alcohol produces about 10 g/l to 120 gain 40 hr or less. In another embodiment a method for production of ethanol produces about 10 g/l, 11 g/L, 12 g/L, 13 g/L, 14 g/L, 15 g/L, 16 g/L, 17 g/L, 18 g/L, 19 g/L, 20 g/L, 21 g/L, 22 g/L, 23 g/L, 24 g/L, 25 g/L, 26 g/L, 27 g/L, 28 g/L, 29 g/L, 30 g/L, 31 g/L, 32 g/L, 33 g/L, 34 g/L, 35 g/L, 36 g/L, 37 g/L, 38 g/L, 39 g/L, 40 g/L, 41 g/L, 42 g/L, 43 g/L, 44 g/L, 45 g/L, 46 g/L, 47 g/L, 48 g/L, 49 g/L, 50 g/L, 51 g/L, 52 g/L, 53 g/L, 54 g/L, 55 g/L, 56 g/L, 57 g/L, 58 g/L, 59 g/L, 60 g/L, 61 g/L, 62 g/L, 63 g/L, 64 g/L, 65 g/L, 66 g/L, 67 g/L, 68 g/L, 69 g/L, 70 g/L, 71 g/L, 72 g/L, 73 g/L, 74 g/L, 75 g/L, 76 g/L, 77 g/L, 78 g/L, 79 g/L, 80 g/L, 81 g/L, 82 g/L, 83 g/L, 84 g/L, 85 g/L, 86 g/L, 87 g/L, 88 g/L, 89 g/L, 90 g/L, 91 g/L, 92 g/L, 93 g/L, 94 g/L, 95 g/L, 96 g/L, 97 g/L, 98 g/L, 99 g/L, 100 g/L, 110 g/l, 120 g/l, or more alcohol in 40 hr by the fermentation of biomass. In another embodiment, alcohol is produced by a method comprising simultaneous fermentation of hexose and pentose saccharides. In another embodiment, alcohol is produced by a microorganism comprising simultaneous fermentation of hexose and pentose saccharides.

In another embodiment, the level of a medium component is maintained at a desired level by adding additional medium component as the component is consumed or taken up by the organism. Examples of medium components included, but are not limited to, carbon substrate, nitrogen substrate, vitamins, minerals, growth factors, cofactors, and biocatalysts. The medium component can be added continuously or at regular or irregular intervals. In one embodiment, additional medium component is added prior to the complete depletion of the medium component in the medium. In one embodiment, complete depletion can effectively be used, for example to initiate different metabolic pathways, to simplify downstream operations, or for other reasons as well. In one embodiment, the medium component level is allowed to vary by about 10% around a midpoint, in one embodiment, it is allowed to vary by about 30% around a midpoint, and in one embodiment, it is allowed to vary by 60% or more around a midpoint. In one embodiment, the medium component level is maintained by allowing the medium component to be depleted to an appropriate level, followed by increasing the medium component level to another appropriate level. In one embodiment, a medium component, such as vitamin, is added at two different time points during fermentation process. For example, one-half of a total amount of vitamin is added at the beginning of fermentation and the other half is added at midpoint of fermentation.

In another embodiment, the nitrogen level is maintained at a desired level by adding additional nitrogen-containing material as nitrogen is consumed or taken up by the organism. The nitrogen-containing material can be added continuously or at regular or irregular intervals. Useful nitrogen levels include levels of about 5 to about 10 g/L. In one embodiment levels of about 1 to about 12 g/L can also be usefully employed. In another embodiment levels, such as about 0.5, 0.1 g/L or even lower, and higher levels, such as about 20, 30 g/L or even higher are used. In another embodiment a useful nitrogen level is about 0.01, 0.05, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22 23, 24, 25, 26, 27, 28, 29 or 30 g/L. Nitrogen can be supplied as a simple nitrogen-containing material, such as an ammonium compounds (e.g. ammonium sulfate, ammonium hydroxide, ammonia, ammonium nitrate, or any other compound or mixture containing an ammonium moiety), nitrate or nitrite compounds (e.g. potassium, sodium, ammonium, calcium, or other compound or mixture containing a nitrate or nitrite moiety), or as a more complex nitrogen-containing material, such as amino acids, proteins, hydrolyzed protein, hydrolyzed yeast, yeast extract, dried brewer's yeast, yeast hydrolysates, distillers' grains, soy protein, hydrolyzed soy protein, fermentation products, and processed or corn steep powder or unprocessed protein-rich vegetable or animal matter, including those derived from bean, seeds, soy, legumes, nuts, milk, pig, cattle, mammal, fish, as well as other parts of plants and other types of animals. Nitrogen-containing materials useful in various embodiments also include materials that contain a nitrogen-containing material, including, but not limited to mixtures of a simple or more complex nitrogen-containing material mixed with a carbon source, another nitrogen-containing material, or other nutrients or non-nutrients, and AFEX treated plant matter.

In another embodiment, the carbon level is maintained at a desired level by adding sugar compounds or material containing sugar compounds ("Sugar-Containing Material") as sugar is consumed or taken up by the organism. The sugar-containing material can be added continuously or at regular or irregular intervals. In one embodiment, additional sugar-containing material is added prior to the complete depletion of the sugar compounds available in the medium.

In one embodiment, complete depletion can effectively be used, for example to initiate different metabolic pathways, to simplify downstream operations, or for other reasons as well. In one embodiment, the carbon level (as measured by the grams of sugar present in the sugar-containing material per liter of broth) is allowed to vary by about 10% around a midpoint, in one embodiment, it is allowed to vary by about 30% around a midpoint, and in one embodiment, it is allowed to vary by 60% or more around a midpoint. In one embodiment, the carbon level is maintained by allowing the carbon to be depleted to an appropriate level, followed by increasing the carbon level to another appropriate level. In some embodiments, the carbon level can be maintained at a level of about 5 to about 120 g/L. However, levels of about 30 to about 100 g/L can also be usefully employed as well as levels of about 60 to about 80 g/L. In one embodiment, the carbon level is maintained at greater than 25 g/L for a portion of the culturing. In another embodiment, the carbon level is maintained at about 5 g/L, 6 g/L, 7 g/L, 8 g/L, 9 g/L, 10 g/L, 11 g/L, 12 g/L, 13 g/L, 14 g/L, 15 g/L, 16 g/L, 17 g/L, 18 g/L, 19 g/L, 20 g/L, 21 g/L, 22 g/L, 23 g/L, 24 g/L, 25 g/L, 26 g/L, 27 g/L, 28 g/L, 29 g/L, 30 g/L, 31 g/L, 32 g/L, 33 g/L, 34 g/L, 35 g/L, 36 g/L, 37 g/L, 38 g/L, 39 g/L, 40 g/L, 41 g/L, 42 g/L, 43 g/L, 44 g/L, 45 g/L, 46 g/L, 47 g/L, 48 g/L, 49 g/L, 50 g/L, 51 g/L, 52 g/L, 53 g/L, 54 g/L, 55 g/L, 56 g/L, 57 g/L, 58 g/L, 59 g/L, 60 g/L, 61 g/L, 62 g/L, 63 g/L, 64 g/L, 65 g/L, 66 g/L, 67 g/L, 68 g/L, 69 g/L, 70 g/L, 71 g/L, 72 g/L, 73 g/L, 74 g/L, 75 g/L, 76 g/L, 77 g/L, 78 g/L, 79 g/L, 80 g/L, 81 g/L, 82 g/L, 83 g/L, 84 g/L, 85 g/L, 86 g/L, 87 g/L, 88 g/L, 89 g/L, 90 g/L, 91 g/L, 92 g/L, 93 g/L, 94 g/L, 95 g/L, 96 g/L, 97 g/L, 98 g/L, 99 g/L, 100 g/L, 101 g/L, 102 g/L, 103 g/L, 104 g/L, 105 g/L, 106 g/L, 107 g/L, 108 g/L, 109 g/L, 110 g/L, 111 g/L, 112 g/L, 113 g/L, 114 g/L, 115 g/L, 116 g/L, 117 g/L, 118 g/L, 119 g/L, 120 g/L, 121 g/L, 122 g/L, 123 g/L, 124 g/L, 125 g/L, 126 g/L, 127 g/L, 128 g/L, 129 g/L, 130 g/L, 131 g/L, 132 g/L, 133 g/L, 134 g/L, 135 g/L, 136 g/L, 137 g/L, 138 g/L, 139 g/L, 140 g/L, 141 g/L, 142 g/L, 143 g/L, 144 g/L, 145 g/L, 146 g/L, 147 g/L, 148 g/L, 149 g/L, or 150 g/L.

The carbon substrate, like the nitrogen substrate, is necessary for cell production and enzyme production, but unlike the nitrogen substrate, it serves as the raw material for production of end products. Frequently, more carbon substrate can lead to greater production of end products. In another embodiment, it can be advantageous to operate with the carbon level and nitrogen level related to each other for at least a portion of the fermentation time. In one embodiment, the ratio of carbon to nitrogen is maintained within a range of about 30:1 to about 10:1. In another embodiment, the ratio of carbon nitrogen is maintained from about 20:1 to about 10:1 or more preferably from about 15:1 to about 10:1. In another embodiment the ratio of carbon nitrogen is about 30:1, 29:1, 28:1, 27:1, 26:1, 25:1, 24:1, 23:1, 22:1, 21:1, 20:1, 19:1, 18:1, 17:1, 16:1, 15:1, 14:1, 13:1, 12:1, 11:1, 10:1, 9:1, 8:1, 7:1, 6:1, 5:1, 4:1, 3:1, 2:1, or 1:1.

Maintaining the ratio of carbon and nitrogen ratio within particular ranges can result in benefits to the operation such as the rate of metabolism of carbon substrate, which depends on the amount of carbon substrate and the amount and activity of enzymes present, being balanced to the rate of end product production. Balancing the carbon to nitrogen ratio can, for example, facilitate the sustained production of these enzymes such as to replace those which have lost activity.

In another embodiment, the amount and/or timing of carbon, nitrogen, or other medium component addition can be related to measurements taken during the fermentation. For example, the amount of monosaccharides present, the amount of insoluble polysaccharide present, the polysaccharase activity, the amount of product present, the amount of cellular material (for example, packed cell volume, dry cell weight, etc.) and/or the amount of nitrogen (for example, nitrate, nitrite, ammonia, urea, proteins, amino acids, etc.) present can be measured. The concentration of the particular species, the total amount of the species present in the fermentor, the number of hr the fermentation has been running, and the volume of the fermentor can be considered. In various embodiments, these measurements can be compared to each other and/or they can be compared to previous measurements of the same parameter previously taken from the same fermentation or another fermentation. Adjustments to the amount of a medium component can be accomplished such as by changing the flow rate of a stream containing that component or by changing the frequency of the additions for that component. For example, the amount of saccharide can be increased when the cell production increases faster than the end product production. In another embodiment the amount of nitrogen can be increased when the enzyme activity level decreases.

In another embodiment, a fed batch operation can be employed, wherein medium components and/or fresh cells are added during the fermentation without removal of a portion of the broth for harvest prior to the end of the fermentation. In one embodiment a fed-batch process is based on feeding a growth limiting nutrient medium to a culture of microorganisms. In one embodiment the feed medium is highly concentrated to avoid dilution of the bioreactor. In another embodiment the controlled addition of the nutrient directly affects the growth rate of the culture and avoids overflow metabolism such as the formation of side metabolites. In one embodiment the growth limiting nutrient is a nitrogen source or a saccharide source.

In various embodiments, particular medium components can have beneficial effects on the performance of the fermentation, such as increasing the titer of desired products, or increasing the rate that the desired products are produced. Specific compounds can be supplied as a specific, pure ingredient, such as a particular amino acid, or it can be supplied as a component of a more complex ingredient, such as using a microbial, plant or animal product as a medium ingredient to provide a particular amino acid, promoter, cofactor, or other beneficial compound. In some cases, the particular compound supplied in the medium ingredient can be combined with other compounds by the organism resulting in a fermentation-beneficial compound. One example of this situation would be where a medium ingredient provides a specific amino acid which the organism uses to make an enzyme beneficial to the fermentation. Other examples can include medium components that are used to generate growth or product promoters, etc. In such cases, it can be possible to obtain a fermentation-beneficial result by supplementing the enzyme, promoter, growth factor, etc. or by adding the precursor. In some situations, the specific mechanism whereby the medium component benefits the fermentation is not known, only that a beneficial result is achieved.

In one embodiment, a fermentation to produce a fuel is performed by culturing a strain of R. opacus biocatalyst in a medium having a supplement of lignin component and a concentration of one or more carbon sources. The resulting production of end product such as TAG can be up to 1-fold, 2-fold, 3-fold, 4-fold, 5-fold, 6-fold, 7-fold, 8-fold, 9-fold, and in some cases up to 10-fold and higher in volumetric productivity than a process using only the addition of a relatively pure saccharide source, and can achieve a carbon conversion efficiency approaching the theoretical maximum. The theoretical maximum can vary with the substrate and product. For example, the generally accepted maximum efficiency for conversion of glucose to ethanol is 0.51 g ethanol/g glucose. In one embodiment a biocatalyst can produce about 40-100% of a theoretical maximum yield of ethanol. In another embodiment, a biocatalyst can produce up to about 40%, 50%, 60%, 70%, 80%, 90%, 95% and even 100% of the theoretical maximum yield of ethanol. In one embodiment a biocatalyst can produce up to about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.99%, or 100% of a theoretical maximum yield of a fuel. It can be possible to obtain a fermentation-beneficial result by supplementing the medium with a pretreatment or hydrolysis component. In some situations, the specific mechanism whereby the medium component benefits the fermentation is not known, only that a beneficial result is achieved.

Various embodiments offer benefits relating to improving the titer and/or productivity of fermentation end-product production by a biocatalyst by culturing the organism in a medium comprising one or more compounds comprising particular fatty acid moieties and/or culturing the organism under conditions of controlled pH.

In one embodiment, the pH of the medium is controlled at less than about pH 7.2 for at least a portion of the fermentation. In one embodiment, the pH is controlled within a range of about pH 3.0 to about 7.1 or about pH 4.5 to about 7.1, or about pH 5.0 to about 6.3, or about pH 5.5 to about 6.3, or about pH 6.0 to about 6.5, or about pH 5.5 to about 6.9 or about pH 6.2 to about 6.7. The pH can be controlled by the addition of a pH modifier. In one embodiment, a pH modifier is an acid, a base, a buffer, or a material that reacts with other materials present to serve to raise of lower the pH. In one embodiment, more than one pH modifier can be used, such as more than one acid, more than one base, one or more acid with one or more bases, one or more acids with one or more buffers, one or more bases with one or more buffers, or one or more acids with one or more bases with one or more buffers. When more than one pH modifiers are utilized, they can be added at the same time or at different times. In one embodiment, one or more acids and one or more bases can be combined, resulting in a buffer. In one embodiment, media components, such as a carbon source or a nitrogen source can also serve as a pH modifier; suitable media components include those with high or low pH or those with buffering capacity. Exemplary media components include acid- or base-hydrolyzed plant polysaccharides having with residual acid or base, AFEX treated plant material with residual ammonia, lactic acid, corn steep solids or liquor.

In one embodiment, a constant pH can be utilized throughout the fermentation. In one embodiment, the timing and/or amount of pH reduction can be related to the growth conditions of the cells, such as in relation to the cell count, the end product produced, the end product present, or the rate of end product production. In one embodiment, the pH reduction can be made in relation to physical or chemical properties of the fermentation, such as viscosity, medium composition, gas production, off gas composition, etc.

Recovery of Fermentive End Products

In another aspect, methods are provided for the recovery of the fermentive end products, such as an alcohol (e.g. ethanol, propanol, methanol, butanol, etc.) another biofuel or chemical product. In one embodiment, broth will be harvested at some point during of the fermentation, and fermentive end product or products will be recovered. The broth with end product to be recovered will include both end product and impurities. The impurities include materials such as water, cell bodies, cellular debris, excess carbon substrate, excess nitrogen substrate, other remaining nutrients, other metabolites, and other medium components or digested medium components. During the course of processing the broth, the broth can be heated and/or reacted with various reagents, resulting in additional impurities in the broth.

In one embodiment, the processing steps to recover end product frequently includes several separation steps, including, for example, distillation of a high concentration alcohol material from a less pure alcohol-containing material. In one embodiment, the high concentration ethanol material can be further concentrated to achieve very high concentration alcohol, such as 98% or 99% or 99.5% (wt.) or even higher. Other separation steps, such as filtration, centrifugation, extraction, adsorption, etc. can also be a part of some recovery processes for alcohol as a product or biofuel, or other biofuels or chemical products.

In one embodiment a process can be scaled to produce commercially useful biofuels. In another embodiment biocatalyst is used to produce an alcohol, e.g., ethanol, butanol, propanol, methanol, or a fuel such as hydrocarbons hydrogen, TAG, and hydroxy compounds. In another embodiment biocatalyst is used to produce a carbonyl compound such as an aldehyde or ketone (e.g. acetone, formaldehyde, 1-propanal, etc.), an organic acid, a derivative of an organic acid such as an ester (e.g. wax ester, glyceride, etc.), 1, 2-propanediol, 1, 3-propanediol, lactic acid, formic acid, acetic acid, succinic acid, pyruvic acid, or an enzyme such as a cellulase, polysaccharase, lipases, protease, ligninase, and hemicellulase.

TAG biosynthesis is widely distributed in nature and the occurrence of TAG as reserve compounds is widespread among plants, animals, yeast and fungi. In contrast, however, TAGs have not been regarded as common storage compounds in bacteria. Biosynthesis and accumulation of TAGs have been described only for a few bacteria belonging to the actinomycetes group, such as genera of *Streptomyces, Nocardia, Rhodococcus, Mycobacterium, Dietzia* and *Gordonia*, and, to a minor extent, also in a few other bacteria, such as *Acinetobacter baylyi* and *Alcanivorax borkumensis*. Since the mid-1990's, TAG production in hydrocarbon-degrading strains of those genera has been frequently reported. TAGs are stored in spherical lipid bodies as intracellular inclusions, with the amounts depending on the respective species, cultural conditions and growth phase. Commonly, the important factor for the production of TAGs is the amount of nitrogen that is supplied to the culture medium. The excess carbon, which is available to the culture after nitrogen exhaustion, continues to be assimilated by the cells and, by virtue of oleaginous bacteria possessing the requisite enzymes, is converted directly into lipid. The compositions and structures of bacterial TAG molecules vary considerably depending on the bacterium and on the cultural conditions, especially the carbon sources. See, Brigham C J, et al. (2011) J Microbial Biochem Technol S3:002.

In one embodiment, useful biochemicals can be produced from non-food plant biomass, with a steam or hot-water extraction technique that is carried out by contacting a charge of non-food plant pretreated biomass material such as corn stover or sorghum with water and/or acid (with or without additional process enhancing compounds or materials), in a pressurized vessel at an elevated temperature up to about 160-220° C. and at a pH below about 7.0, to yield an aqueous (extract solution) mixture of useful sugars including long-chain saccharides (sugars), acetic acid, and lignin, while leaving the structural (cellulose and lignin) portion of the lignocellulosic material largely intact. In combination, these potential inhibitory chemicals especially sugar degradation products are low, and the plant derived nutrients that are naturally occurring lignocellulosic-based components are also recovered that are beneficial to a C5 and C6 fermenting organism. Toward this objective, the aqueous extract is concentrated (by centrifugation, filtration, solvent extraction, flocculation, evaporation), by producing a concentrated sugar stream, apart from the other hemicellulose (C5 rich) and cellulosic derived sugars (C6 rich) that are channeled into a fermentable stream.

In another embodiment, following enzyme/acid hydrolysis, additional chemical compounds that are released are recovered with the sugar stream resulting in a short-chain sugar solution containing xylose, mannose, arabinose, rhamnose, galactose, and glucose (5 and 6-carbon sugars). The sugar stream, now significantly rich in C5 and C6 substances can be converted by microbial fermentation or chemical catalysis into such products as triacylglycerol or TAG and further refined to produce stream rich in JP8 or jet fuels. If C5 sugar percentage correction has not been performed, it can be performed before fermentation to satisfy desired combination of C5 and C6 sugars for the fermentation organism and corresponding end product.

Specific Embodiments

A number of methods and systems are disclosed herein. Specific exemplary embodiments of these methods and systems are disclosed below.

Embodiment 1

An industrial scale method for pretreating biomass, the method comprising: (a) feeding the biomass into an extrusion system comprising: (i) a barrel defining an inner chamber comprising a feeder zone and a reaction zone; and (ii) one or more rotatable screws configured to move the biomass through the extrusion system from the feeder zone through the reaction zone, wherein the one or more rotatable screws comprise section elements configured to form: (1) a preconditioning section in the feeder zone that produces a homogenized biomass by reducing particle size of the biomass and evenly distributing water within the biomass, and (2) a high pressure zone that compacts the homogenized biomass to form a steam impervious plug separating the feeder zone and the reaction zone; and (b) treating the biomass at an elevated temperature and pressure within the reaction zone for less than about one minute to produce a pretreated biomass composition comprising a liquid/solids fraction comprising monosaccharides and solid particles comprising cellulose and/or lignin.

Embodiment 2

The method of embodiment 1, wherein the extrusion system is configured to pretreat the biomass continuously while maintaining the steam impervious plug for at least about 1 hr, at least about 2 hrs, at least about 4 hrs, at least about 5 hrs, at least about 6 hrs, at least about 8 hrs, at least about 10 hrs, at least about 12 hrs, at least about 13 hrs, at least about 14 hrs, at least about 15 hrs, at least about 16 hrs, at least about 17 hrs, or at least about 18 hrs.

Embodiment 3

The method of embodiment 1 or 2, wherein the extrusion is configured to pretreat the biomass continuously while maintaining the steam impervious plug for at least about 15 hrs.

Embodiment 4

The method of any one of embodiments 1-3, wherein the extrusion system is configured to pretreat the biomass at a feeding rate of from about 60 to about 350 dry kg/hr.

Embodiment 5

The method of any one of embodiments 1-4, wherein the liquid fraction comprises C5 monosaccharides and C6 monosaccharides in a w/w ratio of at least about 3.0:1, at least about 3.1:1, at least about 3.2:1, at least about 3.3:1, at least about 3.4:1, at least about 3.5:1, at least about 3.6:1, at least about 3.7:1, at least about 3.8:1, at least about 3.9:1, at least about 3.91:1, at least about 3.92:1, at least about 3.93:1, at least about 3.94:1, at least about 3.95:1, at least about 3.96:1, or at least about 4:1.

Embodiment 6

The method of any one of embodiments 1-5, wherein the liquid fraction comprises C5 monosaccharides and C6 monosaccharides in a w/w ratio of at least about 3.5:1.

Embodiment 7

The method of any one of embodiments 1-6, wherein the liquid fraction comprises C5 monosaccharides and C6 monosaccharides in a w/w ratio of at least about 3.9:1.

Embodiment 8

The method of any one of embodiments 1-7, wherein the steam impervious plug is impervious to steam at a pressure of at least 1000 psi.

Embodiment 9

The method of any one of embodiments 1-8, wherein the preconditioning section reduces particle size of the biomass by at least about 2%, at least about 5%, at least about 10%, at least about 20%, at least about 30%, at least about 40%, or at least about 50%.

Embodiment 10

The method of any one of embodiments 1-9, wherein the homogenized biomass has an average particle size about: 5-500 μm, 10-200 μm, 10-100 μm, or 15-50 μm.

Embodiment 11

The method of any one of embodiments 1-10, wherein the homogenized biomass has a particle size of about 10-100 µm.

Embodiment 12

The method of any one of embodiments 1-11, wherein the one or more rotatable screws further comprise one or more section elements that are configured to form one or more steam-permeable plugs.

Embodiment 13

The method of any one of embodiments 1-12, wherein the extrusion system comprises one, two, or three rotatable screws.

Embodiment 14

The method of embodiment 13, wherein the extrusion system comprises two rotatable screws.

Embodiment 15

The method of any one of embodiments 1-14, wherein the biomass is fed into the extrusion system at a rate that is at least about 1 dry metric ton per day (MT/day), 2 dry MT/day, 3 dry MT/day, 4 dry MT/day, 5 dry MT/day, 7.5 dry MT/day, 10 dry MT/day, 15 dry MT/day, 20 dry MT/day, 25 dry MT/day, 50 dry MT/day, 75 dry MT/day, dry 100 MT/day, 150 dry MT/day, or 200 dry MT/day.

Embodiment 16

The method of any one of embodiments 1-15, wherein the extrusion system further comprises a hopper connected to an inlet port at a first end of the barrel for feeding the biomass into the feeder zone.

Embodiment 17

The method of embodiment 16, wherein the hopper further comprises a feeder configured to move the biomass from the hopper through the inlet port.

Embodiment 18

The method of embodiment 17, wherein the feeder is a delivery auger configured to distribute the biomass evenly into the feeder zone.

Embodiment 19

The method of any one of embodiments 1-18, further comprising adding a liquid to the biomass prior to the reaction zone.

Embodiment 20

The method of embodiment 19, wherein the liquid is water.

Embodiment 21

The method of embodiment 19 or 20, wherein the liquid is added through a sealable port located on the hopper.

Embodiment 22

The method of any one of embodiments 19-21, wherein the liquid is added in the feeder zone through one or more sealable ports on the barrel.

Embodiment 23

The method of any one of embodiments 19-22, wherein the liquid is added to increase the moisture content of the biomass to from about: 10-90%, 15-85%, 20-80%, 30-70%, or about 40-60% w/v.

Embodiment 24

The method of any one of embodiments 1-23, wherein the biomass is treated for less than 60, 59, 58, 57, 56, 55, 54, 53, 52, 51, 50, 49, 48, 47, 46, 45, 44, 43, 42, 41, 40, 38, 37, 35, 32, 30, 28, 25, 22, 20, 18, 17, 16, 15, 14, 12, 10, 8, 6, 5, 4, 2, or 1 seconds in the reaction zone.

Embodiment 25

The method of any one of embodiments 1-24, wherein the biomass is treated for about: 60, 59, 58, 57, 56, 55, 54, 53, 52, 51, 50, 49, 48, 47, 46, 45, 44, 43, 42, 41, 40, 38, 37, 35, 32, 30, 28, 25, 22, 20, 18, 17, 16, 15, 14, 12, 10, 8, 6, 5, 4, 2, or 1 seconds in the reaction zone.

Embodiment 26

The method of any one of embodiments 1-25, wherein the biomass is treated for about 30 to 60 seconds in the reaction zone.

Embodiment 27

The method of any one of embodiments 1-26, wherein the biomass is treated for about 50 seconds in the reaction zone.

Embodiment 28

The method of any one of embodiments 1-27, wherein the biomass is treated for less than 19, 18, 17, 16, 15, 14, 13, 12, 10, 9, 8, 7, 6, 5, 4, 3, 2, or 1 seconds in the reaction zone.

Embodiment 29

The method of any one of embodiments 1-28, wherein the biomass is treated for about: 20, 19, 18, 17, 16, 15, 14, 13, 12, 10, 9, 8, 7, 6, 5, 4, 3, 2, or 1 seconds in the reaction zone.

Embodiment 30

The method of any one of embodiments 1-29, wherein the biomass is treated for about 5 to 15 seconds in the reaction zone.

Embodiment 31

The method of any one of embodiments 1-30, wherein the biomass is treated for about 10 seconds in the reaction zone.

Embodiment 32

The method of any one of embodiments 1-31, wherein the elevated temperature is about: 50-500° C., 75-400° C., 100-350° C., 150-300° C., or 200-250° C.

Embodiment 33

The method of any one of embodiments 1-32, wherein the elevated temperature is about 150-300° C.

Embodiment 34

The method of any one of embodiments 1-33, wherein the elevated temperature is about 220-238° C.

Embodiment 35

The method of any one of embodiments 1-34, wherein the elevated pressure is about: 50-1000 PSI, 100-750 PSI, 200-600 PSI, 300-500 PSI or 350-450 PSI.

Embodiment 36

The method of any one of embodiments 1-35, wherein the elevated pressure is about 300-500 PSI.

Embodiment 37

The method of any one of embodiments 1-36, wherein the elevated pressure is about 325-450 PSI.

Embodiment 38

The method of any one of embodiments 1-37, further comprising injecting steam into the biomass to increase temperature and pressure.

Embodiment 39

The method of embodiment 38, wherein the steam is injected in the reaction zone.

Embodiment 40

The method of embodiment 38 or 39, wherein the steam is injected through one or more sealable ports in the barrel.

Embodiment 41

The method of any one of embodiments 1-40, wherein the extrusion system further comprises a heated jacket.

Embodiment 42

The method of any one of embodiments 1-41, further comprising adding a chemical agent to the biomass in the reaction zone.

Embodiment 43

The method of embodiment 42, wherein the chemical agent comprises an acid, a base, an ionic liquid, or a combination thereof.

Embodiment 44

The method of embodiment 43, wherein the chemical agent comprises the acid that is sulfuric acid, peroxyacetic acid, lactic acid, formic acid, acetic acid, citric acid, phosphoric acid, hydrochloric acid, sulfurous acid, chloroacetic acid, dichloroacetic acid, trichloroacetic acid, trifluoroacetic acid, oxalic acid, benzoic acid, or a combination thereof.

Embodiment 45

The method of embodiment 43, wherein the chemical agent comprises the acid that is sulfuric acid.

Embodiment 46

The method of embodiment 43, wherein the chemical agent comprises the base that is sodium hydroxide, calcium hydroxide, potassium hydroxide, ammonia, ammonia hydroxide, hydrogen peroxide or a combination thereof.

Embodiment 47

The method of any one of embodiments 42-46, wherein the chemical agent is added to a level of about: 0.1-20% w/v, 1-15% w/v, 1.5-10% w/v, 1-10% w/v, 1-5% w/v, or 2-4% w/v.

Embodiment 48

The method of any one of embodiments 42-47, wherein the chemical agent is added to a level of about 1-2% w/v.

Embodiment 49

The method of any one of embodiments 42-48, wherein the chemical agent is added to a level of about 1.5% w/v.

Embodiment 50

The method of any one of embodiments 1-49, wherein the liquid fraction comprises C5 monosaccharides in at least a 60%, 65%, 70%, 75%, 80%, 85%, 90%, 95%, 96%, 97%, 98%, or 99% yield compared to the theoretical maximum based on the biomass.

Embodiment 51

The method of any one of embodiments 1-50, wherein the liquid fraction comprises C5 monosaccharides in at least a 60% yield compared to the theoretical maximum based on the biomass.

Embodiment 52

The method of any one of embodiments 1-51, wherein the liquid fraction comprises C5 monosaccharides in at least a 75% yield compared to the theoretical maximum based on the biomass.

Embodiment 53

The method of any one of embodiments 1-52, wherein the liquid fraction comprises C5 monosaccharides in at least an 85% yield compared to the theoretical maximum based on the biomass.

Embodiment 54

The method of any one of embodiments 1-53, wherein the liquid fraction comprises C6 monosaccharides less than a 40%, 35%, 30%, 25%, 20%, 15%, 10%, or 5% yield

Embodiment 55

The method of any one of embodiments 1-54, wherein the liquid fraction comprises C6 monosaccharides less than a 30% yield compared to the theoretical maximum based on the biomass.

Embodiment 56

The method of any one of embodiments 1-55, wherein the liquid fraction comprises C6 monosaccharides less than a 25% yield compared to the theoretical maximum based on the biomass.

Embodiment 57

The method of any one of embodiments 1-56, wherein the solid particles have a size range of about: 1-500 µm, 1-250 µm, 1-200 µm, or 1-150 µm.

Embodiment 58

The method of any one of embodiments 1-57, wherein the solid particles have a size range of about 1-150 µm.

Embodiment 59

The method of any one of embodiments 1-58, wherein the solid particles have an average size of about: 1-50 µm, 5-40 µm, 10-30 µm, or 15-25 µm.

Embodiment 60

The method of any one of embodiments 1-59, wherein the solid particles have an average size of about 15-25 µm.

Embodiment 61

The method of any one of embodiments 1-60, wherein the method produces low levels of one or more inhibitor compounds.

Embodiment 62

The method of embodiment 61, wherein the one or more inhibitor compounds comprise formic acid, acetic acid, hydroxymethyl furfural, furfural, or a combination thereof.

Embodiment 63

The system of any one of embodiments 1-62, wherein the liquid fraction comprises less than 2%, 1.5%, 1%, 0.8%, 0.7%, 0.6%, 0.5%, 0.4%, or 0.3% w/w formic acid by dry weight.

Embodiment 64

The system of any one of embodiments 1-63, wherein the liquid fraction comprises less than 0.5% w/w formic acid by dry weight.

Embodiment 65

The system of any one of embodiments 1-64, wherein the liquid fraction comprises less than 0.3% w/w formic acid by dry weight.

Embodiment 66

The method of any one of embodiments 1-65, wherein less than 30, 25, 20, 15, 10, 5, 2.5, 1, or 0.5 kg of formic acid is produced per MT of dry biomass.

Embodiment 67

The method of any one of embodiments 1-66, wherein less than 10 kg of formic acid is produced per MT of dry biomass.

Embodiment 68

The method of any one of embodiments 1-67, wherein less than 2.5 kg of formic acid is produced per MT of dry biomass.

Embodiment 69

The method of any one of embodiments 1-68, wherein less than 0.5 kg of formic acid is produced per MT of dry biomass.

Embodiment 70

The method of any one of embodiments 1-69, wherein the liquid fraction comprises less than 10%, 8%, 7%, 6%, 5%, 4.5%, 4%, 3.5%, 3.4%, 3.3%, or 3.2% w/w acetic acid by dry Weight.

Embodiment 71

The method of any one of embodiments 1-70, wherein the liquid fraction comprises less than 5% w/w acetic acid by dry weight.

Embodiment 72

The method of any one of embodiments 1-71, wherein the liquid fraction comprises less than 3.5% w/w acetic acid by dry weight.

Embodiment 73

The method of any one of embodiments 1-72, wherein less than 100, 80, 60, 50, 40, 30, 25, 20, 15, 10, 5, 2.5, 1, 0.5, or 0.1 kg of acetic acid is produced per MT of dry biomass.

Embodiment 74

The method of any one of embodiments 1-73, wherein less than 20 kg of acetic acid is produced per MT of dry biomass.

Embodiment 75

The method of any one of embodiments 1-74, wherein less than 5 kg of acetic acid is produced per MT of dry biomass.

Embodiment 76

The method of any one of embodiments 1-75, wherein less than 0.5 kg of acetic acid is produced per MT of dry biomass.

Embodiment 77

The method of any one of embodiments 1-76, wherein the liquid fraction comprises less than 1%, 0.8%, 0.7%, 0.6%, 0.5%, 0.4%, 0.3%, or 0.2% w/w hydroxymethyl furfural by dry weight.

Embodiment 78

The method of any one of embodiments 1-77, wherein the liquid fraction comprises less than 0.5% w/w hydroxymethyl furfural by dry weight.

Embodiment 79

The method of any one of embodiments 1-78, wherein the liquid fraction comprises less than 0.2% w/w hydroxymethy furfural by dry weight.

Embodiment 80

The method of any one of embodiments 1-79, wherein less than 20, 15, 10, 7.5, 5, 1, 0.5, 0.1, or 0.05 kg of hydroxymethyl furfural is produced per MT of dry biomass.

Embodiment 81

The method of any one of embodiments 1-80, wherein less than 2.5 kg of hydroxymethyl furfural is produced per MT of dry biomass.

Embodiment 82

The method of any one of embodiments 1-81, wherein less than 0.5 kg of hydroxymethyl furfural is produced per MT of dry biomass.

Embodiment 83

The method of any one of embodiments 1-82, wherein less than 0.05 kg of hydroxymethyl furfural is produced per MT of dry biomass.

Embodiment 84

The method of any one of embodiments 1-83, wherein the liquid fraction comprises less than 0.5%, 0.2%, 0.1%, 0.05%, 0.01%, 0.001%, or 0.0001% w/w furfural by dry weight.

Embodiment 85

The method of any one of embodiments 1-84, wherein the liquid fraction comprises less than 0.1% w/w furfural by dry weight.

Embodiment 86

The method of any one of embodiments 1-85, wherein the liquid fraction comprises less than 0.01% w/w furfural by dry weight.

Embodiment 87

The method of any one of embodiments 1-86, wherein less than 20, 15, 10, 7.5, 5, 2, 1, 0.5, 0.1, 0.05, or 0.01 kg of furfural is produced per MT of dry biomass.

Embodiment 88

The method of any one of embodiments 1-87, wherein less than 0.5 kg of furfural is produced per MT of dry biomass.

Embodiment 89

The method of any one of embodiments 1-88, wherein less than 0.05 kg of furfural is produced per MT of dry biomass.

Embodiment 90

The method of any one of embodiments 1-89, wherein the extrusion system further comprises a pressure actuated discharge valve.

Embodiment 91

The method of embodiment 90, wherein the pressure actuated discharge valve is configured to open and close in response to pressure within the extrusion system.

Embodiment 92

The method of embodiment 90 or 91, wherein the pressure actuated discharge valve is connected to an end flange plate at a second end of the barrel.

Embodiment 93

The method of any one of embodiments 90-92, wherein the pressure actuated discharge valve comprises a variable orifice valve, a poppet valve, a ball valve, a check valve, or a rotating knife-gate valve.

Embodiment 94

The method of any one of embodiments 90-93, wherein the pressure actuated discharge valve comprises a poppet valve.

Embodiment 95

The method of any one of embodiments 90-94, wherein the pressure actuated discharge valve is connected to an actuator.

Embodiment 96

The method of embodiment 95, wherein the actuator uses pneumatic force, hydraulic force, electro-mechanical force, or a combination thereof.

Embodiment 97

The method of embodiment 95 or 96, wherein the actuator is operably coupled to a back pressure control unit.

Embodiment 98

The method of embodiment 97, wherein the back pressure control unit is operably coupled to one or more pressure gauges.

Embodiment 99

The method of embodiment 98, wherein at least one of the one or more pressure gauges monitors pressure within the reaction zone.

Embodiment 100

The method of any one of embodiments 1-99, wherein the extrusion system further comprises a flash tank.

Embodiment 101

The method of embodiment 100, wherein the flash tank collects the pretreated biomass composition as it exits the pressure actuated discharge valve.

Embodiment 102

The method of any one of embodiments 1-101, wherein the biomass comprises algae, corn, grass, straw, grain hulls, wood, bark, sawdust, paper, poplars, willows, switchgrass, alfalfa, prairie bluestem, sugar palms, nypa palm, cassava, milo, sorghum, sweet potatoes, molasses, tubers, roots, stems, sago, cassaya, tapioca, rice peas, beans, potatoes, beets, fruits, pits, sorghum, sugar cane, rice, wheat, whole grains, rye, barley, bamboo, seeds, oats, or a combination thereof, or a derivative or byproduct thereof.

Embodiment 103

The method of embodiment 102, wherein the derivative or byproduct thereof comprises corn stover, corn cobs, corn mash, corn fiber, silage, bagasse, distiller's grains, distiller's dried solubles, distiller's dried grains, condensed distiller's solubles, distiller's wet grains, distiller's dried grains with solubles, fiber, fruit peels, rice straw, rice hulls, wheat straw, barley straw, seed hulls, oat hulls, food waste, municipal sewage waste, or a combination thereof.

Embodiment 104

The method of any one of embodiments 1-103, wherein the biomass comprises a woody biomass.

Embodiment 105

The method of embodiment 104, wherein the woody biomass comprises hard wood, soft wood, or a combination thereof.

Embodiment 106

The method of any one of embodiments 1-105, wherein the biomass comprises a hard wood.

Embodiment 107

The method of any one of embodiments 1-106, further comprising hydrolyzing the solid particles comprising cellulose with one or more enzymes to produce monosaccharides.

Embodiment 108

The pretreated biomass composition produced by the method of any one of embodiments 1-107.

Embodiment 109

A system for industrial scale pretreatment of biomass, the system comprising: (a) a barrel defining an inner chamber comprising a feeder zone and a reaction zone; and (b) one or more rotatable screws configured to move the biomass through the inner chamber of the barrel from the feeder zone through the reaction zone, wherein the one or more rotatable screws comprise section elements configured to form: (1) a preconditioning section in the feeder zone that produces a homogenized biomass by reducing particle size of the biomass and evenly distributing water within the biomass, and (2) a high pressure zone that compacts the homogenized biomass to form a steam impervious plug separating the feeder zone and the reaction zone; wherein the system is configured to treat the biomass at an elevated temperature and pressure within the reaction zone for less than about one minute to produce a pretreated biomass composition comprising a liquid fraction comprising monosaccharides and solid particles comprising cellulose, lignin or a combination thereof.

Embodiment 110

The system of embodiment 109, wherein the system is configured to pretreat the biomass continuously while maintaining the steam impervious plug for at least about 1 hr, at least about 2 hrs, at least about 4 hrs, at least about 5 hrs, at least about 6 hrs, at least about 8 hrs, at least about 10 hrs, at least about 12 hrs, at least about 13 hrs, at least about 14 hrs, at least about 15 hrs, at least about 16 hrs, at least about 17 hrs, or at least about 18 hrs.

Embodiment 111

The system of embodiment 109 or 110, wherein the system is configured to pretreat the biomass continuously while maintaining the stem impervious plug for at least about 15 hrs.

Embodiment 112

The system of any one of embodiments 109-111, wherein the system is configured to pretreat the biomass at a feeding rate of from about 60 to about 350 dry kg/hr.

Embodiment 113

The system of any one of embodiments 109-112, wherein the liquid fraction comprises C5 monosaccharides and C6 monosaccharides in a w/w ratio of at least about 3.0:1, at least about 3.1:1, at least about 3.2:1, at least about 3.3:1, at least about 3.4:1, at least about 3.5:1, at least about 3.6:1, at least about 3.7:1, at least about 3.8:1, at least about 3.9:1, at least about 3.91:1, at least about 3.92:1, at least about 3.93:1, at least about 3.94:1, at least about 3.95:1, at least about 3.96:1, or at least about 4:1.

Embodiment 114

The system of any one of embodiments 109-113, wherein the liquid fraction comprises C5 monosaccharides and C6 monosaccharides in a w/w ratio of at least about 3.5:1.

Embodiment 115

The system of any one of embodiments 109-114, wherein the liquid fraction comprises C5 monosaccharides and C6 monosaccharides in a w/w ratio of at least about 3.9:1.

Embodiment 116

The system of any one of embodiments 109-115, wherein the steam impervious plug is impervious to steam at a pressure of at least 1000 psi.

Embodiment 117

The system of any one of embodiments 109-116, wherein the preconditioning section reduces particle size of the biomass by at least about 2%, at least about 5%, at least about 10%, at least about 20%, at least about 30%, at least about 40%, or at least about 50%.

Embodiment 118

The system of any one of embodiments 109-117, wherein the homogenized biomass has an average particle size about: 5-500 µm, 10-200 µm, 10-100 µm, or 15-50 µm.

Embodiment 119

The system of any one of embodiments 109-118, wherein the homogenized biomass has a particle size of about 10-100 µm.

Embodiment 120

The system of any one of embodiments 109-119, wherein the one or more rotatable screws further comprise one or more section elements that are configured to form one or more steam-permeable plugs.

Embodiment 121

The system of any one of embodiments 109-120, wherein the system comprises one, two, or three rotatable screws.

Embodiment 122

The system of embodiment 121, wherein the system comprises two rotatable screws.

Embodiment 123

The system of any one of embodiments 109-122, wherein the system is capable of processing the biomass at a rate that is at least about 1 dry metric ton per day (MT/day), 2 dry MT/day, 3 dry MT/day, 4 dry MT/day, 5 dry MT/day, 7.5 dry MT/day, 10 dry MT/day, 15 dry MT/day, 20 dry MT/day, 25 dry MT/day, 50 dry MT/day, 75 dry MT/day, dry 100 MT/day, 150 dry MT/day, or 200 dry MT/day.

Embodiment 124

The system of any one of embodiments 109-123, further comprising a hopper connected to an inlet port at a first end of the barrel for feeding the biomass into the feeder zone.

Embodiment 125

The system of embodiment 124, wherein the hopper further comprises a feeder configured to move the biomass from the hopper through the inlet port.

Embodiment 126

The system of embodiment 125, wherein the feeder is a delivery auger configured to distribute the biomass evenly into the feeder zone.

Embodiment 127

The system of any one of embodiments 109-126, wherein the barrel further comprises one or more sealable ports configured to add a liquid to the biomass in the feeder zone.

Embodiment 128

The system of embodiment 127, wherein the liquid is water.

Embodiment 129

The system of embodiment 127 or 128, wherein the liquid is added through a scalable port located on the hopper.

Embodiment 130

The system of any one of embodiments 127-129, wherein the liquid is added in the feeder zone through one or more sealable ports on the barrel.

Embodiment 131

The system of any one of embodiments 109-130, wherein the rotatable screws are capable of conveying biomass through the reaction zone in less than about: 59, 58, 57, 56, 55, 54, 53, 52, 51, 50, 49, 48, 47, 46, 45, 44, 43, 42, 41, 40, 38, 37, 35, 32, 30, 28, 25, 22, 20, 18, 17, 16, 15, 14, 12, 10, 8, 6, 5, 4, 2, or 1 seconds in the reaction zone.

Embodiment 132

The system of any one of embodiments 109-131, wherein the rotatable screws are capable of conveying biomass through the reaction zone in less than about: 60, 59, 58, 57, 56, 55, 54, 53, 52, 51, 50, 49, 48, 47, 46, 45, 44, 43, 42, 41, 40, 38, 37, 35, 32, 30, 28, 25, 22, 20, 18, 17, 16, 15, 14, 12, 10, 8, 6, 5, 4, 2, or 1 seconds.

Embodiment 133

The system of any one of embodiments 109-132, wherein the rotatable screws are capable of conveying biomass through the reaction zone in about 30 to 60 seconds.

Embodiment 134

The system of any one of embodiments 109-133, wherein the rotatable screws are capable of conveying biomass through the reaction zone in about 50 seconds.

Embodiment 135

The system of any one of embodiments 109-134, wherein the rotatable screws are capable of conveying biomass through the reaction zone in less than about 19, 18, 17, 16, 15, 14, 13, 12, 10, 9, 8, 7, 6, 5, 4, 3, 2, or 1 seconds.

Embodiment 136

The system of any one of embodiments 109-135, wherein the rotatable screws are capable of conveying biomass through the reaction zone in about: 20, 19, 18, 17, 16, 15, 14, 13, 12, 10, 9, 8, 7, 6, 5, 4, 3, 2, or 1 seconds.

Embodiment 137

The system of any one of embodiments 109-136, wherein the rotatable screws are capable of conveying biomass through the reaction zone in about 5 to 15 seconds.

Embodiment 138

The system of any one of embodiments 109-137, wherein the rotatable screws are capable of conveying biomass through the reaction zone in about 10 seconds.

Embodiment 139

The system of any one of embodiments 109-138, wherein the system is configured to maintain an elevated temperature in the reaction zone.

Embodiment 140

The system of embodiment 139, wherein the elevated temperature is provided by steam, a heat jacket, or a combination thereof.

Embodiment 141

The system of embodiment 139 or 140, wherein the elevated temperature is provided by steam.

Embodiment 142

The system of any one of embodiments 139-141, wherein the elevated temperature is about: 50-500° C., 75-400° C., 100-350° C., 150-300° C., or 200-250° C.

Embodiment 143

The system of any one of embodiments 139-140, wherein the elevated temperature is about 150-300° C.

Embodiment 144

The system of any one of embodiments 139-143, wherein the elevated temperature is about 220-238° C.

Embodiment 145

The system of any one of embodiments 109-144, wherein the system is configured to maintain an elevated pressure in the reaction zone.

Embodiment 146

The system of embodiment 145, wherein the elevated pressure is maintained by addition of steam, liquid, biomass, or a combination thereof.

Embodiment 147

The system of embodiment 145 or 146, wherein the elevated pressure is about: 50-1000 PSI, 100-750 PSI, 200-600 PSI, 300-500 PSI or 350-450 PSI.

Embodiment 148

The system of any one of embodiments 145-147, wherein the elevated pressure is about 300-500 PSI.

Embodiment 149

The system of any one of embodiments 145-148, wherein the elevated pressure is about 325-450 PSI.

Embodiment 150

The system of any one of embodiments 109-149, wherein the barrel further comprises one or more sealable ports in the barrel configured to add steam in the reaction zone.

Embodiment 151

The system of any one of embodiments 109-150, wherein the barrel further comprises a heated jacket.

Embodiment 152

The system of any one of embodiments 109-151, wherein the barrel further comprises one or more sealable ports configured to add a chemical agent in the reaction zone.

Embodiment 153

The system of embodiment 152, wherein the chemical agent comprises an acid, a base, an ionic liquid or a combination thereof.

Embodiment 154

The system of embodiment 153, wherein the chemical agent comprises the acid that is sulfuric acid, peroxyacetic acid, lactic acid, formic acid, acetic acid, citric acid, phosphoric acid, hydrochloric acid, sulfurous acid, chloroacetic acid, dichloroacetic acid, trichloroacetic acid, trifluoroacetic acid, oxalic acid, benzoic acid, or a combination thereof.

Embodiment 155

The system of embodiment 153, wherein the chemical agent comprises the acid that is sulfuric acid.

Embodiment 156

The system of embodiment 153, wherein the chemical agent comprises the base that is sodium hydroxide, calcium hydroxide, potassium hydroxide, ammonia, ammonia hydroxide, hydrogen peroxide or a combination thereof.

Embodiment 157

The system of any one of embodiments 152-156, wherein the system is configured to add the chemical agent to a level of about: 0.1-20% w/v, 1-15% w/v, 1.5-10% w/v, 1-10% w/v, 1-5% w/v, or 2-4% w/v.

Embodiment 158

The system of any one of embodiments 152-157, wherein the system is configured to add the chemical agent to a level of about 1-2% w/v.

Embodiment 159

The system of any one of embodiments 152-158, wherein the system is configured to add the chemical agent to a level of about 1.5% w/v.

Embodiment 160

The system of any one of embodiments 152-159, wherein the barrel further comprises a pressure actuated discharge valve.

Embodiment 161

The method of embodiment 160, wherein the pressure actuated discharge valve is configured to open and close in response to pressure within the extrusion system.

Embodiment 162

The method of embodiment 160 or 161, wherein the pressure actuated discharge valve is connected to an end flange plate at a second end of the barrel.

Embodiment 163

The system of any one of embodiments 160-162, wherein the pressure actuated discharge valve comprises a variable orifice valve, a poppet valve, a ball valve, a check valve, or a rotating knife-gate valve.

Embodiment 164

The system of any one of embodiments 160-163, wherein the pressure actuated discharge valve comprises a poppet valve.

Embodiment 165

The system of any one of embodiments 160-164, wherein the pressure actuated discharge valve is connected to an actuator.

Embodiment 166

The system of embodiment 165, wherein the actuator uses pneumatic force, hydraulic force, electro-mechanical force, or a combination thereof.

Embodiment 167

The system of embodiment 165 or 166, wherein the actuator is operably coupled to a back pressure control unit.

Embodiment 168

The system of embodiment 167, wherein the back pressure control unit is operably coupled to one or more pressure gauges.

Embodiment 169

The system of embodiment 168, wherein at least one of the one or more pressure gauges monitors pressure within the reaction zone.

Embodiment 170

The system of any one of embodiments 109-169, wherein the barrel further comprises one or more ports comprising a temperature gauge, a pressure gauge, or a combination thereof.

Embodiment 171

The system of any one of embodiments 109-170, wherein the barrel further comprises a flash tank.

Embodiment 172

The system of embodiment 171, wherein the flash tank collects the pretreated biomass composition as it exits the pressure actuated discharge valve.

Embodiment 173

The system of any one of embodiments 109-172, wherein the system is configured to produce the liquid fraction comprising C5 monosaccharides in at least a 60%, 65%, 70%, 75%, 80%, 85%, 90%, 95%, 96%, 97%, 98%, or 99% yield compared to the theoretical maximum based on the biomass.

Embodiment 174

The system of any one of embodiments 109-173, wherein the system is configured to produce the liquid fraction comprising C5 monosaccharides in at least a 60% yield compared to the theoretical maximum based on the biomass.

Embodiment 175

The system of any one of embodiments 109-174, wherein the system is configured to produce the liquid fraction comprising C5 monosaccharides in at least a 75% yield compared to the theoretical maximum based on the biomass.

Embodiment 176

The system of any one of embodiments 109-175, wherein the system is configured to produce the liquid fraction comprising C5 monosaccharides in at least an 85% yield compared to the theoretical maximum based on the biomass.

Embodiment 177

The system of any one of embodiments 109-176, wherein the system is configured to produce the liquid fraction comprising the system is configured to produce the liquid fraction comprising C6 monosaccharides less than a 40%, 35%, 30%, 25%, 20%, 15%, 10%, or 5% yield

Embodiment 178

The system of any one of embodiments 109-177, wherein the system is configured to produce the liquid fraction comprising C6 monosaccharides less than a 30% yield compared to the theoretical maximum based on the biomass.

Embodiment 179

The system of any one of embodiments 109-178, wherein the system is configured to produce the liquid fraction comprising C6 monosaccharides less than a 25% yield compared to the theoretical maximum based on the biomass.

Embodiment 180

The system of any one of embodiments 109-179, wherein the system is configured to produce the solid particles in a size range of about: 1-500 µm, 1-250 µm, 1-200 µm, or 1-150 µm.

Embodiment 181

The system of any one of embodiments 109-180, wherein the system is configured to produce the solid particles in a size range of about 1-150 µm.

Embodiment 182

The system of any one of embodiments 109-181, wherein the system is configured to produce the solid particles in an average size of about: 1-50 µm, 5-40 µm, 10-30 µm, or 15-25 µm.

Embodiment 183

The system of any one of embodiments 109-182, wherein the system is configured to produce the solid particles in an average size of about 15-25 µm.

Embodiment 184

The system of any one of embodiments 109-183, wherein the system produces low levels of one or more inhibitor compounds.

Embodiment 185

The system of embodiment 184, wherein the one or more inhibitor compounds comprise formic acid, acetic acid, hydroxymethyl furfural, furfural, or a combination thereof.

Embodiment 186

The system of any one of embodiments 109-185, wherein the system is configured to produce the liquid fraction comprising less than 2%, 1.5%, 1%, 0.8%, 0.7%, 0.6%, 0.5%, 0.4%, or 0.3% w/w formic acid by dry weight.

Embodiment 187

The system of any one of embodiments 109-186, wherein the system is configured to produce the liquid fraction comprising less than 0.5% w/w formic acid by dry weight.

Embodiment 188

The system of any one of embodiments 109-187, wherein the system is configured to produce the liquid fraction comprising less than 0.3% w/w formic acid by dry weight.

Embodiment 189

The system of any one of embodiments 109-188, wherein the system is configured to produce less than 30, 25, 20, 15, 10, 5, 2.5, 1, or 0.5 kg of formic acid per MT of dry biomass.

Embodiment 190

The system of any one of embodiments 109-186, the system is configured to produce less than 10 kg of formic acid per MT of dry biomass.

Embodiment 191

The system of any one of embodiments 109-190, the system is configured to produce less than 2.5 kg of formic acid per MT of dry biomass.

Embodiment 192

The system of any one of embodiments 109-191, the system is configured to produce less than 0.5 kg of formic acid per MT of dry biomass.

Embodiment 193

The system of any one of embodiments 109-192, wherein the system is configured to produce the liquid fraction comprising less than 10%, 8%, 7%, 6%, 5%, 4.5%, 4%, 3.5%, 3.4%, 3.3%, or 3.2% w/w acetic acid by dry weight.

Embodiment 194

The system of any one of embodiments 109-193, wherein the system is configured to produce the liquid fraction comprising less than 5% w/w acetic acid by dry weight.

Embodiment 195

The system of any one of embodiments 109-194, wherein the system is configured to produce the liquid fraction comprising less than 3.5% w/w acetic acid by dry weight.

Embodiment 196

The system of any one of embodiments 109-192, wherein the system is configured to produce less than 100, 80, 60, 50, 40, 30, 25, 20, 15, 10, 5, 2.5, 1, 0.5, or 0.1 kg of acetic acid per MT of dry biomass.

Embodiment 197

The system of any one of embodiments 109-196, wherein the system is configured to produce less than 20 kg of acetic acid per MT of dry biomass.

Embodiment 198

The system of any one of embodiments 109-197, wherein the system is configured to produce less than 5 kg of acetic acid per MT of dry biomass.

Embodiment 199

The system of any one of embodiments 109-198, wherein the system is configured to produce less than 0.5 kg of acetic acid per MT of dry biomass.

Embodiment 200

The system of any one of embodiments 109-199, wherein the system is configured to produce the liquid fraction comprising less than 1%, 0.8%, 0.7%, 0.6%, 0.5%, 0.4%, 0.3%, or 0.2% w/w hydroxymethyl furfural by dry weight.

Embodiment 201

The system of any one of embodiments 109-200, wherein the system is configured to produce the liquid fraction comprising less than 0.5% w/w hydroxymethyl furfural by dry weight.

Embodiment 202

The system of any one of embodiments 109-201, wherein the system is configured to produce the liquid fraction comprising less than 0.2% w/w hydroxymethyl furfural by dry weight.

Embodiment 203

The system of any one of embodiments 109-202, wherein the system is configured to produce less than 20, 15, 10, 7.5, 5, 2.5, 1, 0.5, 0.1, or 0.05 kg of hydroxymethyl furfural per MT of dry biomass.

Embodiment 204

The system of any one of embodiments 109-203, wherein the system is configured to produce less than 2.5 kg of hydroxymethyl furfural per MT of dry biomass.

Embodiment 205

The system of any one of embodiments 109-204, wherein the system is configured to produce less than 0.5 kg of hydroxymethyl furfural per MT of dry biomass.

Embodiment 206

The system of any one of embodiments 109-205, wherein the system is configured to produce less than 0.05 kg of hydroxymethyl furfural per MT of dry biomass.

Embodiment 207

The system of any one of embodiments 109-206, wherein the system is configured to produce the liquid fraction comprising less than 0.5%, 0.2%, 0.1%, 0.05%, 0.01%, 0.001%, or 0.0001% w/w furfural by dry weight.

Embodiment 208

The system of any one of embodiments 109-207, wherein the system is configured to produce the liquid fraction comprising less than 0.1% w/w furfural by dry weight.

Embodiment 209

The system of any one of embodiments 109-208, wherein the system is configured to produce the liquid fraction comprising less than 0.01% w/w furfural by dry weight.

Embodiment 210

The system of any one of embodiments 109-209, wherein the system is configured to produce less than 20, 15, 10, 7.5, 5, 2, 1, 0.5, 0.1, 0.05, or 0.01 kg of furfural is produced per MT of dry biomass.

Embodiment 211

The system of any one of embodiments 109-210, wherein the system is configured to produce less than 0.5 kg of furfural is produced per MT of dry biomass.

Embodiment 212

The system of any one of embodiments 109-211, wherein the system is configured to produce less than 0.05 kg of furfural is produced per MT of dry biomass.

Embodiment 213

The system of any one of embodiments 109-212, wherein the biomass comprises algae, corn, grass, straw, grain hulls, wood, bark, sawdust, paper, poplars, willows, switchgrass, alfalfa, prairie bluestem, sugar palms, nypa palm, cassava, milo, sorghum, sweet potatoes, molasses, tubers, roots, stems, sago, cassaya, tapioca, rice peas, beans, potatoes, beets, fruits, pits, sorghum, sugar cane, rice, wheat, whole grains, rye, barley, bamboo, seeds, oats, or a combination thereof, or a derivative or byproduct thereof.

Embodiment 214

The system of embodiment 213, wherein the derivative or byproduct thereof comprises corn stover, corn cobs, corn mash, corn fiber, silage, bagasse, distiller's grains, distiller's dried solubles, distiller's dried grains, condensed distiller's solubles, distiller's wet grains, distiller's dried grains with solubles, fiber, fruit peels, rice straw, rice hulls, wheat straw, barley straw, seed hulls, oat hulls, food waste, municipal sewage waste, or a combination thereof.

Embodiment 215

The system of any one of embodiments 109-214, wherein the biomass comprises a woody biomass.

Embodiment 216

The system of embodiment 215, wherein the woody biomass comprises hard wood, soft wood, or a combination thereof.

Embodiment 217

The system of any one of embodiments 109-216, wherein the biomass comprises a hard wood.

EXAMPLES

The following examples serve to illustrate certain embodiments and aspects and are not to be construed as limiting the scope thereof.

Example 1. Pretreatment of Biomass Using a Twin Screw Extruder

A twin screw extruder as diagrammed in FIG. 2 was used to perform four continuous runs of 224, 695, 1100, and 977 hr each. The extruder was run with indirect heating through the reactor walls until the end of the experiment. A flow rate of up to 136 kg/hr was reached through the extruder with direct steam injection to supply process heat. The materials selected were acid resistant. The feed was metered through a weight belt feeder and fell into a crammer feeder supplying the barrel of the extruder. Two screws intermeshed and provided rapid heat and mass transfer when steam and acid were injected through steam and acid ports connected to the cylindrical barrel of the extruder as shown in FIG. 2. The steam and acid supplying ports were sealed by reverse-flow sections in the screws. A hydraulically operated pressure control valve was seated in a ceramic seal and pressure was controlled to maintain as constant a pressure as possible in the reaction section of the extruder.

The solids were exposed to high temperature and pressure and low pH for a maximum of about 10 seconds in the reaction zone as shown in the extruder depicted in FIG. 2 before being exploded into the flash tank. Residence time in the reaction zone was controlled by the rotational time of the screws. The surge chamber above the screws in the pump feeder acted as a flash vessel, where hot water is vaporized, cooling the product and removing some of the low-boiling inhibitors, such as furfural. Under these conditions, extrusion did not appear to produce enough furfural or HMF to inhibit yeast growth or fermentation, as long as overcooking was avoided with short reaction periods. HMF and furfural, reversion inhibitors, were formed in small amounts during this pretreatment (e.g., a total of 0.3 to 0.5 wt. % of the dry pretreated product).

Example 2. Particle Size Following Pretreatment with a Twin Screw Extruder

This run was conducted to evaluate the particle size reduction that takes place during biomass pretreatment in a modified twin screw extruder. Cherry sawdust, with an average particle size of about 3 mm×3 mm×1 mm and an average moisture content of 31% was used as the raw biomass feedstock. The cherry biomass was fed into a ZSK-30 twin screw extruder, manufactured by Coperion, essentially as described in Example 1. The processing parameters used for the experiment are presented in Table 2.

TABLE 2

Particle Size Distribution Experimental Parameters

| Feedstock | Mass Throughput Dry g/min | Pressure psig | Temp. ° C. | Acid Addition g/min | Water Addition g/min | Residence Time seconds |
|---|---|---|---|---|---|---|
| Cherry Sawdust | 398.4 | 400 | 231 | 7.6 | 1134 | 10 |

The cherry sawdust was processed on a continuous basis. The final moisture content of the processed cherry sawdust was about 76.8%. Once steady state was achieved a sample of the pretreated material was collected for particle size analysis. The sample was analyzed through a Mie Scattering theory using a Horiba LA-920, capable of measuring particle diameters from 0.02 μm to 2000 μm. The results indicated a significant particle size reduction occurring throughout the pretreatment process. The average particle size was reduced from 3 mm in the raw material to 20.75 μm in the pretreated effluent. A summary of the particle size distribution is presented in FIG. 13.

Example 3

Analysis of Biomass Slurry after Pretreatment

Table 3 is a summary of various types of biomass pretreated at an optimized set of conditions, with the analysis of the resulting sugar and organic acid composition of the liquid fraction coming off of pretreatment as slurry of biomass. Water or steam was added to adjust to the desired solids content for pretreatment.

Wet distillers grain at 68.10% moisture was fed into a twin screw extruder crammer. Conditions in the extruder were set at a steam valve pressure of 39.0 kg/hr, 232° C., and an end valve pressure of 400 psi, with 4.0% $H_2SO_4$. Biomass exited the extruder as 21.8% total solids slurry. For analysis post pretreatment, the moisture content of the biomass slurry was determined using a moisture analyzer-balance. A sample of the homogenous slurry was centrifuged for 5 minutes at 6000 rpm, and the supernatant used for standard HPLC sample preparation. All sugar and organic acid analysis was performed on a Shimadzu HPLC system with a RID-10A detector and a BIORAD Aminex HPX-87H column (300× 7.8 mm). The mobile phase was 0.01N $H_2SO_4$ and the HPLC had an 8 point calibration from 0.1 g/L to 50.0 g/L.

Cherry sawdust was resifted at 34.4% moisture. Conditions in the extruder system were set at a steam valve pressure of 27.2 kg/hr, 232° C., and an end valve pressure of 400 psi, with 2.0% $H_2SO_4$. Biomass exited the system as 25.9% total solids homogeneous slurry. Biomass slurry was cooled and then analyzed as described above.

Red Maple measuring 22.50% moisture was fed to the extruder system at a steam valve pressure of 30.4 kg/hr, 232° C., and an end valve pressure of 400 psi, with 2.0% $H_2SO_4$. Biomass exited the extruder system as 29.1% total solids homogeneous slurry. The biomass slurry was cooled and then analyzed as described above.

Yellow Poplar at 37.58% moisture was fed to the extruder system at a steam valve pressure of 30.4 kg/hr, 232° C., and an end valve pressure of 400 psi, with 2.0% $H_2SO_4$. Biomass exited the extruder system as 26.8% total solids homogeneous slurry. The biomass slurry was cooled and then analyzed as described above.

The analyses of the liquid fraction of pretreated slurries produced a hemicellulose-rich extraction from the lignocellulose biomass, and a low concentration of organic acids and inhibitors.

TABLE 3

Pretreatment conditions and composition of liquid fraction of pretreated material; kg/MT indicates kilograms per dry metric ton of biomass.

| ID | Raw Feedstock | Temp. (° C.) | End Valve Pressure (PSI) | Acid Dosing (%) | Steam Valve (lbs/hr) | Solids (%) | Glucose (kg/MT) |
|---|---|---|---|---|---|---|---|
| WDG150123-S11 | Wet Distillers Grains | 232 | 400 | 4.0 | 95 | 21.8 | 70.4 |
| HW150730-R10B6 | Cherry | 232 | 400 | 2.0 | 67 | 25.9 | 70.3 |
| HW150728-R10B3 | Red Maple | 232 | 400 | 2.0 | 67 | 29.1 | 101.2 |
| HW150618-R9B1 | Yellow Poplar | 232 | 400 | 2.0 | 67 | 26.8 | 131.1 |

| ID | Raw Feedstock | Xylose (kg/MT) | Arabinose (kg/MT) | Formic Acid (kg/MT) | Acetic Acid (kg/MT) | HMF (kg/MT) | Furfural (kg/MT) |
|---|---|---|---|---|---|---|---|
| WDG150123-S11 | Wet Distillers Grains | 127.4 | 77.9 | 27.6* | 12.1 | 0.0 | 0.6 |
| HW150730-R10B6 | Cherry | 212.1 | 14.2 | 10.4 | 29.4 | 0.6 | 1.8 |
| HW150728-R10B3 | Red Maple | 204.4 | 15.3 | 11.7 | 37.2 | 1.9 | 3.0 |
| HW150618-R9B1 | Yellow Poplar | 247.6 | 0.0 | 8.3 | 56.1 | 2.8 | 5.8 |

*Indicates amount of glycerol (kg/MT) in liquid fraction of processed Wet Distillers Grains.

Table 4 provides a summary of the sugar compositional analysis of the various feedstocks outlined in Table 3 and Table 5.

Compositional Analysis

Wet distillers grain: corn grain sugar composition was analyzed using a bone dried sample of feedstock. The NREL LAP for "Determination of Structural Carbohydrates and Lignin in Biomass" (NREL/TP-510-42618: A. Sluiter, B. Hames, R. Ruiz, C. Scarlata, J. Sluiter, D. Templeton, and D. Crocker) was followed to quantify the total theoretical available sugars within the raw feedstock by using a 72% sulfuric acid hydrolysis for 1 hour at 35° C. followed by a 4% sulfuric acid hydrolysis for 1 hour at 249° C. in an autoclave. Sugar analysis was performed on a Shimadzu HPLC system with a RID-10A detector and a BIORAD Aminex HPX-87H column (300×7.8 mm). The mobile phase was 0.01N $H_2SO_4$ and the HPLC had an 8 point calibration from 0.1 g/L to 50.0 g/L.

Cherry, red maple, and yellow poplar were analyzed for sugar composition post pretreatment. The compositional analysis of theoretical monomeric sugars was determined via enzymatic hydrolysis with an overdosed amount of cellulase enzyme cocktail to hydrolyze all possible sugars present in the cellulose and hemicellulose fractions. Sugar analysis was performed on a Shimadzu HPLC system with a RID-10A detector and a BIORAD Aminex HPX-87H column (300×7.8 mm). The mobile phase was 0.01N $H_2SO_4$ and the HPLC had an 8 point calibration from 0.1 g/L to 50.0 g/L.

Table 5 summarizes sugar conversions from pretreatment and subsequent enzymatic hydrolysis as described infra. Conversion efficiencies were calculated as a percentage of the compositional analysis of monomeric sugars, taken as a theoretical maximum sugar yield.

Enzymatic Hydrolysis

The moisture content of the pretreated biomass slurry was determined using a moisture analyzer-balance. Water was added to produce a slurry of 15% total solids and the slurry was mixed to homogeneity. The pH of the slurry was adjusted to 5.2 using 10M NaOH and then 100 g aliquots of slurry were transferred into individual 250 mL shake flasks. Commercially available cellulase enzyme was added at 8 kg of protein per metric ton of dry solids into each 250 mL shake flask. Hydrolysis was carried out in a Kuhner incubator shaker (Climo-Shaker ISF4-X) at 50° C. and 200 rpm for the duration of 72 hr.

Samples were taken at multiple time points throughout hydrolysis and after 72 hr, conversion efficiencies were calculated. The hydrolysate samples were collected for analysis and centrifuged. The supernatant was analyzed for monomeric sugars, and organic acids and inhibitors via HPLC as described supra.

TABLE 4

Compositional analysis of raw feedstocks

| Feedstock | Average Cellulose (kg/MT) | Average Hemicellulose (kg/MT) | Average Lignin (kg/MT) | Average Glucose (kg/MT) | Average Xylose (kg/MT) | Average Arabinose (kg/MT) | Total Avail. Sugar (kg/MT) |
|---|---|---|---|---|---|---|---|
| Wet Distillers Grains | 154.1 | 228.1 | 209.2 | 169.6 | 171.9 | 79.0 | 420.5 |
| Cherry | 411.5 | 216.4 | 372.1 | 452.7 | 238.0 | 16.0 | 706.7 |
| Red Maple | 450.1 | 206.4 | 343.5 | 495.1 | 227.0 | 14.2 | 736.3 |
| Yellow Poplar | 446.8 | 226.1 | 327.1 | 491.5 | 248.7 | 0.0 | 740.2 |

TABLE 5

Sugar recovery from pretreatment and enzymatic hydrolysis, calculated as a percentage of the compositional analysis of monomeric sugars.

| Feedstock | Glucose Conversion (%) Pretreatment | Glucose Conversion (%) Enzyme Hydrolysis | Xylose Conversion (%) Pretreatment | Xylose Conversion (%) Enzyme Hydrolysis |
|---|---|---|---|---|
| Wet Distillers Grains | 41.5 | 97.0 | 74.1 | 87.1 |
| Cherry | 15.5 | 90.1 | 89.1 | 98.8 |
| Red Maple | 20.5 | 90.6 | 90.1 | 99.6 |
| Yellow Poplar | 30.6 | 85.8 | 96.3 | 97.0 |

| Feedstock | Arabinose Conversion (%) Pretreatment | Arabinose Conversion (%) Enzyme Hydrolysis | Total Sugar Conversion (%) Pretreatment | Total Sugar Conversion (%) Enzyme Hydrolysis |
|---|---|---|---|---|
| Wet Distillers Grains | 98.7 | 99.0 | 65.7 | 94.4 |
| Cherry | 88.8 | 98.1 | 42.0 | 93.2 |
| Red Maple | 100.0 | 100.0 | 43.6 | 92.9 |
| Yellow Poplar | — | — | 51.2 | 91.4 |

Example 4

In addition to the treatments described supra, numerous other types of feedstocks were processed through the herein defined apparatus. For example, waste paper from a waste management facility was ground in a Fitzmill to pass through a 2.36 mm screen and blended to 1.25 wt % in water prior to being processed. Other feedstocks included corn fiber at 25% solids, bagasse (16 runs), softwoods (33 runs), rice straw (12 runs), wheat straw (8 runs), mixed straws, barley straw (8 runs) and oat hulls (10 runs).

Example 5

The experiments were conducted in an exemplary extruder according to some embodiments of the method and system provided herein. A preconditioning section was included in the extruder to homogenize the biomass prior to the formation of a steam impervious plug in the high pressure zone. Screw configuration of the extruder is modified to include preconditioning elements so that the preconditioning section is formed prior to the high pressure zone. As a result of the preconditioning, particle size of the biomass was reduced and water was evenly distributed in the biomass. The preconditioned biomass was subject to further pretreatment as described above in the extruder. The pretreatment conditions in the reaction zone in these experiments were set as follows: pressure: 325-450 psi, temperature: 220-238° C., sulfuric acid: 1-2% v/w by dry biomass weight.

Unexpectedly, upon the addition of the preconditioning section, the run time was largely prolonged with no escape of steam through the steam impervious plug ("failure"). In one example, the system ran continuously for more than 10 hr without failure. In another example, the system ran continuously for about 18 hr without failure. In a set of experiments, the system ran accumulatively for about 600 hr without failure. In contrast, an otherwise similar exemplary system but without the preconditioning section ran about 0.5 hour before failure. This difference suggests that the preconditioning process facilitated the maintenance of the steam impermeability of the steam impervious plug, offering more operability for scaling-up the process and potentially better pretreatment outcome.

Another improvement observed with the addition of the preconditioning section was the broader throughput rate range that the system can work with as compared to an otherwise similar system without the preconditioning section. In one experiment, the system could operate with a range of about 60-350 dry kg/hr biomass flow rate without failure. In contrast, an otherwise similar system but without the preconditioning section could only work with a smaller range of throughput rate, about 90 to 200 dry kg/hr.

Example 6

The experiment was conducted in similar extruder as tested in Example 5 to examine production of sugar stream according to one exemplary embodiment of the present disclosure. The feedstock was sawdust comprised of maple or maple and cherry wood and 97 data points were taken during these treatment runs. The products of these runs were analyzed for monomeric sugars, organic acids and inhibitors via HPLC as described supra, and the results of these analyses showed a condition of 400 psi and 2% acid yielded desired results for most feedstocks.

These analyses showed that, by controlling pretreatment pressure and temperature in this system, a consistent, directed outcome of C5:C6 sugar released could be achieved. In one example, the operating parameters for pretreatment was determined to be 300 psi, 1.5% acid to achieve a 3.91 C5:C6 ratio.

The quantitative HPLC analysis for a 30% C5 rich stream resulting from treatment at 300-325 psi and 1.5 to 1.75% sulfuric acid levels is shown below in Table 6.

TABLE 6

Quantitative Analysis of a 30% C5 rich Stream

| ID# | Name | Return Time | Area | Height | Concentration (g/L) |
|---|---|---|---|---|---|
| 1 | Glucose | 9.152 | 486709 | 32886 | 65.447 |
| 2 | Xylose | 9.800 | 1544291 | 94814 | 216.411 |
| 3 | Arabinose | 10.594 | 108771 | 6050 | 14.925 |
| 4 | Xylitol | 11.175 | 9850 | 496 | 1.329 |
| 5 | Formic acid | 13.827 | 2341 | 133 | 0.902 |
| 6 | Acetic acid | 15.009 | 34311 | 1666 | 9.820 |
| 7 | Ethanol | 22.215 | 0 | 0 | 0.000 |
| 8 | HMF | 27.828 | 5258 | 153 | 0.594 |
| 9 | Furfural | 40.865 | 0 | 0 | 0.000 |

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. An industrial scale method for pretreating biomass in an extrusion system, wherein the extrusion system comprises:
    (i) a barrel defining an inner chamber comprising (1) a feeder zone that comprises a preconditioning section, (2) a high pressure zone, and (3) a reaction zone; and
    (ii) one or more rotatable screws configured to move the biomass through the extrusion system from the feeder zone to the high pressure zone to the reaction zone, the method comprising:
    (a) feeding the biomass into the feeder zone of the extrusion system, and moving the biomass via the one or more rotatable screws through the extrusion system from the feeder zone to the high pressure zone to the reaction zone;
    (b) homogenizing the biomass within the preconditioning section in the feeder zone and prior to forming a plug in the biomass, by reducing particle size of the biomass and evenly distributing water within the biomass;
    (c) compacting in the high pressure zone the biomass out of the preconditioning section to form a steam impervious plug, wherein pressure within the plug is at least 1000 PSI; and
    (d) treating the biomass at an elevated temperature and pressure within the reaction zone for less than about one minute to produce a pretreated biomass composition comprising a liquid/solids fraction comprising monosaccharides and solid particles comprising cellulose and/or lignin.

2. The method of claim 1, wherein the extrusion system is configured to pretreat the biomass continuously while maintaining the steam impervious plug for at least about 1 hr.

3. The method of claim 2, wherein the extrusion system is configured to pretreat the biomass continuously while maintaining the steam impervious plug for at least about 15 hrs.

4. The method of claim 1, wherein the extrusion system is configured to pretreat the biomass at a feeding rate of from about 60 to about 350 dry kg/hr.

5. The method of claim 1, wherein the liquid/solids fraction comprises C5 monosaccharides and C6 monosaccharides in a w/w ratio of at least about 3.5:1.

6. The method of claim 1, wherein the steam impervious plug is impervious to steam at a pressure of at least 1000 PSI.

7. The method of claim 1, wherein the preconditioning section reduces the method comprises reducing particle size of the biomass by at least about 50% in the preconditioning section.

8. The method of claim 1, wherein the elevated temperature is about 220-238° C., and the elevated pressure is about 325-450 PSI.

9. The method of claim 1, further comprising adding sulfuric acid to the biomass in the reaction zone, wherein the sulfuric acid is added to a level of about 1-2% w/v.

10. The method of claim 1, wherein the liquid/solids fraction comprises C5 monosaccharides in at least a 75% yield compared to the theoretical maximum based on the biomass.

11. The method of claim 1, wherein the liquid/solids fraction comprises C6 monosaccharides less than a 25% yield compared to the theoretical maximum based on the biomass.

12. The method of claim 1, wherein less than 30 kg of formic acid is produced per MT of dry biomass.

13. The method of claim 1, wherein less than 100 kg of acetic acid is produced per MT of dry biomass.

14. The method of claim 1, wherein less than 5 kg of hydroxymethyl furfural is produced per MT of dry biomass.

15. The method of claim 1, wherein less than 10 kg of furfural is produced per MT of dry biomass.

16. The method of claim 1, wherein the biomass comprises algae, corn, grass, straw, grain hulls, wood, bark, sawdust, paper, poplars, willows, switchgrass, alfalfa, prairie bluestem, sugar palms, nypa palm, cassava, milo, sorghum, sweet potatoes, molasses, tubers, roots, stems, sago, cassaya, tapioca, rice peas, beans, potatoes, beets, fruits, pits, sorghum, sugar cane, rice, wheat, whole grains, rye, barley, bamboo, seeds, oats, or a combination thereof, or a derivative or byproduct thereof.

17. The method of claim 1, wherein the extrusion system is configured to pretreat the biomass continuously while maintaining the steam impervious plug for at least about 18 hours.

18. The method of claim 1, wherein the steam impervious plug is impervious to steam at a pressure of at least 500 PSI.

19. The method of claim 1, wherein the method further comprises forming one or more steam permeable plugs in the biomass within the reaction zone.

* * * * *